US010274496B2

(12) United States Patent
Raftery et al.

(10) Patent No.: US 10,274,496 B2
(45) Date of Patent: Apr. 30, 2019

(54) BIOMARKERS FOR DETECTING AND MONITORING COLON CANCER

(71) Applicant: UNIVERSITY OF WASHINGTON, Seattle, WA (US)

(72) Inventors: Daniel Raftery, Seattle, WA (US); Danijel Djukovic, Seattle, WA (US); Haiwei Gu, Seattle, WA (US); Jiangjiang Zhu, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 76 days.

(21) Appl. No.: 15/112,010

(22) PCT Filed: Jan. 16, 2015

(86) PCT No.: PCT/US2015/011869
§ 371 (c)(1),
(2) Date: Jul. 15, 2016

(87) PCT Pub. No.: WO2015/109263
PCT Pub. Date: Jul. 23, 2015

(65) Prior Publication Data
US 2016/0341729 A1 Nov. 24, 2016

Related U.S. Application Data

(60) Provisional application No. 61/993,573, filed on May 15, 2014, provisional application No. 61/947,157, filed on Mar. 3, 2014, provisional application No. 61/928,596, filed on Jan. 17, 2014.

(51) Int. Cl.
*G01N 33/574* (2006.01)

(52) U.S. Cl.
CPC ... *G01N 33/57419* (2013.01); *G01N 2800/56* (2013.01)

(58) Field of Classification Search
CPC .......... G01N 2800/06; G01N 2800/50; G01N 2800/52; G01N 2800/56; G01N 2800/60; G01N 2800/7028
See application file for complete search history.

(56) References Cited

U.S. PATENT DOCUMENTS

| 8,653,006 | B2 | 2/2014 | Raftery et al. |
| 2004/0005634 | A1 | 1/2004 | Patz et al. |
| 2012/0040383 | A1 | 2/2012 | Jia et al. |
| 2012/0122243 | A1 | 5/2012 | Kamlage et al. |
| 2013/0023056 | A1 | 1/2013 | Raftery et al. |
| 2013/0065320 | A1 | 3/2013 | Fedorak et al. |

FOREIGN PATENT DOCUMENTS

| WO | WO2011041892 A1 | 4/2011 |
| WO | WO2013171586 A1 | 11/2013 |
| WO | WO2013177222 A1 | 11/2013 |

OTHER PUBLICATIONS

Gowda, G.A. Nagana, et al. Metabolomics-Based Methods for Early Disease Diagnostics: A Review. Expert Rev Mol Diagn. Sep. 2008; 8(5): 617-633. doi:10.1586/14737159.8.5.617.
Huang, Qiang, et al. Metabolic Characterization of Hepatocellular Carcinoma Using Nontargeted Tissue Metabolomics. Cancer Res; 73(16) Aug. 15, 2013. DOI: 10.1158/0008-5472.CAN-13-0308.
Shiomi, Yuuki, et al. GCMS-based metabolomic study in mice with colitis induced by dextran sulfate sodium. Inflammatory Bowel Diseases; vol. 17, Issue 11, pp. 2261-2274, Nov. 2011. DOI: 10.1002/ibd.21616.
International Search Report and Written Opinion dated Sep. 1, 2015 for corresponding International Application PCT/US2015/011869 (WO2015109263) filed Jan. 16, 2015.
American Cancer Society. Cancer Facts & Figures 2013. Atlanta: American Cancer Society; 2013.
Ahlquist, David, et al., Next-Generation Stool DNA Test Accurately Detects Colorectal Cancer and Large Adenomas Gastroenterology, vol. 142, Issue 2, pp. 248-256.
Argiles, JM, et al., The metabolic environment of cancer. Mol Cell Biochem. May 1988;81(1):3-17.
Bain, James, et al., Metabolomics Applied to Diabetes Research. Diabetes Nov. 2009; 58(11): 2429-2443. https://doi.org/10.2337/db09-0580.
Benjamin, Daniel I., et al., Global Profiling Strategies for Mapping Dysregulated Metabolic Pathways in Cancer. Cell Metab. Nov. 7, 2012; 16(5): 565-577. doi:10.1016/j.cmet.2012.09.013.
Bi, Xuezhi, et al., Proteomic Analysis of Colorectal Cancer Reveals Alterations in Metabolic Pathways. Molecular & Cellular Proteomics 5:1119-1130, 2006.
Bond, JH, et al., Colon Polyps and Cancer. Endoscopy 2003; 35 (1): 27-35.
Chadeau-Hyam, Marc, et al., Deciphering the Complex:Methodological Overview of StatisticalModels to Derive OMICS-Based Biomarkers. Environmental and MolecularMutagenesis 54:542-557 (2013).
Chan, Eric Chun Yong, et al., Metabolic Profiling of Human Colorectal Cancer Using High-Resolution Magic Angle Spinning Nuclear Magnetic Resonance (HR-MAS NMR) Spectroscopy and Gas Chromatography Mass Spectrometry (GC/MS). Journal of Proteome Research 2009, 8, 352-361.

(Continued)

*Primary Examiner* — Christopher Adam Hixson
(74) *Attorney, Agent, or Firm* — Karen S. Canady; canady + lortz LLP

(57) ABSTRACT

A metabolic profiling approach for identifying biomarkers that provide highly sensitive and specific colorectal cancer (CRC) detection and monitoring using serum samples. The methods can be used for distinguishing CRC patients from both healthy controls and polyp patients, as well as to monitor disease progression or response to therapy. Receiver operator characteristic curves generated based on these models showed high sensitivities for differentiating CRC patients from healthy controls or polyp patients, good specificities, low false discovery rates, and excellent areas under the curve were obtained. Monte Carlo cross validation (MCCV) was also applied, demonstrating the robust diagnostic power of this metabolic profiling approach.

15 Claims, 26 Drawing Sheets

(56) References Cited

OTHER PUBLICATIONS

Chen, Zhao, et al., The Warburg effect and its cancer therapeutic implications. J Bioenerg Biomembr (2007) 39:267-274.
Chong, Il-Gyo, et al., Performance of some variable selection methods when multicollinearity is present. Chemometrics and Intelligent Laboratory Systems 78 (2005) 103-112.
Denkert, Carsten, et al., Metabolite profiling of human colon carcinoma—deregulation of TCA cycle and amino acid turnover. Molecular Cancer 2008, 7:72.
Duffy, Michael J. Carcinoembryonic Antigen as a Marker for Colorectal Cancer: Is It Clinically Useful? Clinical Chemistry 47:4 624-630 (2001).
Ehrmann-Josko, Agnieszka, et al., Impaired glucose metabolism in colorectal cancer. Scandinavian Journal of Gastroenterology, 2006; 41: 1079-1086.
Eisner, Roman, et al., A Machine-Learned Predictor of Colonic Polyps Based on Urinary Metabolomics. Hindawi Publishing Corporation. BioMed Research International. vol. 2013, Article ID 303982, 11 pages.
Fan, Teresa W-M, et al., NMR-based stable isotope resolved metabolomics in systems biochemistry. J Biomol NMR. Apr. 2011; 49(3-4): 267-280. doi:101007/s10858-011-9484-6.
Fletcher, Robert H., et al., Carcinoembryonic Antigen. Annals of Internal Medicine. 1986;104:66-73.
Fukui, Yousuke, et al., A Plasma Metabolomic Investigation of Colorectal Cancer Patients by Liquid Chromatography-Mass Spectrometry. The Open Analytical Chemistry Journal, 2010, 4, 1-9.
Garcia-Caballero, M., et al., Increased histidine decarboxylase (HDC) activity in human colorectal cancer: results of a study on ten patients. Agents Actions. Apr. 1988;23(3-4):357-60.
Gehrke, Charles W., et al., Patterns of Urinary Excretion of Modified Nucleosides. Cancer Research 39, 1150-1153, Apr. 1979.
Gu, Haiwei, et al., Metabolic profiling: are we en route to better diagnostic tests for cancer? Future Oncol. Oct. 2012 ; 8(10): 1207-1210. doi:10.2217/fon.12.113.
Hirayama, Akiyoshi, et al., Quantitative Metabolome Profiling of Colon and Stomach Cancer Microenvironment by Capillary Electrophoresis Time-of-Flight Mass Spectrometry. Cancer Res 2009;69(11):4918-25.
Hsu, Wei-Yi, et al., Analysis of urinary nucleosides as potential tumor markers in human colorectal cancer by high performance liquid chromatography/electrospray ionization tandem mass spectrometry. Clinica Chimica Acta 402 (2009) 31-37.
Huang, Qiang, et al., Metabolic Characterization of Hepatocellular Carcinoma Using Nontargeted Tissue Metabolomics. Cancer Res; 73(16); 4992-5002.
Israel, Maurice, et al., The metabolic advantage of tumor cells. Molecular Cancer 2011, 10:70.
Iwanicki-Caron, Isabelle., Usefulness of the Serum Carcinoembryonic Antigen Kinetic for Chemotherapy Monitoring in Patients With Unresectable Metastasis of Colorectal Cancer. J Clin Oncol 26:3681-3686.
Larson, Frank C., et al., A Comparison of Fast Homoarginine-Sensitive Alkaline Phosphatase and Carcinoembryonic Antigen as Markers in Colon Carcinoma. Journal of Clinical Oncology, vol. 2, No. 5 (May) 1984.
Leichtle, Alexander B., et al., Serum amino acid profiles and their alterations in colorectal cancer. Metabolomics (2012) 8:643-653.
Li, He, et al., Decreased fructose-1,6-bisphosphatase-2 expression promotes glycolysis and growth in gastric cancer cells. Molecular Cancer 2013, 12:110.
Li, Fang, et al., Lipid profiling for early diagnosis and progression of colorectal cancer using direct-infusion electrospray ionization Fourier transform ion cyclotron resonance mass spectrometry. Rapid Commun. Mass Spectrom. 2013, 27, 24-34.
Link, Alexander, et al., Fecal MicroRNAs as Novel Biomarkers for Colon Cancer Screening. Cancer Epidemiol Biomarkers Prev; 19(7); 1766-74.
Locker, Gershon Y., et al., ASCO 2006 Update of Recommendations for the Use of Tumor Markers in Gastrointestinal Cancer. J Clin Oncol 24:5313-5327.
Loftus, Neil J., et al., Global Metabolite Profiling of Human Colorectal Cancer Xenografts in Mice Using HPLC-MS/MS. J. Proteome Res. 2013, 12, 2980-2986.
Lu, Chun-Wun, et al., Overexpression of Pyruvate Dehydrogenase Kinase 3 Increases Drug Resistance and Early Recurrence in Colon Cancer. Am J Pathol 2011, 179:1405-1414; DOI:10.1016/j.ajpath. 2011.05.050.
Ludwig, Joseph A. and Weinstein, John N., Biomarkers in Cancer Staging, Prognosis and Treatment Selection. Nature Reviews Cancer 5, 845-856 (Nov. 2005).
Luo, Xiaoya, et al., MicroRNA Signatures: Novel Biomarker for Colorectal Cancer? Cancer Epidemiol Biomarkers Prev 2011;20:1272-1286. Published Online First May 6, 2011.
Ma, Yan-Lei, et al., Ultra-High Performance Liquid Chromatography—Mass Spectrometry for the Metabolomic Analysis of Urine in Colorectal Cancer. Dig Dis Sci (2009) 54:2655-2662.
Mal, Mainak, et al., Metabotyping of human colorectal cancer using two-dimensional gas chromatography mass spectrometry. Anal Bioanal Chem (2012) 403:483-493.
Marshall, Kenneth Wayne, et al., A blood-based biomarker panel for stratifying current risk for colorectal cancer. Int. J. Cancer: 126, 1177-1186 (2010).
Mook, Olaf R.F., et al., The role of gelatinases in colorectal cancer progression and metastasis. Biochimica et Biophysica Acta 1705 (2004) 69-89.
Nagrath, Deepak, et al., Metabolomics for mitochondrial and cancer studies. Biochimica et Biophysica Acta 1807 (2011) 650-663.
Nicholson, Jeremy K., et al., Metabolic phenotyping in clinical and surgical environments. Nature 491:384-392, Nov. 2012.
Nishiumi, Shin, et al., A Novel Serum Metabolomics-Based Diagnostic Approach for Colorectal Cancer. A Novel Serum Metabolomics-Based Diagnostic Approach for Colorectal Cancer. PLoS One 7(7): e40459. doi:10.1371/journal.pone.0040459.
Ong, Eng Shi, et al., Metabolic profiling in colorectal cancer reveals signature metabolic shifts during tumorigenesis. Mol Cell Proteomics. Feb. 10, 2010.
Pantel, Klaus and Brakenhoff, Ruud, Dissecting the Metastatic Cascade Nature Reviews Cancer 4, 448-456 (Jun. 2004). doi:10. 1038/nrc1370.
Patti, Gary J., et al., Metabolomics: the apogee of the omics trilogy. Nature Reviews Molecular Cell Biology 13, 263-269 (Apr. 2012). doi:10.1038/nrm3314.
Pesta, Martin, et al., Monitoring of Circulating Tumor Cells in Patients Undergoing Surgery for Hepatic Metastases from Colorectal Cancer. Anticancer Research 33: 2239-2244 (2013).
Plaks, Vicki, et al., Circulating Tumor Cells. Science. Sep. 13, 2013; 341(6151): .doi:10.1126/science.1235226.
Qiu, Yunping, et al., Urinary Metabonomic Study on Colorectal Cancer. Journal of Proteome Research 2010, 9, 1627-1634.
Qiu, Yunping, et al., Serum Metabolite Profiling of Human Colorectal Cancer Using GC-TOFMS and UPLC-QTOFMS. Journal of Proteome Research 2009, 8, 4844-4850.
Rantalainen, Mattias, et al., Statistically Integrated Metabonomic-Proteomic Studies on a Human Prostate Cancer Xenograft Model in Mice. Journal of Proteome Research 2006, 5, 2642-2655.
Reaves, Marshall Louise and Rabinowitz, Joshua. Metabolomics in systems microbiology. Current Opinion in Biotechnology 2011, 22:17-25.
Rex, Douglas, et al., American College of Gastroenterology Guidelines for Colorectal Cancer Screening 2008. Am J Gastroenterol 2009; 104:739-750; doi: 10.1038/ajg.2009.
Rhee, Eugene R et al., A Genome-Wide Association Study of the Human Metabolome in a Community-Based Cohort. Cell Metab. Jul. 2, 2013; 18(1): 130-143. doi:10.1016/j.cmet.2013.06.013.
Ritchie, Shawn A., et al., Reduced levels of hydroxylated, polyunsaturated ultra long-chain fatty acids in the serum of colorectal cancer patients: implications for early screening and detection. BMC Medicine 2010, 8:13.

(56) References Cited

OTHER PUBLICATIONS

Ritchie, Shawn A., et al., Low-serum GTA-446 anti-inflammatory fatty acid levels as a new risk factor for colon cancer. Int. J. Cancer: 132, 355-362 (2013).

Rocha, Claudia M., et al., Metabolic Signatures of Lung Cancer in Biofluids: NMR-Based Metabonomics of Blood Plasma. J Proteome Res. Sep. 2, 2011;10(9):4314-24. doi: 10.1021/pr200550p. Epub Aug. 5, 2011.

Scalbert, Augustin, et al., Mass-spectrometry-based metabolomics: limitations and recommendations for future progress with particular focus on nutrition research. Metabolomics (2009) 5:435-458.

Schoen, Robert E., et al., Increased Blood Glucose and Insulin, Body Size, and Incident Colorectal Cancer. J Natl Cancer Inst 1999;91:1147-54.

Shiomi, Yuuki, et al., GCMS-based metabolomic study in mice with colitis induced by dextran sulfate sodium. vol. 17, Issue 11, Nov. 2011:2261-2274.

Siegel, Rebecca, et al., Cancer Statistics, 2014. CA Cancer J Clin 2014;64:9-29.

Spratlin, Jennifer L, et al., Clinical Applications of Metabolomics in Oncology: A Review. Clin Cancer Res. Jan. 15, 2009; 15(2): 431-440. doi:10.1158/1078-0432.CCR-08-1059.

Staab, Hans J. et al. Slope analysis of the postoperative CEA time course and its possible application as an aid in diagnosis of disease progression in gastrointestinal cancer. vol. 136, Issue 3, Sep. 1978, pp. 322-327.

Tan, Binbin, et al., Metabonomics Identifies Serum Metabolite Markers of Colorectal Cancer. J Proteome Res. Jun. 7, 2013;12(6):3000-9. doi: 10.1021/pr400337b. Epub May 29, 2013.

Taylor, I., Liver metastases from colorectal cancer: lessons from past and present clinical studies. British Journal of Surgery 1996, 83,456-460.

Taylor, David P., et al., Comparison of compliance for colorectal cancer screening and surveillance by colonoscopy based on risk. Genet Med 2011:13(8):737-743.

Thangaraju, Muthusamy, et al., Colon cancer cells maintain low levels of pyruvate to avoid cell death caused by inhibition of HDAC1/HDAC3. Biochem. J. (2009) 417, 379-389 (Printed in Great Britain) doi:10.1042/BJ20081132.

Tocchi, Adriano, et al., Is There a Causal Connection Between Bile Acids and Colorectal Cancer? Surgery Today Feb. 1996, vol. 26, Issue 2, pp. 101-104.

Vander Heiden, Matthew G., et al., Understanding the Warburg Effect: The Metabolic Requirements of Cell Proliferation. Science. May 22, 2009; 324(5930): 1029-1033. doi:10.1126/science.1160809.

Wang, Huijan, et al., H NMR-based metabolic profiling of human rectal cancer tissue. Molecular Cancer 2013, 12:121.

Warburg, Otto, On the Origin of Cancer Cells. Science. Feb. 24, 1956, vol. 123, No. 3191: 309-314.

Weber, George, Enzymes of Purine Metabolism in Cancer. Clin Biochem. Feb. 1983;16(1):57-63.

Wei, Siwei, et al., Differentiating Hepatocellular Carcinoma from Hepatitis C Using Metabolite Profiling. Metabolites 2012, 2, 701-716; doi:10.3390/metab02040701.

Weitz, Jurgen, et al., Colorectal cancer. Lancet 2005; vol. 365, No. 9454, p. 153-165, Jan. 8, 2005.

Yanes, Oscar, et al., Expanding Coverage of the Metabolome for Global Metabolite Profiling. Anal. Chem. 2011, 83, 2152-2161.

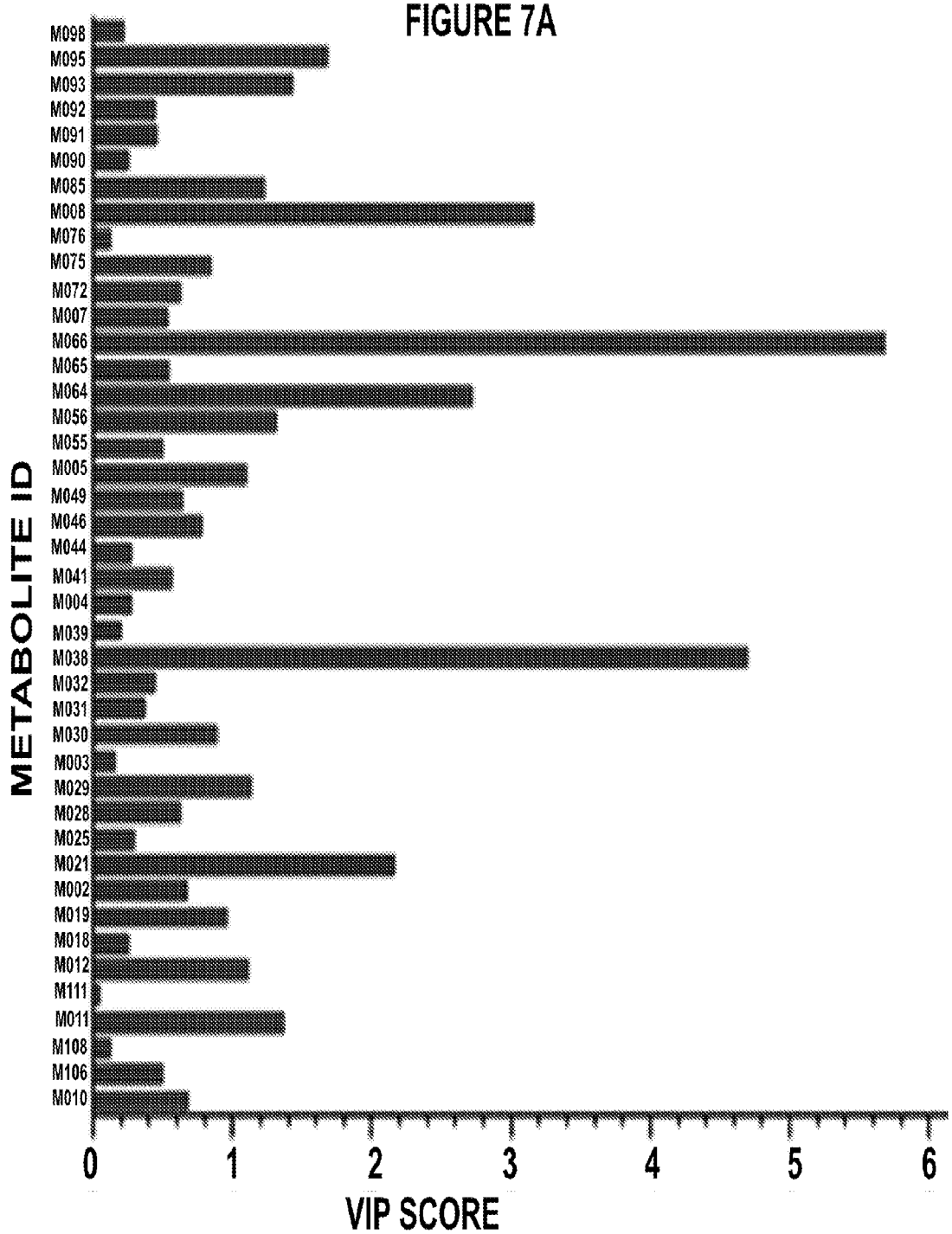

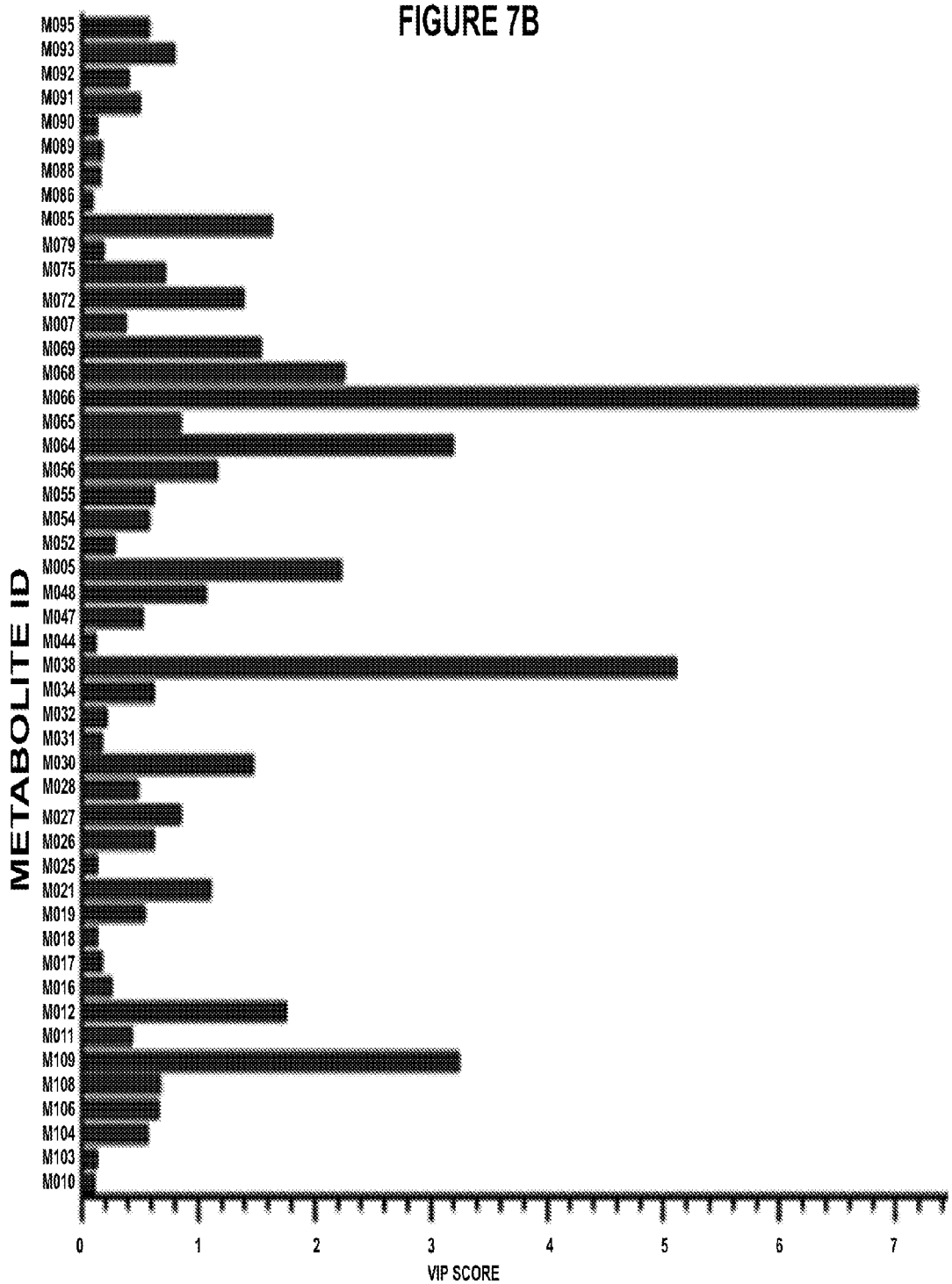

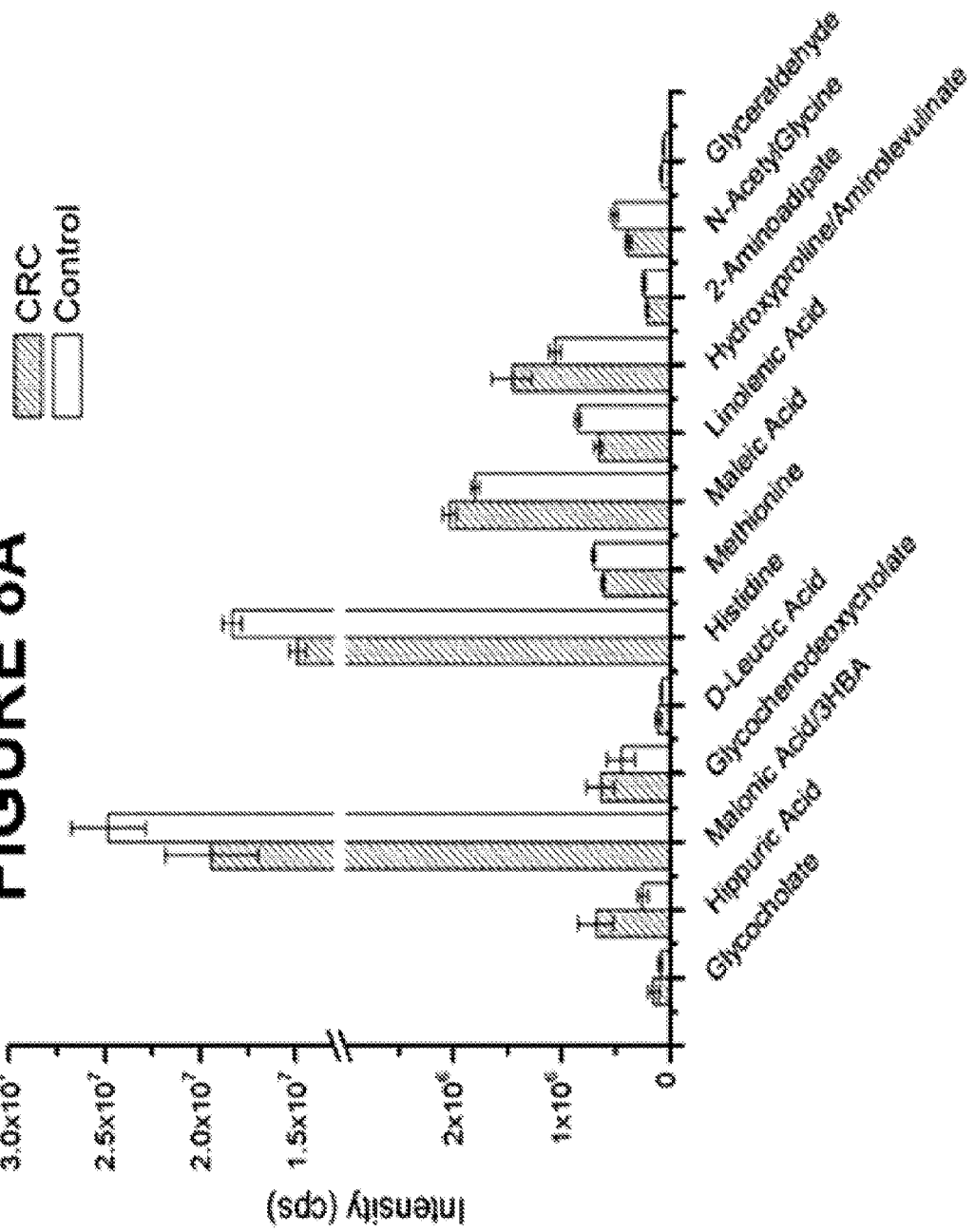

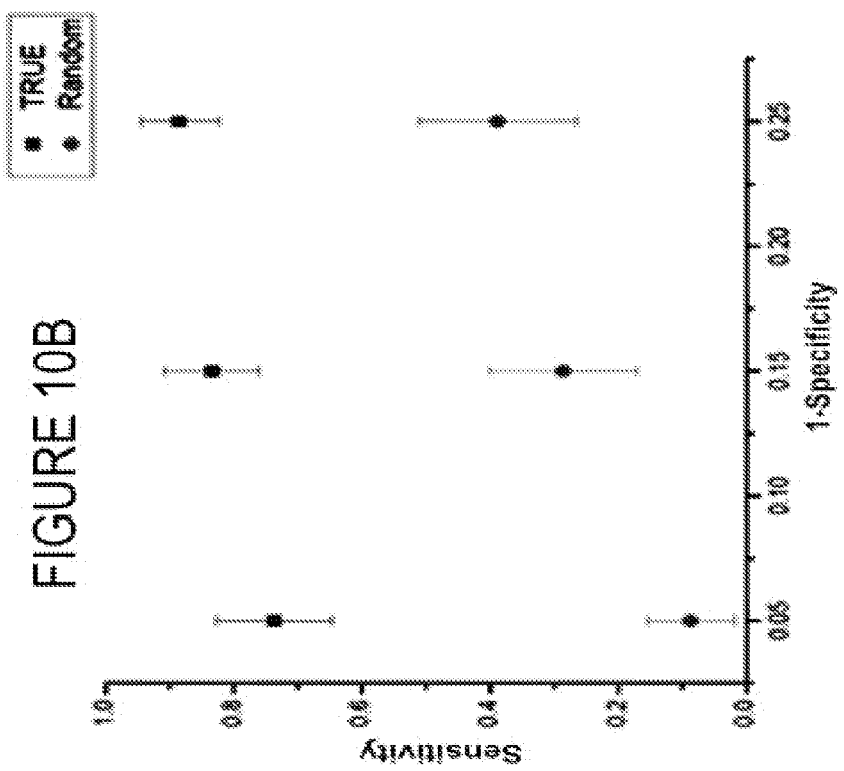
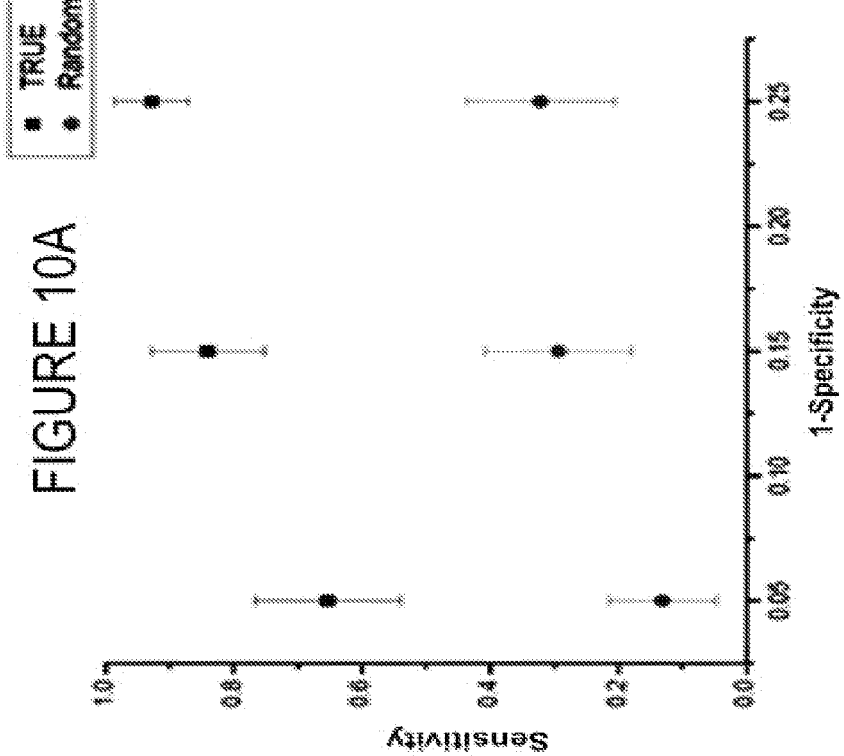

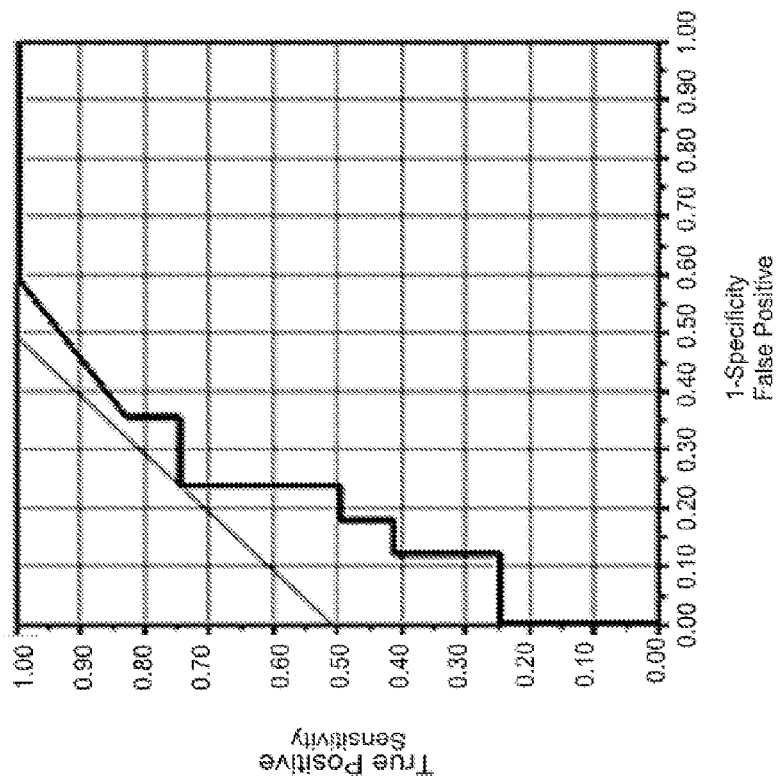
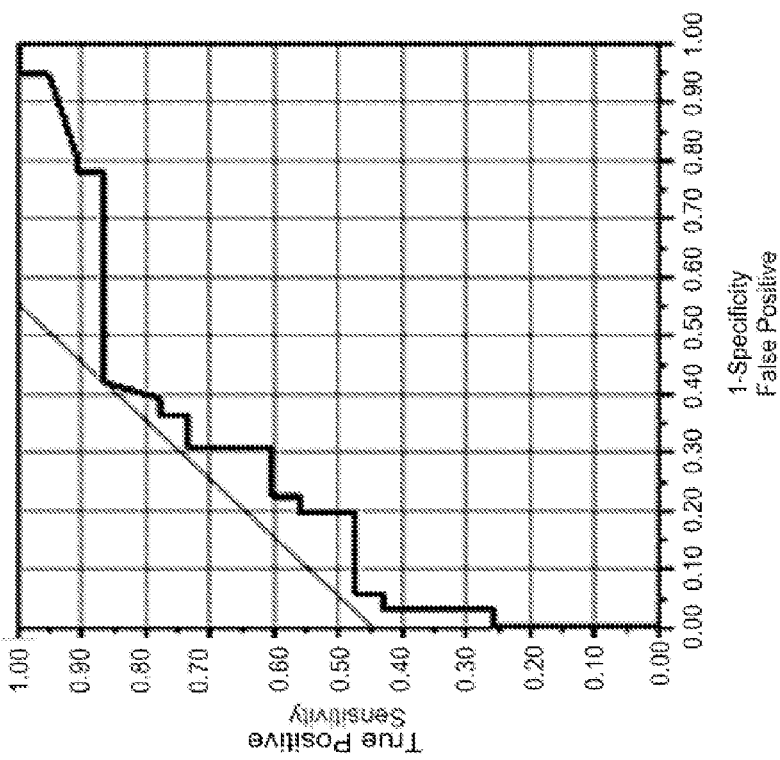

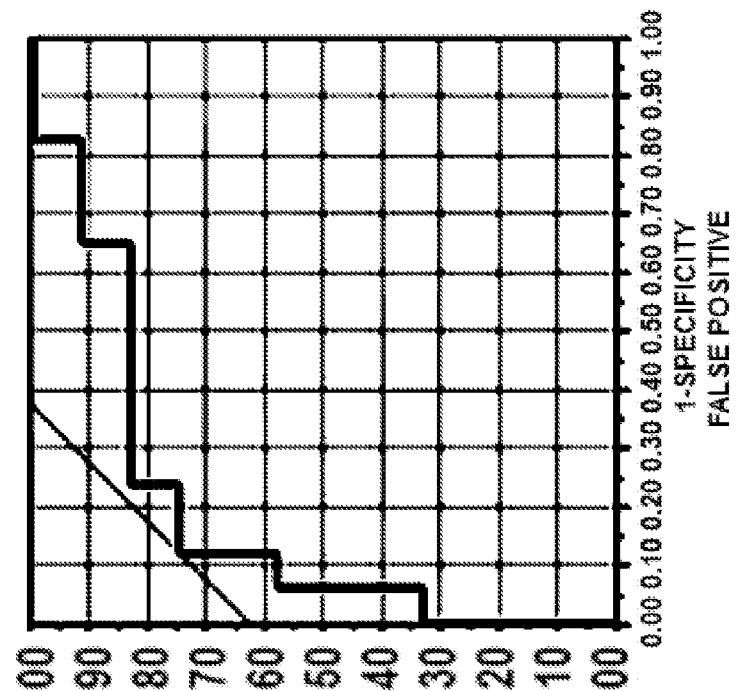
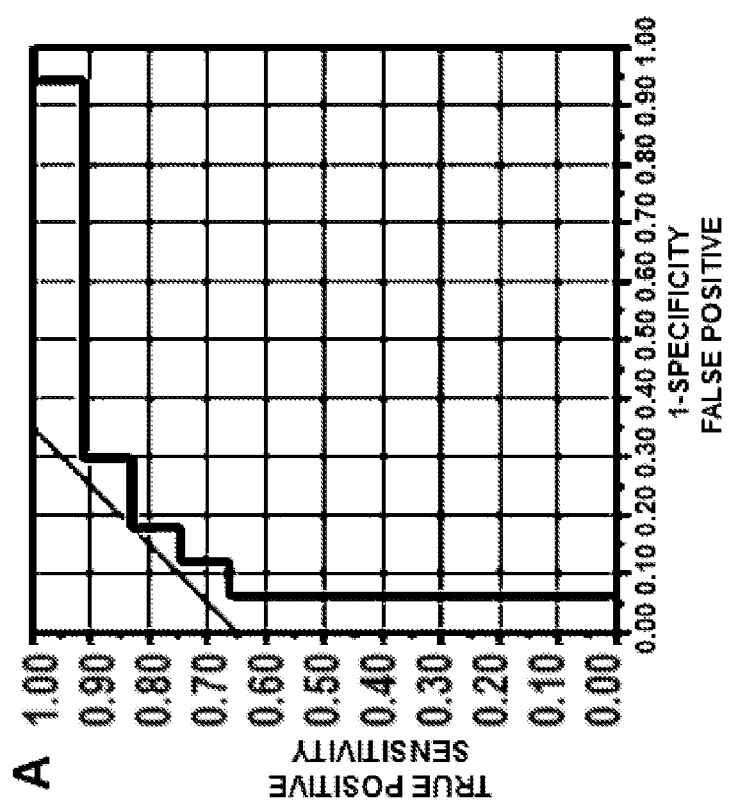

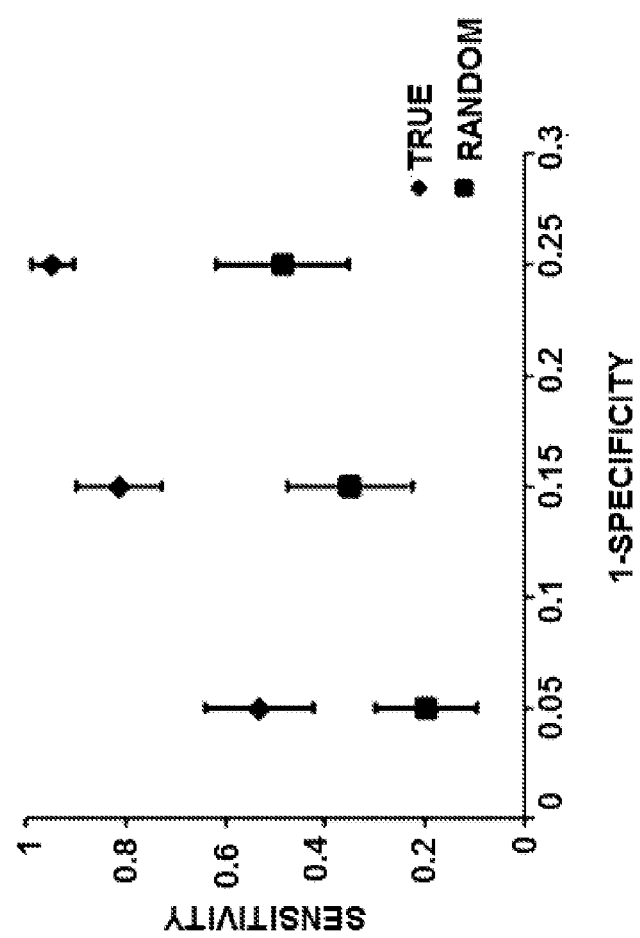
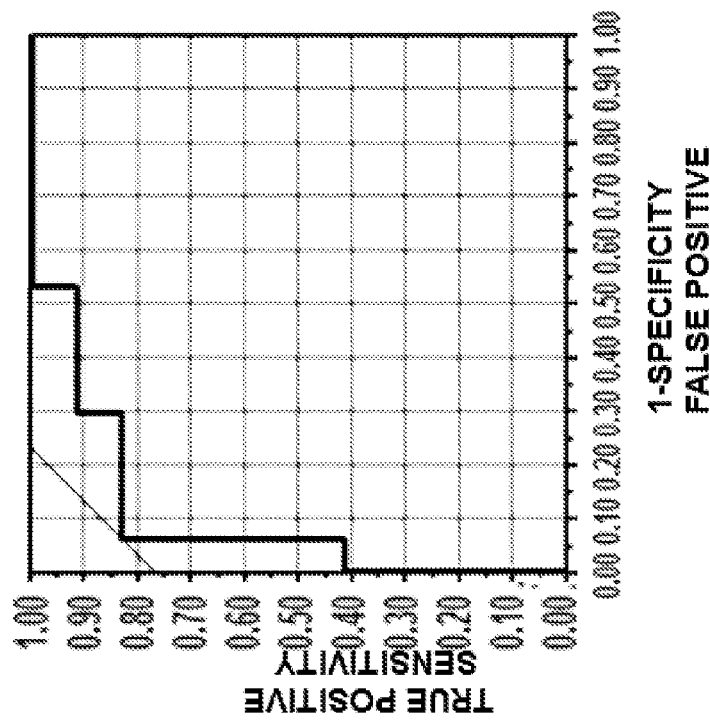
FIGURE 19A
FIGURE 19B

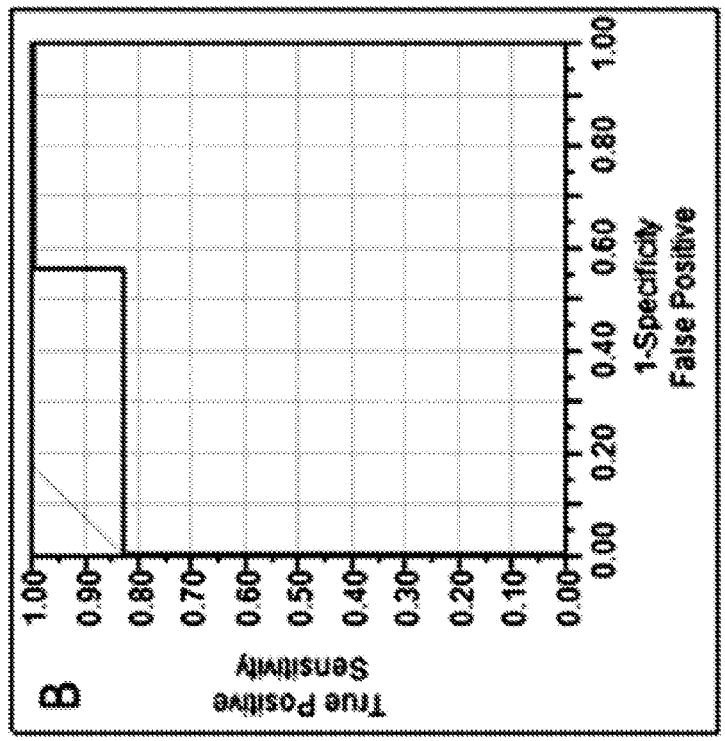
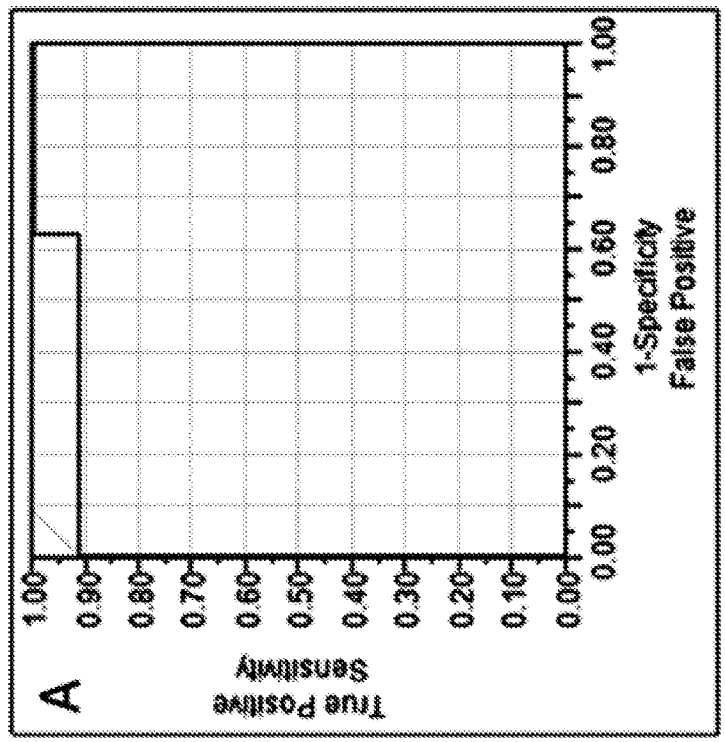
FIGURE 21A
FIGURE 21B

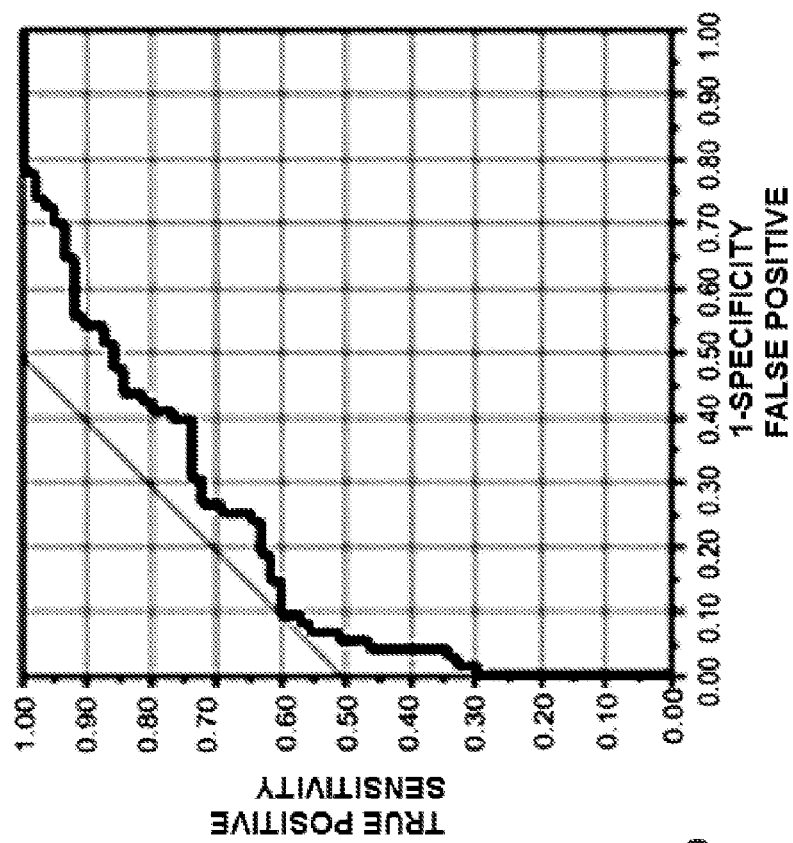
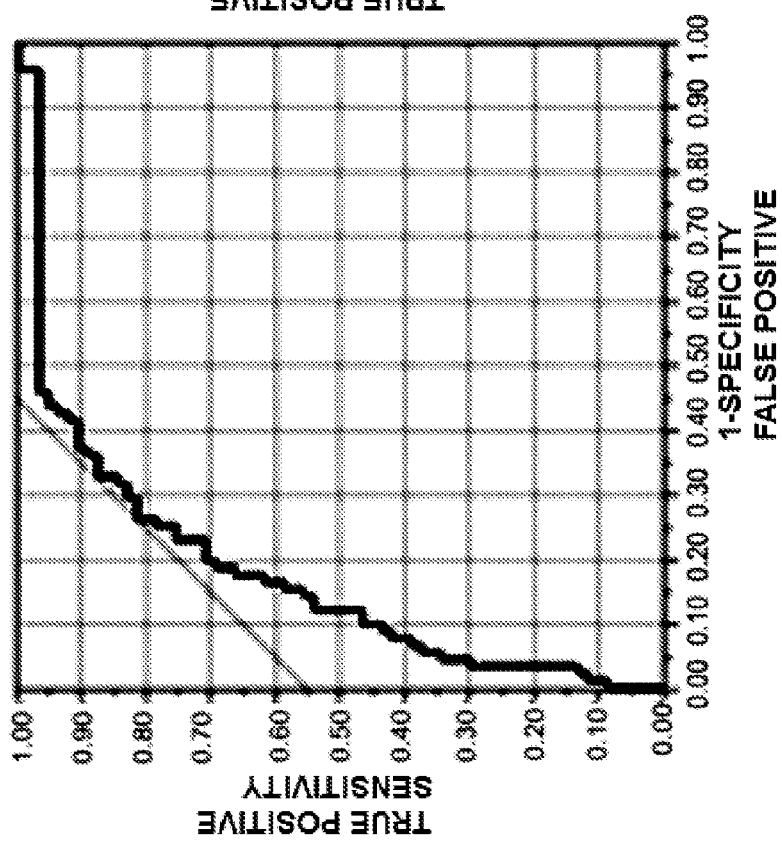

BIOMARKERS FOR DETECTING AND MONITORING COLON CANCER

This application claims the benefit of U.S. provisional patent application Nos. 61/928,596, filed Jan. 17, 2014; 61/947,157, filed Mar. 3, 2014, and 61/993,573, filed May 15, 2014, the entire contents of each of which are incorporated herein by reference.

STATEMENT REGARDING FEDERALLY SPONSORED RESEARCH

This invention was made with government support under Grant No. W81XWH-10-1-0540, awarded by the U.S. Army Medical Research and Materiel Command. The government has certain rights in the invention.

TECHNICAL FIELD OF THE INVENTION

The present invention relates to molecules and methods for detection and monitoring of colon cancer. More specifically, the invention relates to a panel of metabolites and amino acids that exhibit changes which can be detected in the bodily fluid of colorectal cancer patients. Detection of these changes provides improved methods of ascertaining colon cancer status in a subject.

BACKGROUND OF THE INVENTION

Colorectal cancer (CRC) is the third most commonly diagnosed cancer and the third leading cause of cancer death for both men and women in the US. The American Cancer Society estimates that 136,830 people will be diagnosed in 2014 with colorectal cancer and 50,310 people will die of the disease in the US. Although, the percentage of deaths due to CRC is steadily decreasing over the years, the number of deaths is still unnecessarily high.

CRC patients are usually monitored using diagnostic blood tests and/or imaging to ensure that they remain disease free and are treated promptly with second line therapies upon relapse. Additionally, malignant disease progression is often associated with drug resistance; therefore, monitoring disease progression can indicate therapeutic response and/or suggest the need for alternative therapies. In general, a monitoring test needs to be both sensitive and specific to ensure either initiation/continuation of beneficial therapies or early discontinuation/replacement of ineffective treatments.

The most widely used CRC monitoring test is carcinoembryonic antigen (CEA); CEA is a glycoprotein involved in cell adhesion that is normally produced during fetal development. Production of this protein ceases prior to birth and is, therefore, not typically present in the blood of healthy adults. Elevated levels of CEA (>2.5 ng/mL) are most commonly used as a biomarker for monitoring of CRC following tumor resection and for monitoring the response of metastatic CRC to systemic therapy. Ratio methods that compare sequential CEA measurements are also used. While CEA is FDA approved for these applications, elevated CEA levels are also associated with other types of carcinomas, such as gastric, pancreatic, lung, and breast, making it an unreliable biomarker solely for CRC cancer diagnosis or early cancer detection. CEA levels can respond to recurrent CRC with a sensitivity and specificity that is less than optimal.

There remains a need for improved and less invasive methods for monitoring and detecting CRC. In particular, there remains a need for methods that combine the analysis of amino acids in different domains, as well as of metabolites, to derive a multivariate statistical model for the detection of colon cancer. There also remains a need for targeted serum metabolic profiling of CRC. Moreover, methods are needed that consider the metabolic differences between CRC patients and two different groups of non-cancer patients, polyp patients and healthy controls, which both have important clinical impacts on correct CRC diagnosis.

SUMMARY OF THE INVENTION

The invention meets these needs and others by providing methods of detecting and monitoring colorectal cancer (CRC) in a subject. In one embodiment, the method of detecting CRC comprises measuring the amount or concentration of one or more metabolites in a sample obtained from the subject. In one embodiment, the method comprises measuring the concentrations of at least five components of a panel of a plurality of serum metabolites in a serum sample from the subject. For example, the components of the panel can be selected from the metabolites listed in the tables and in the examples below. The method further comprises determining a ratio of the concentration or amount of each of the measured components to a control serum concentration or amount of each of the components; and detecting CRC in the subject when the ratio is less than 0.95 or greater than 1.05 for at least five of the components. In some embodiments, detecting CRC occurs when the ratio determined is less than 0.9 or greater than 1.1. In some embodiments, detecting CRC occurs when the ratio determined is less than 0.85 or greater than 1.2. In some embodiments, detecting CRC occurs when the ratio determined is less than 0.8 or greater than 1.3.

In one representative embodiment, the components of the panel are selected from the group consisting of: glyceraldehyde, Hippuric Acid, Glycochenodeoxycholate, Glycocholate, Linolenic Acid, Hydroxyproline/Aminolevulinate, N-AcetylGlycine, and Leucic Acid. In another embodiment, the components of the panel are selected from the group consisting of: Oxalic Acid, Glyceraldehyde, Malonic Acid/3-hydroxybutyric acid (3HBA), Maleic Acid, N-AcetylGlycine, Glutaric Acid, Aspartic Acid, D-Leucic Acid, Allantoin, 2-Aminoadipate, phosphoenolpyruvic acid (PEP), Hippuric Acid, Kynurenate, Xanthurenate, Pentothenate, Cystathionine, Biotin, Linoleic Acid, Linolenic Acid, Glycochenodeoxycholate, Adenylosuccinate, Glycocholate, Trimethylamine-N-oxide, Alanine, Dimethylglycine, Creatinine, Proline, Hydroxyproline/Aminolevulinate, Lysine, Glutamic acid, Methionine, Histidine, L-Kynurenine, 2'-Deoxyuridine, Uridine, and Adenosine.

In one embodiment, detecting CRC occurs when the ratio of components N-AcetylGlycine and Linolenic Acid is less than 0.85, and the ratio of components Glyceraldehyde, Hippuric Acid, Glycochenodeoxycholate, Glycocholate, Hydroxyproline/Aminolevulinate, and Leucic Acid is greater than 1.2. In a typical embodiment, the at least five components comprise Hippuric Acid, Glycochenodeoxycholate, Glycocholate, Hydroxyproline/Aminolevulinate, and Leucic Acid. Optionally, the method further comprises measuring the concentration of at least one additional serum metabolite selected from the group consisting of: Oxalic Acid, Glyceraldehyde, Malonic Acid/3-hydroxybutyric acid (3HBA), Maleic Acid, N-AcetylGlycine, Glutaric Acid, Aspartic Acid, D-Leucic Acid, Allantoin, 2-Aminoadipate, phosphoenolpyruvic acid (PEP), Hippuric Acid, Kynurenate, Xanthurenate, Pentothenate, Cystathionine, Biotin, Linoleic Acid, Linolenic Acid, Glycochenodeoxycholate, Adenylosuccinate, Glycocholate, Trimethylamine-N-oxide, Alanine, Dimethylglycine, Creatinine, Proline, Hydroxyproline/Aminolevulinate, Lysine, Glutamic acid, Methionine, Histidine, L-Kynurenine, 2'-Deoxyuridine, Uridine, and Adenosine.

In another embodiment, the metabolites are amino acids, including free amino acids (FAAs), free+soluble protein amino acids (FAASPAAs), and proteome amino acids (PAAs). Representative amino acids are selected from the group consisting of: aspartic acid, glutamic acid, glutamine/lysine, and histidine from FAAs, lysine from FAASPAAs, and arginine, serine, and tyrosine from PAAs. When the relative amounts of aspartic acid and glutamic acid in FAAs increase, the relative amounts of glutamine/lysine and histidine in FAAs decrease, the relative amount of lysine in FAASPAAs decreases, and the relative amounts of arginine, serine, and tyrosine in PAAs decrease, CRC is detected. In a typical embodiment, the method of detecting colorectal cancer (CRC) in a subject comprises obtaining individual amino acids by subjecting a serum sample from the subject to acid hydrolysis and measuring the relative distribution of free amino acids (FAAs), free+soluble protein amino acids (FAASPAAs), and proteome amino acids (PAAs) in the sample as compared to a control sample; and detecting the presence of CRC in the subject when the relative amounts of aspartic acid and glutamic acid in FAAs increase, the relative amounts of glutamine/lysine and histidine in FAAs decreases, the relative amount of lysine in FAASPAAs decreases, and the relative amounts of arginine, serine, and tyrosine in PAAs decrease. In one embodiment, the measuring step comprises multivariate statistical analysis, such as, for example, logistic regression.

The invention further provides a method of detecting and/or monitoring progression of colorectal cancer (CRC) in a subject. In one embodiment, the method comprises measuring the concentrations or amounts of a plurality of serum metabolites in a serum sample from the subject and determining a ratio of the concentration or amount in the sample relative to a control. In one embodiment, the method comprises measuring the concentrations or amounts of at least five components of a panel of a plurality of serum metabolites in a serum sample from the subject, and determining a ratio of the concentration of each of the components to a control serum concentration of each of the components. CRC progression is detected in the subject when the ratio determined is less than 0.9 or greater than 1.1 for at least five of the components. In another embodiment, detecting progression of CRC occurs when the ratio determined is less than 0.85 or greater than 1.15. In another embodiment, detecting progression of CRC occurs when the ratio determined is less than 0.95 or greater than 1.2. In one embodiment, a significant statistical increase in the level of each of the at least five serum metabolites in the serum sample indicates disease progression.

In one embodiment, the components of the panel are selected from the group consisting of: glycine, normetanephrin, ribose-5-P, trimethylamine-N-oxide, histamine, adenylosuccinate, alanine, pyruvate, D-leucic acid, aminoisobutyrate, lactate, guanosine diphosphate (GDP), choline, acetoacetate, guanosine triphosphate (GTP), dimethylglycine, fumaric, deoxycytidine diphosphate (DCDP), serine, succinate, pyridoxal-5-P, creatinine, nicotinate, gibberellin, proline, glutaric acid, adipic acid, valine, malate, maleic acid, betaine, hypoxanthine, methylmalonate, threonine, alpha-ketoglutaric acid, dihydroxyacetone phosphate (DHAP), taurine, xanthine, chenodeoxycholate, creatine, phenylpropanolamine (PPA), glucose 1,6-bisphosphate (G16BP), hydroxyproline, urate, fructose 6-phosphate/fructose 1-phosphate (F6P/F1P), leucine/iso-leucine, homogentisate, oxalic acid, ornithine, phosphoenolpyruvic acid (PEP), glyceraldehyde, homocysteine, glyceraldehyde-3-phosphate (D-GA3P), glycerate, acetylcholine, glycerol-3-P, N-acetylglycine, glutamine, hyppuric acid, guanidinoacetate, glutamic acid, glucose, mevalonate, methionine, 4-pyridoxic acid, allantoin, cystamine, 2/3-phosphoglyceric acid, inositol, histidine, erythrose, homovanilate, carnitine, cystathionine, xanthurenate, phenylalanine, G1P/G6P, pentothenate, arginine, reduced glutathione, biotin, glucosamine, fructose 1,6-bisphosphate/fructose 2,6-bisphosphate (F16BP/F26BP), deoxycytidine monophosphate (DCMP), tyrosine, sucrose, deoxyuridine monophosphate (DUMP), sorbitol, 5-formyl THF, geranyl pyrophosphate, epinephrine, oxidized glutathione, thymidine cyclophosphate (DTMP), tryptophan, gama-aminobutyrate, cytidine monophosphate (CMP), 5-hydroxytryptophan, malonic acid/3-hydroxybutyric acid (3HBA), lactose, uridine, citraconic acid, cyclic guanosine monophosphate (cGMP), phosphotyrosine, adenine, adenosine monophosphate (AMP), adenosine, shikimic acid, inosine monophosphate (IMP), inosine, aconitate, prostaglandin glycerol ester (PGE), guanosine, citrulline, orotidylic acid (OMP), xanthylic acid (XMP), citric acid, uridine diphosphate (UDP), L-kinurenine, cystine, adenosine diphosphate (ADP), lysine, xanthosine, folic acid, cytosine, uracil, deoxyuridine triphosphate (DUTP), homoserine, OH-phenylpyruvate, adenosine triphosphate (ATP), niacinamide, glycochenodeoxycholate, taurocholate, 1-methylhistamine, glycocholate, fructose, asparagine, dopamine, aspartic acid, salicylurate, melatonin, methylsuccinate, 2'-deoxyuridine, orotate, myristic acid, 3-hydroxykynurenine, anthranilate, margaric acid, cytidine, glucoronate, linoleic acid, pyroglutamic acid, oxaloacetate, linolenic acid, 1-methyladenosine, propionate, galactose, 1-methylguanosine, 2-aminoadipate, N2,N2-dimethylguanosine, kynorenate, aminolevulinic acid, and 3-nitrotyrosine.

In another embodiment, the components of the panel are selected from the group consisting of: Succinate, N2,N2-Dimethylguanosine, Adenine, Citraconic Acid, Methylmalonate, 1-Methylguanosine, and 3-Nitro-tyrosine. In one embodiment, detecting CRC occurs when the ratio of component 3-Nitro-tyrosine is less than 0.9, and the ratio of components Succinate, N2,N2-Dimethylguanosine, Adenine, Citraconic Acid, Methylmalonate, and 1-Methylguanosine is greater than 1.1. In a typical embodiment, the at least five components comprise Succinate, N2,N2-Dimethylguanosine, Adenine, Citraconic Acid, and 1-Methylguanosine.

Optionally, the method further comprises measuring the concentration(s) or amount(s) of at least one additional serum metabolite selected from the group consisting of: Malonic Acid/3HBA, G16BP, Urate, Aconitate, Homogentisate, MethylSuccinate, 1-Methyladenosine, Cystathionine, Linolenic Acid, Cytidine, Pyruvate, Alanine, and gama-Aminobutyrate.

Any of the preceding methods can optionally further comprise measuring carcinoembryonic antigen (CEA) in a serum sample from the subject. A statistically significant increase in CEA relative to a control sample is indicative of progression of CRC. In some embodiments, a level of CEA greater than or equal to about 2.5 ng/mL indicates disease progression.

In a typical embodiment, the control serum is obtained from a normal, healthy subject. A known reference amount or concentration for a normal, healthy subject can also serve as the control. In some embodiments, the control serum is a sample obtained from the same subject at an earlier point in time, and is used, for example, to monitor disease progression or response to treatment.

BRIEF DESCRIPTION OF THE FIGURES

FIG. 3A shows the total ion current (TIC) of the LC-MS/MS data of FAAs (Sample 1) from a typical serum sample; FIG. 3B shows the individual extracted ion currents (EICs) for 1, tryptophan; 2, phenylalanine; 3, leucine; 4, isoleucine; 5, tyrosine; 6, methionine; 7, valine; 8, glycine; 9, alanine; 10, serine; 11, proline; 12, threonine; 13, asparagine; 14, aspartic acid; 15, lysine; 16, glutamine; 17, glutamic acid; 18, histidine; 19, arginine.

FIGS. 7A-7B. PLS-DA VIP plots indicate important metabolite biomarkers (that have VIP score >1) that can be used for prediction of cancer patients versus polyp patients or healthy controls. VIP generated based on PLS-DA models: (7A) Cancer patients vs. Healthy Controls. (7B) Cancer patients vs. Polyp patients. Metabolites IDs correspond to the IDs from list in Table S1 available online as Supporting Information for Zhu et al., J. Proteome Res., 2014, 13 (9): 4120-4130.

FIGS. 8A-8B. Bar graphs of metabolites with PLS-DA VIP scores >1 in the comparison of (8A) CRC cancer vs. Healthy controls; (8B) Cancer patients vs. Polyp patients (error bars show standard error of the mean).

FIGS. 10A-10B. Monte Carlo cross validation (MCCV) results of enhanced PLS-DA models, using metabolites (P<0.05 and VIP score >1) and clinical parameters (age, gender, smoking status, and alcohol status). True, true class models; Random, random permutation model. From the left to the right, the respective testing specificities were 0.95, 0.85 and 0.75. (10A) Cancer patients vs. Healthy Controls, (10B) Cancer patients vs. Polyps patients.

FIGS. 17A-17B. Receiver operator characteristic (ROC) curves for (17A) CEA values (AUROC=0.77) and (17B) CEA sequential sample ratios (AUROC=0.80) for disease progression vs. other disease status (stable disease and complete remission).

FIGS. 18A-18F. Individual ROC curves for the top six metabolites with p-value <0.01 comparing DP with CR and SD using sequential metabolite ratios: (18A) succinate, AUROC=0.83; (18B) N2,N2-dimethylguanosine, AUROC=0.82; (18C) citraconic acid, AUROC=0.81; (18D) adenine, AUROC=0.81; (18E) methylmalonate, AUROC=0.81; and (18F) 1-methylguanosine, AUROC=0.79.

FIGS. 19A-19B. Sensitivity and specificity when using five core metabolites. (19A) ROC curve of PLS-DA model using five metabolites (with VIP>2) for DP vs. CR+SD: AUROC=0.91; sensitivity=0.83; specificity=0.94. (19B) Monte Carlo cross validation (MCCV) PLS-DA results from the same 5 metabolites: True, true class models; Random, random permutation model. The testing group specificities were 0.95, 0.85, and 0.75.

FIGS. 21A-21B. Sensitivity and specificity when using 6-7 metabolites to compare different disease statuses. (21A)

ROC of PLS-DA model using seven metabolites (with VIP>1.8) and CEA ratios for CRC DP vs. SD. AUROC=0.95. (21B) ROC of PLS-DA model using six metabolites (with VIP>1.8) and CEA ratios for CRC DP vs. CR. AUROC=0.91.

Figure 22:
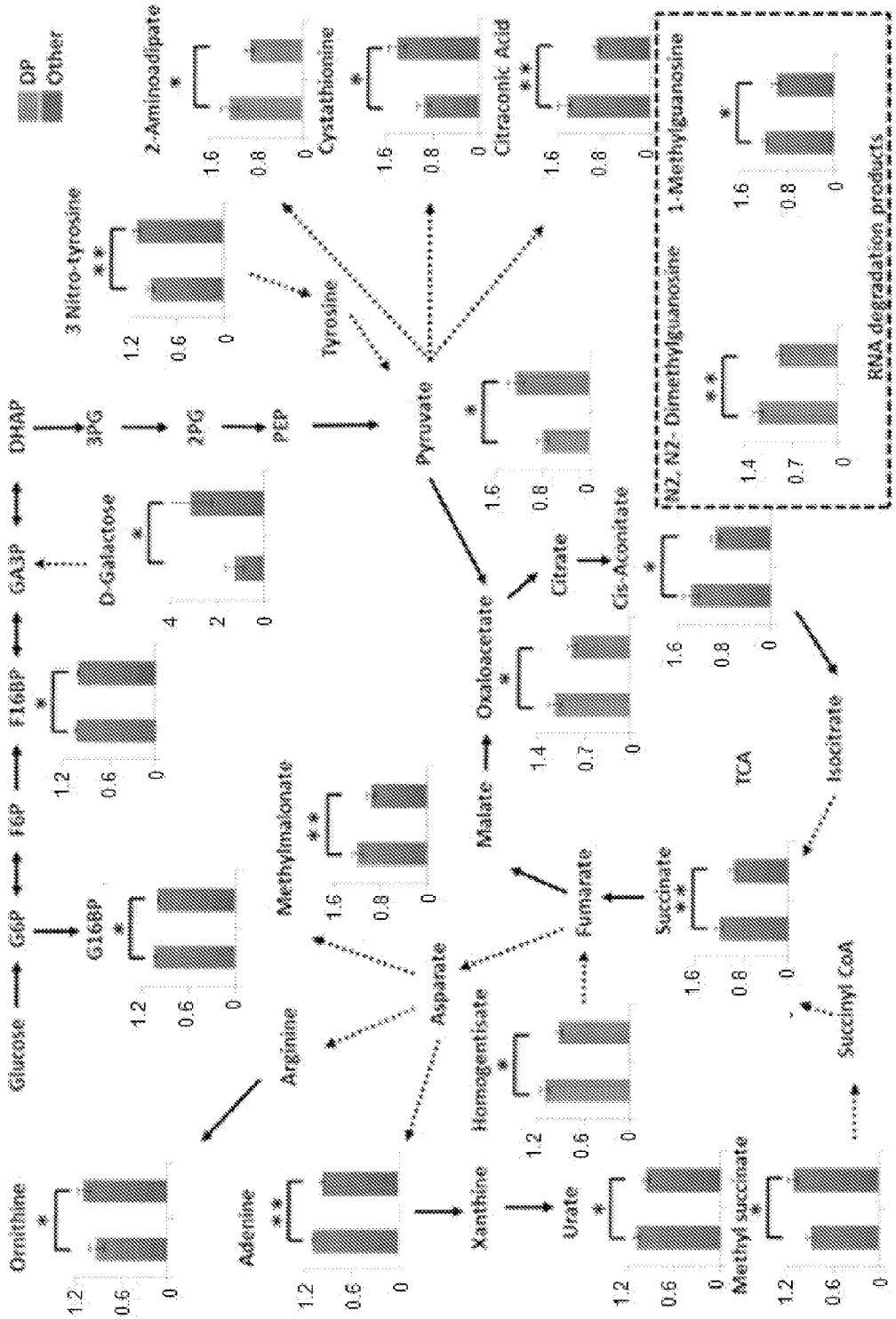

FIG. 22. Metabolic network of significantly changed metabolites in several important pathways (e.g., glycolysis, TCA, purine and pyrimidine metabolism). Bar chart: blue (left), disease progression; red (right), other disease status (CR and SD); Y axis represents the metabolite ratios to their previous blood draws. *, p<0.05; **, p<0.01.

FIGS. 23A-23D. PLS-DA models use only eight core metabolites in the comparison of (23A) CRC patients and Health controls, AUROC=0.83; and (23B) CRC patients and Polyp patients, AUROC=0.81. Monte Carlo cross validation results of 8 core metabolites PLS-DA models for (23C) CRC patients and Health controls; and (23D) CRC patients and Polyp patients.

DETAILED DESCRIPTION OF THE INVENTION

The present invention is based on the surprising discovery of a metabolic profiling approach for identifying biomarker candidates that enable highly sensitive and specific colorectal cancer (CRC) detection and monitoring using human serum samples. The analysis models established and described herein proved to be powerful for distinguishing CRC patients from both healthy controls and polyp patients. Receiver operator characteristic curves generated based on these models showed high sensitivities for differentiating CRC patients from healthy controls or polyp patients, good specificities (low false discovery rates), and excellent areas under the curve were obtained. Monte Carlo cross validation (MCCV) was also applied, demonstrating the robust diagnostic power of this metabolic profiling approach.

Definitions

All scientific and technical terms used in this application have meanings commonly used in the art unless otherwise specified. As used in this application, the following words or phrases have the meanings specified.

As used herein, a "sample" from a subject means a specimen obtained from the subject that contains blood, serum, saliva, urine, or other bodily fluid.

As used herein, measuring a "concentration" of analyte in a sample means obtaining information indicative of the relative amount of the analyte per unit volume of the sample.

As used herein, the term "subject" includes any human or non-human animal. The term "non-human animal" includes all vertebrates, e.g., mammals and non-mammals, such as non-human primates, horses, sheep, dogs, cows, pigs, chickens, amphibians, reptiles, rodents etc.

As used herein, a "control" sample, unless context clearly indicates otherwise, means a sample that is representative of normal measures of the respective analyte. The sample can be an actual sample used for testing, or a reference level or range, based on known normal measurements of the corresponding analyte. Where disease status is being monitored in a patient over time, a "baseline" sample obtained from the same subject at an earlier time point can serve as the control sample.

As used herein, "a" or "an" means at least one, unless clearly indicated otherwise.

Methods of Detecting & Monitoring Colorectal Cancer

The invention provides methods of detecting and monitoring colorectal cancer (CRC) in a subject. The methods described in detail below can be used for screening subjects as a means of early and/or relatively noninvasive detection of CRC. The methods can also be used to distinguish subjects with cancer from healthy subjects, subjects with cancer from subjects with polyps, and healthy subjects from subjects with polyps. Monitoring of CRC patients using the methods described herein also permits a less invasive means of detecting recurrence or monitoring response to therapy. Adjustments to therapy can be made more quickly and effectively through these methods, improving patient outcomes.

In one embodiment, the method of detecting CRC comprises measuring the amount or concentration of one or more metabolites in a sample obtained from the subject. In one embodiment, the method comprises measuring the concentrations of at least five components of a panel of a plurality of serum metabolites in a serum sample from the subject. For example, the components of the panel can be selected from the metabolites listed in the tables and in the examples below. The method further comprises determining a ratio of the concentration or amount of each of the measured components to a control serum concentration or amount of each of the components; and detecting CRC in the subject when the ratio is less than 0.95 or greater than 1.05 for at least five of the components. In some embodiments, detecting CRC occurs when the ratio determined is less than 0.9 or greater than 1.1. In some embodiments, detecting CRC occurs when the ratio determined is less than 0.85 or greater than 1.2. In some embodiments, detecting CRC occurs when the ratio determined is less than 0.8 or greater than 1.3.

In one representative embodiment, the components of the panel are selected from the group consisting of: glyceraldehyde, hippuric acid, glycochenodeoxycholate, glycocholate, linolenic acid, hydroxyproline/aminolevulinate, N-acetylglycine, and leucic acid. In another embodiment, the components of the panel are selected from the group consisting of: oxalic acid, glyceraldehyde, malonic acid/3-hydroxybutyric acid (3HBA), maleic acid, N-acetylglycine, glutaric acid, aspartic acid, D-leucic acid, allantoin, 2-aminoadipate, phosphoenolpyruvic acid (PEP), hippuric acid, kynurenate, xanthurenate, pentothenate, cystathionine, biotin, linoleic acid, linolenic acid, glycochenodeoxycholate, adenylosuccinate, glycocholate, trimethylamine-N-oxide, alanine, dimethylglycine, creatinine, proline, hydroxyproline/aminolevulinate, lysine, glutamic acid, methionine, histidine, L-kynurenine, 2'-deoxyuridine, uridine, and adenosine.

In one embodiment, detecting CRC occurs when the ratio of components N-acetylglycine and linolenic acid is less than 0.85, and the ratio of components glyceraldehyde, hippuric acid, glycochenodeoxycholate, glycocholate, hydroxyproline/aminolevulinate, and leucic acid is greater than 1.2. In a typical embodiment, the at least five components comprise hippuric acid, glycochenodeoxycholate, glycocholate, hydroxyproline/aminolevulinate, and leucic acid. Optionally, the method further comprises measuring the concentration of at least one additional serum metabolite selected from the group consisting of: oxalic acid, glyceraldehyde, malonic acid/3-hydroxybutyric acid (3HBA), maleic acid, N-acetylglycine, glutaric acid, aspartic acid, D-leucic acid, allantoin, 2-aminoadipate, phosphoenolpyruvic acid (PEP), hippuric acid, kynurenate, xanthurenate, pentothenate, cystathionine, biotin, linoleic acid, linolenic acid, glycochenodeoxycholate, adenylosuccinate, glycocholate, trimethylamine-N-oxide, alanine, dimethylglycine, creatinine, proline, hydroxyproline/aminolevulinate, lysine, glutamic acid, methionine, histidine, L-kynurenine, 2'-deoxyuridine, uridine, and adenosine.

In another embodiment, the metabolites are amino acids, including free amino acids (FAAs), free+soluble protein amino acids (FAASPAAs), and proteome amino acids (PAAs). Representative amino acids are selected from the group consisting of: aspartic acid, glutamic acid, glutamine/lysine, and histidine from FAAs, lysine from FAASPAAs, and arginine, serine, and tyrosine from PAAs. When the relative amounts of aspartic acid and glutamic acid in FAAs increase, the relative amounts of glutamine/lysine and histidine in FAAs decrease, the relative amount of lysine in FAASPAAs decreases, and the relative amounts of arginine, serine, and tyrosine in PAAs decrease, CRC is detected. In a typical embodiment, the method of detecting colorectal cancer (CRC) in a subject comprises obtaining individual amino acids by subjecting a serum sample from the subject to acid hydrolysis and measuring the relative distribution of free amino acids (FAAs), free+soluble protein amino acids (FAASPAAs), and proteome amino acids (PAAs) in the sample as compared to a control sample; and detecting the presence of CRC in the subject when the relative amounts of aspartic acid and glutamic acid in FAAs increase, the relative amounts of glutamine/lysine and histidine in FAAs decreases, the relative amount of lysine in FAASPAAs decreases, and the relative amounts of arginine, serine, and tyrosine in PAAs decrease. In one embodiment, the measuring step comprises multivariate statistical analysis, such as, for example, logistic regression.

The invention further provides a method of detecting and/or monitoring progression of colorectal cancer (CRC) in a subject. In one embodiment, the method comprises measuring the concentrations or amounts of a plurality of serum metabolites in a serum sample from the subject and determining a ratio of the concentration or amount in the sample relative to a control (which, for monitoring progression, can be an earlier, "baseline" sample obtained from the same subject). In one embodiment, the method comprises measuring the concentrations or amounts of at least five components of a panel of a plurality of serum metabolites in a serum sample from the subject, and determining a ratio of the concentration of each of the components to a control serum concentration of each of the components. CRC progression is detected in the subject when the ratio determined is less than 0.9 or greater than 1.1 for at least five of the components. In another embodiment, detecting progression of CRC occurs when the ratio determined is less than 0.85 or greater than 1.15. In another embodiment, detecting progression of CRC occurs when the ratio determined is less than 0.95 or greater than 1.2. In one embodiment, a significant statistical increase in the level of each of the at least five serum metabolites in the serum sample indicates disease progression. For monitoring CRC, serial blood samples are obtained and the ratio of the (5) metabolites from one time point (i.e., t1) are compared to those at an earlier time point (t0). The "control" sample in this example is really a baseline sample from the patient being monitored for disease progression, remission or stable disease.

In one embodiment, the components of the panel are selected from the group consisting of: glycine, normetanephrin, ribose-5-P, trimethylamine-N-oxide, histamine, adenylosuccinate, alanine, pyruvate, D-leucic acid, aminoisobutyrate, lactate, GDP, choline, acetoacetate, GTP, dimethylglycine, fumaric, DCDP, serine, succinate, pyridoxal-5-P, creatinine, nicotinate, gibberellin, proline, glutaric acid, adipic acid, valine, malate, maleic acid, betaine, hypoxanthine, methylmalonate, threonine, alpha-ketoglutaric acid, DHAP, taurine, xanthine, chenodeoxycholate, creatine, PPA, G16BP, hydroxyproline, urate, F6P/F1P, leucine/iso-leucine, homogentisate, oxalic acid, ornithine, PEP, glyceraldehyde, homocysteine, D-GA3P, glycerate, acetylcholine, glycerol-3-P, N-acetylglycine, glutamine, hyppuric acid, guanidinoacetate, glutamic acid, glucose, mevalonate, methionine, 4-pyridoxic acid, allantoin, cystamine, 2/3-phosphoglyceric acid, inositol, histidine, erythrose, homovanilate, carnitine, cystathionine, xanthurenate, phenylalanine, G1P/G6P, pentothenate, arginine, reduced glutathione, biotin, glucosamine, F16BP/F26BP, DCMP, tyrosine, sucrose, DUMP, sorbitol, 5-formyl THF, geranyl pyrophosphate, epinephrine, oxidized glutathione, DTMP, tryptophan, gama-aminobutyrate, CMP, 5-hydroxytryptophan, malonic acid/3HBA, lactose, uridine, citraconic acid, cGMP, phosphotyrosine, adenine, AMP, adenosine, shikimic acid, IMP, inosine, aconitate, PGE, guanosine, citrulline, OMP, XMP, citric acid, UDP, L-kinurenine, cystine, ADP, lysine, xanthosine, folic acid, cytosine, uracil, DUTP, homoserine, OH-phenylpyruvate, ATP, niacinamide, glycochenodeoxycholate, taurocholate, 1-methylhistamine, glycocholate, fructose, asparagine, dopamine, aspartic acid, salicylurate, melatonin, methylsuccinate, 2'-deoxyuridine, orotate, myristic acid, 3-hydroxykynurenine, anthranilate, margaric acid, cytidine, glucoronate, linoleic acid, pyroglutamic acid, oxaloacetate, linolenic acid, 1-methyladenosine, propionate, galactose, 1-methylguanosine, 2-aminoadipate, N2,N2-dimethylguanosine, kynorenate, aminolevulinic acid, and 3-nitrotyrosine.

In another embodiment, the components of the panel are selected from the group consisting of: Succinate, N2,N2-dimethylguanosine, adenine, citraconic acid, methylmalonate, 1-methylguanosine, and 3-nitro-tyrosine. In one embodiment, detecting CRC occurs when the ratio of component 3-Nitro-tyrosine is less than 0.9, and the ratio of components succinate, N2,N2-dimethylguanosine, adenine, citraconic acid, methylmalonate, and 1-methylguanosine is greater than 1.1. In a typical embodiment, the at least five components comprise succinate, N2,N2-dimethylguanosine, adenine, citraconic acid, and 1-methylguanosine.

Optionally, the method further comprises measuring the concentration(s) or amount(s) of at least one additional serum metabolite selected from the group consisting of: malonic acid/3HBA, G16BP, urate, aconitate, homogentisate, methylsuccinate, 1-methyladenosine, cystathionine, linoleic acid, cytidine, pyruvate, alanine, and gama-aminobutyrate.

Any of the preceding methods can optionally further comprise measuring carcinoembryonic antigen (CEA) in a serum sample from the subject. A statistically significant increase in CEA relative to a baseline or control sample is indicative of progression of CRC. In some embodiments, a level of CEA greater than or equal to about 2.5 ng/mL indicates disease progression.

In a typical embodiment, the baseline serum is obtained from a the same subject. A known reference amount or concentration for a normal, healthy subject can also serve as the control.

Methods for use in the measuring step of the method include, but are not limited to, liquid chromatography, mass spectrometry, enzymatic assay, and/or immunoassay. Representative examples of methods for measuring metabolites include Time-of-flight mass analyzers, Gas chromatography, capillary electrophoresis, Fourier transform ion cyclotron resonance (FT-ICR), LC-MS (moderately high-throughput), ultrahigh pressure liquid chromatography (UPLC), extractive electrospray ionization MS (EESI-MS), desorption electrospray atmospheric ionization MS (DESI-MS), direct analysis in real time MS (DART-MS), and matrix-assisted laser desorption/ionization MS (MALDI-MS). Such methods are reviewed in Gowda et al., 2008, *Expert Rev Mol Diagn,* 8(5):617-633.

Gowda et al., supra, also reviews statistical methods suitable for analyzing results of metabolic measurements that are suitable for use in the determining step of the above methods. Both univariate and multivariate analyses can be used in various embodiments of the invention. In one embodiment, the significant statistical difference is $p<0.1$ between disease progression and other disease status, as measured by applying the univariate Mann-Whitney U-test. In another embodiment, the significant statistical difference is $p<0.05$ between disease progression and other disease status. In yet another embodiment, the significant statistical difference is $p<0.01$ between disease progression and other disease status.

The performance of the methods can be further enhanced by considering additional variables in the analysis. For example, gender, age, smoking status, are body mass index (BMI) variables that can have a small but measurable effect on the results. In addition, other biomarkers can be used, including but not limited to, CEA, as described herein, and DNA and RNA markers. These additional variables are combined with the metabolite values using multivariate statistical methods such as PLS-DA or other similar methods.

Kits

For use in the methods described herein, kits are also within the scope of the invention. Such kits can comprise a carrier, package or container that is compartmentalized to receive one or more containers such as vials, tubes, and the like, each of the container(s) comprising one of the separate elements to be used in the method. For example, the container(s) can comprise a substrate and/or reagents for use in the methods of the invention. The kit can also include one or more containers for a reporter-means, such as a biotin-binding protein, e.g., avidin or streptavidin, bound to a detectable label, e.g., an enzymatic, florescent, or radioisotope label for use in appropriate assays.

The kit of the invention will typically comprise the container described above and one or more other containers comprising materials desirable from a commercial and user standpoint, including buffers, diluents, filters, needles, syringes, and package inserts with instructions for use. In addition, a label can be provided on the container to indicate that the composition is used for a specific diagnostic application, and can also indicate directions for use, such as those described above. Directions and or other information can also be included on an insert which is included with the kit.

EXAMPLES

The following examples are presented to illustrate the present invention and to assist one of ordinary skill in making and using the same. The examples are not intended in any way to otherwise limit the scope of the invention.

Example 1: Comprehensive Analysis of Amino Acids in Different Domains for Detecting Colon Cancer Amino acids play very important roles in biological systems, and they directly connect metabolism with the proteome. While many studies have profiled free amino acids (FAAs) or proteins, the changes of individual amino acids in the proteome due to cancer remain unknown, and their combination with those of the FAAs has not been utilized in multivariate statistical modeling. In this example, we obtained individual amino acids from peptides and proteins using traditional acid hydrolysis. FAAs, the combination of free amino acids and soluble peptide amino acids (FAASPAAs), and proteome amino acids (PAAs) were measured from the serum samples of colon cancer patients and healthy controls using liquid chromatography tandem mass spectrometry (LC-MS/MS). It was discovered that colon cancer changed the amino acid profiles and their relative distribution in the three domains. Furthermore, a multivariate statistical model, penalized logistic regression, based on the amino acids from three domains had better sensitivity and specificity than that from each individual domain. The amino acids with significantly altered levels included aspartic acid, glutamic acid, glutamine/lysine, and histidine from FAAs, lysine from FAASPAAs, and arginine, serine, and tyrosine from PAAs. This is the first combined analysis of amino acids in the three domains and provides a multivariate statistical model for detecting colon cancer.

Figure 1:
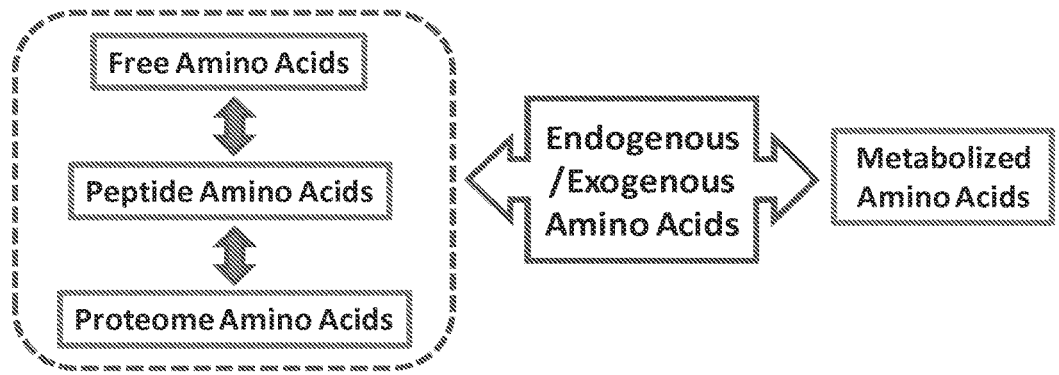
FIG. 1. The distribution of amino acids in a biological system. Endogenous or exogenous amino acids in a biological system are either metabolized or incorporated into three domains that include free amino acids (FAAs), peptide amino acids, and proteome amino acids (PAAs). In this study, we are focusing on amino acids in the three domains within the red dashed line.

As shown in FIG. 1, endogenous or exogenous amino acids in a biological system are either metabolized or incorporated into three domains that include free amino acids (FAAs), peptide amino acids, and proteome amino acids (PAAs). In fact, amino acids are a direct and important connection between metabolism and the proteome; therefore, the distribution of individual amino acids in different domains should be related to the biological status of a living system. However, although metabolomics and proteomics have been combined in previous studies (Cai et al. 2010; Casado-Vela et al. 2011), the integrated analysis of individual amino acids in various domains has not been performed, and the distribution changes of amino acids in these domains in response to different physiological status have not been investigated.

Both metabolic and proteomic profiles of amino acids are altered by colorectal cancer (CRC) (Okamoto et al. 2009; Miyagi et al. 2011; O'Dwyer et al. 2011; Randhawa et al. 2013). Currently, CRC is the third most common and deadly cancer for both females and males in the US. It was estimated by the American Cancer Society that approximately 142,820 new cases and 50,830 deaths of CRC will occur in 2013 (Siegel et al. 2013). During the early stage of tumor growth (from normal epithelium to small adenomatous polyps), the presence of nonfunctional adenomatous polyposis coli (APC) proteins resulting constitutively from the activated Wnt signaling pathway is considered as the CRC initiation event (Goss and Groden 2000). The concentration of plasma C-peptides was discovered to be positively associated with the risk of CRC (Ma et al. 2004). In addition, free amino acids were measured to be potential markers of CRC in the field of metabolomics by nuclear magnetic resonance spectroscopy (NMR) and mass spectrometry (MS), using tissue (Lean et al. 1993; Denkert et al. 2008; Chan et al. 2009; Piotto et al. 2009), serum (Qiu et al. 2009; Ritchie et al. 2010; Leichtle et al. 2012), urine (Qiu et al. 2010), or fecal water samples (Monleon et al. 2009). In one representative study, the levels of 24 amino acids and related metabolites were determined in the plasma samples from CRC patients and healthy individuals (Okamoto et al. 2009). Logistic regression was used to discriminate the cancer patients from controls, and an area under the receiver operating characteristic curve (AUROC) of 0.86 was obtained. CRC appears to lead to alterations in the amino-acid balances including those in proteins, peptides, and metabolism.

In this Example, we obtained a "snapshot" of amino acid levels in the three domains (as shown schematically within the red dashed line in FIG. 1) and examined their performance for detecting colon cancer. We applied the well-established acid hydrolysis method to obtain individual amino acids from peptides and proteins, and used liquid chromatography tandem MS (LC-MS/MS) to measure FAAs, free amino acids and soluble peptide amino acids (FAASPAAs), and PAAs from colon cancer patients and healthy controls. We further constructed penalized logistic regression models based on amino acids in the three domains, both individually and in combination. To the best of our knowledge, this is the first study that combines the analysis of amino acids in different domains to derive a multivariate statistical model for the detection of colon cancer. This study lays the foundation for further quantitative tracking of the distribution of individual amino acid levels in metabolic, peptide, and proteome profiles, which provides a new window for biological sciences and biomedical research.

Experimental Section

Chemicals

The compounds purchased from Sigma-Aldrich (St. Louis, Mo.) included acetonitrile, methanol, formic acid, and 20 amino acids (L-histidine, L-alanine, L-isoleucine, L-arginine, L-leucine, L-asparagine, L-lysine, L-aspartic acid, L-methionine, L-cysteine, L-phenylalanine, L-glutamic acid, L-threonine, L-glutamine, L-tryptophan, glycine, L-valine, L-proline, L-serine, and L-tyrosine). Hydrochloric acid (HCl) was purchased from EMD Millipore (Billerica, Mass.). L-$^{13}C_2$-tyrosine was bought from Cambridge Isotope Laboratories, Inc. (Andover, Mass.). DI water was provided in-house by a Synergy Ultrapure Water System from EMD Millipore (Billerica, Mass.).

Serum Samples

All samples were collected in accordance with the protocols approved by the Indiana University School of Medicine and Purdue University Institutional Review Boards. All subjects in the study provided informed consent according to the institutional guidelines. Patients undergoing colonoscopy for CRC screening were evaluated, and blood samples from the patients were obtained after overnight fasting and bowel preparation prior to colonoscopy. Based on the analysis of biopsied tissue, individuals were categorized as either colon cancer patients or healthy controls. All colon cancer patients in this study were newly diagnosed, and the blood samples were drawn before any surgery, chemotherapy, or radiation treatment. In total, blood samples from 28 colon cancer patients and 28 healthy controls were analyzed. The detailed demographic and clinical information for the patients and healthy controls was shown in Table 1. Each blood sample was allowed to clot for 45 min and then was centrifuged at 2000 rpm for 10 min. The serum samples were collected and evaluated for protein content using the BCA Protein Assay Kit (100-fold diluted serum, Thermo Fisher Scientific, Rockford, Ill.).

TABLE 1

Demographic and clinical information for patients and healthy controls

|  | Healthy Controls | Colon Cancer |
|---|---|---|
| Samples (patients) | 28 (28) | 28 (28) |
| Age, median (range) | 58 (18-80) | 56 (29-88) |
| BMI*, median (range) | 30.0 (21.1-43.2) | 27.5 (17.8-32.2) |

TABLE 1-continued

Demographic and clinical information for patients and healthy controls

|  | Healthy Controls | Colon Cancer |
|---|---|---|
| Gender |  |  |
| Male | 14 | 14 |
| Female | 14 | 14 |
| Stage |  |  |
| I | — | 1 |
| II | — | 2 |
| III | — | 6 |
| IV | — | 19 |
| Ethnicity |  |  |
| Caucasian | 13 | 15 |
| African American | 2 | 2 |
| Hispanic or Latino | 0 | 1 |
| NA | 13 | 10 |

*13 controls and 9 colon cancer patients don't have BMI data.

Sample Preparation

Figure 2:
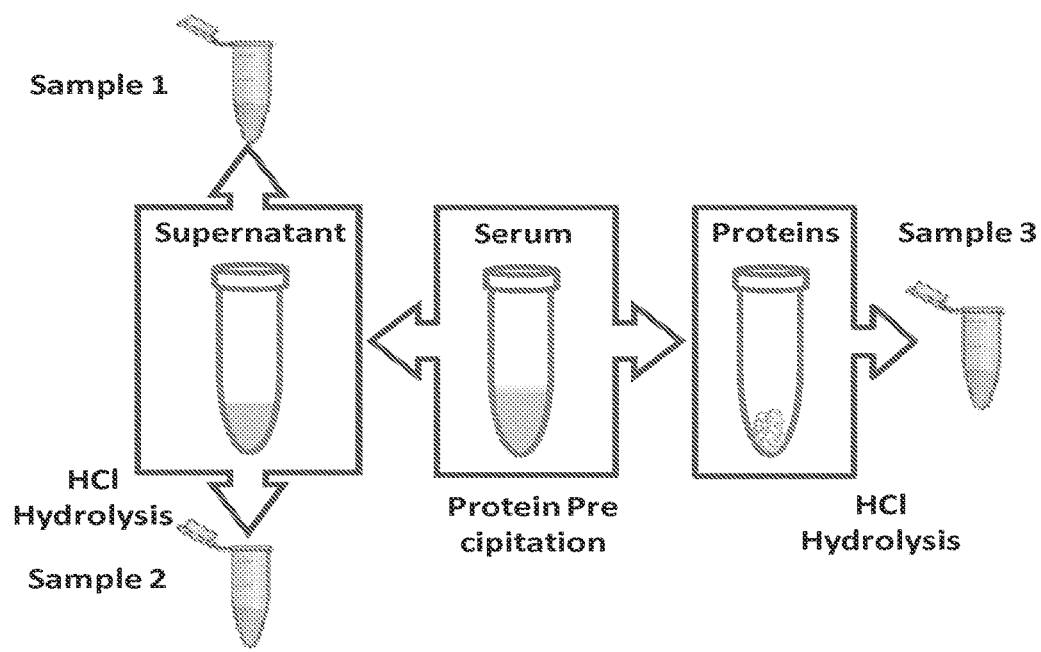
FIG. 2. A schematic illustration of sample preparation to obtain amino acids in the three domains from a single serum sample, including FAAs (Sample 1), FAASPAAs (Sample 2), and PAAs (Sample 3).

In this study, we obtained 3 amino acid samples from each serum aliquot for further LC-MS/MS experiments. FIG. 2 illustrates how amino acids were obtained from the three domains using a single serum sample, including the portions for measuring FAAs (Sample 1), FAASPAAs (Sample 2), and PAAs (Sample 3). We mixed 30 uL serum and 300 uL methanol in a 1.5 mL Micro tube with the safe screw cap (preferred for high temperature acid hydrolysis, Sarstedt Inc., Newton, N.C.), and then vortexed the mixture for 10 min. The mixture was incubated at 4° C. for 20 min and then centrifuged at 13,000 rpm for 5 min to precipitate the proteins. The supernatant was collected into a new vial. To the protein pellet, we added 660 uL methanol:DI water (10:1, v:v), which was then vortexed for 10 min. After centrifuging at 13,000 rpm for 5 min, the supernatant was added to the previous vial. The combined supernatant was dried under vacuum using an Eppendorf Vacufuge (Eppendorf, Hauppauge, N.Y.) and then reconstituted in 60 uL DI water. The first half (30 uL) of the sample was mixed with 120 uL DI water and used as Sample 1. The other half (30 uL) of the sample was mixed with 500 uL 6N HCl and baked at 110° C. using a digitally controlled dry bath (Labnet International, Inc., Edison, N.J.) for 24 hrs. This sample was then dried and reconstituted in 150 uL DI water prior to LC-MS/MS analysis to prepare Sample 2. In addition, the protein pellet was suspended in 500 uL 6N HCl and incubated at 110° C. for 24 hrs to prepare Sample 3. Then Sample 3 was dried and reconstituted in the same way as that for Sample 2 except that it was diluted 50-fold with DI water.

LC-MS/MS Measurements

All experiments were performed using an Agilent 1260 LC-6410 Triple Quad MS system (Agilent Technologies, Inc., Santa Clara, Calif.). The injection volumes for Sample 1, Sample 2, and Sample 3 were 9, 3, and 3 uL, respectively, to ensure that the MS intensities were within the dynamic range of the instrument. The LC separation was carried out on an Agilent Eclipse XDB-C18 (100×3 mm, 1.8 um) column. The flow rate was 0.5 mL/min. Mobile phase A was 0.2% formic acid in $H_2O$, and mobile phase B was 0.2% formic acid in acetonitrile. For each run, the content of mobile phase A was kept constant at 97% for the first 1 min, and then decreased to 10% during the next 4 min. After that gradient, the mobile phase A content was kept at 10% for 4 min until the end of gradient (a total of 9 min). The MS spectrometer was operated under the multiple reaction monitoring (MRM) mode using positive (+) ionization. $^{13}C_2$-tyrosine (6.72 uM) was spiked into all samples for monitoring to ensure that the machine was working well. The MS conditions were optimized for the best signal responses and peak quality using the amino acid standards; Table 3 shows the optimized MS parameters to measure amino acids in this study.

TABLE 3

The optimized MS parameters to measure amino acids

| Amino Acid | Precursor Ion | Product Ion | CE | Fragmentor | Accelerator voltage |
|---|---|---|---|---|---|
| isoleucine/leucine[a] | 132.1 | 86.1 | 10 | 80 | 1 |
| valine | 118.2 | 72.2 | 10 | 80 | 1 |
| glutamine[b] | 147.1 | 83.8 | 20 | 80 | 1 |
| glutamic acid | 148.0 | 84.2 | 15 | 80 | 1 |
| tryptophan | 205.1 | 118.0 | 25 | 80 | 5 |
| proline | 116.1 | 70.2 | 15 | 80 | 1 |
| threonine | 120.1 | 74.2 | 10 | 80 | 1 |
| histidine | 156.1 | 110.0 | 10 | 80 | 5 |
| alanine | 90.1 | 43.9 | 10 | 60 | 1 |
| serine | 105.9 | 60.1 | 10 | 60 | 1 |
| aspartic acid | 133.9 | 74.0 | 15 | 80 | 1 |
| tyrosine | 182.1 | 136.1 | 10 | 80 | 3 |
| methionine | 150.0 | 104.1 | 10 | 80 | 1 |
| cysteine[c] | 121.8 | 75.9 | 15 | 140 | 1 |
| lysine[b] | 147.0 | 84.1 | 15 | 80 | 7 |
| phenylalanine | 166.1 | 120.1 | 10 | 80 | 5 |
| arginine | 175.1 | 70.2 | 25 | 80 | 1 |
| asparagine | 132.9 | 74.0 | 15 | 80 | 1 |
| glycine | 76.2 | 29.9 | 10 | 60 | 1 |

[a]Isoleucine and leucine have the same optimized MS parameters.
[b]Glutamine and lysine have different but very similar optimized MS parameters. In this study, they were measured separately, but they were combined for data analysis.
[c]We could not obtain a good sensitivity or peak shape for cysteine; therefore, it was excluded from analysis in this study.

Data Analysis

The Agilent MassHunter QQQ Quantitative Analysis software (version B.03.01) was used to extract MS peak areas. The integrated areas of amino acids in each batch (3 batches in total) were normalized to the average of those in the quality control (QC) sample (4 injections in each batch) and then the BCA assay values. Similar to previous studies (Ma et al. 2004; Okamoto et al. 2009; Asiago et al. 2010; Leichtle et al. 2012; Nishiumi et al. 2012), we used penalized logistic regression to construct multivariate statistical models based on amino acid levels measured in the three domains, both individually and in combination. The R statistical software (version 2.8.0) was installed with the glmpath package for penalized logistic regression calculations (Park and Hastie 2007). Ten-fold cross validation was used for model building. The output of this procedure was a ranked set of markers according to the prediction probability of validation samples (some less important variables could be omitted) (Chen and Dey 2003; Bursac et al. 2008; Kiezun et al. 2009). Thereafter, logistic regression was used to build a predictive model based on the selected variables. The verification package installed in R was used to generate receiver operating characteristic (ROC) curves, and to calculate the sensitivity, specificity, and the AUROC of the statistical models.

Results and Discussion

LC-MS/MS

Figures 3A, 3B:
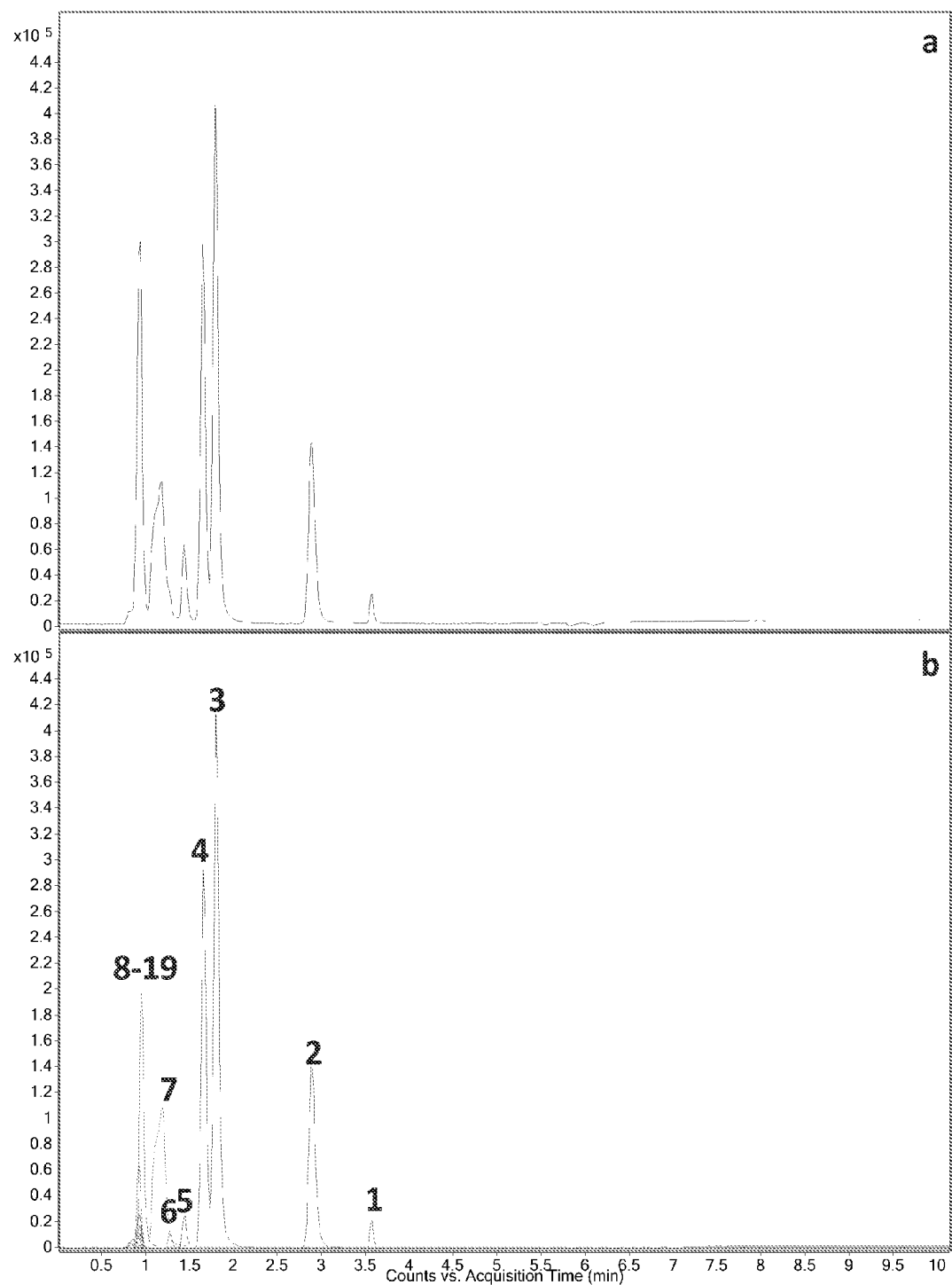
FIGS. 3A-3B.

FIG. 3a shows the total ion chromatogram (TIC) of the LC-MS/MS data of FAAs (Sample 1) from a typical serum sample, and FIG. 3b shows the extracted ion chromatogram (EIC) of FIG. 3a. While 12 amino acids were overlapped (~0.9 min), 7 amino acids were separated in the EIC (FIG. 3b), including tryptophan, phenylalanine, leucine, isoleucine, tyrosine, methionine, and valine. We could not obtain good sensitivity or peak shape for cysteine, and therefore it was excluded from the analysis in this study. Isoleucine and leucine had the same optimized MS parameters (Table 3), and they could not be base-line separated in the LC separation (FIG. 3b). Glutamine and lysine had different optimized MS parameters (Table 3), but our analytical assay could not differentiate them either (they co-eluted together and the MS spectrometer had unit resolution). Therefore, we obtained 17 variables from the LC-MS/MS measurements of the FAA profile (Sample 1), after adding isoleucine/leucine and glutamine/lysine together, respectively. In addition, during HCl hydrolysis tryptophan was completely destroyed, and asparagine was completely hydrolyzed to aspartic acid. Glutamine became glutamic acid, in which case lysine could be separately measured. Thus, we had 15 LC-MS/MS variables from Sample 2 (FAASPAAs) and Sample 3 (PAAs).

Amino Acids

Table 2 shows the amino acids in the three domains with significant differences (Student's T-Test P values less than 0.05) when comparing the colon cancer patients and healthy controls. Notably, the average coefficient of variation (CV) of the amino acid measurements for 12 injections of the QC sample (4 injections in each of the 3 batches) was 3.7%, ranging from 2.0% (alanine) to 10.4% (tryptophan). As shown in Table 2, there were 10, 9, and 14 amino acids with low P values (<0.05) in FAAs (Sample 1), FAASPAAs (Sample 2), and PAAs (Sample 3), respectively. Histidine in FAAs had the lowest P value of 0.00013; in general, FAASPAAs had higher P values than FAAs and PAAs. Interestingly, glutamic acid/glutamine/lysine, histidine, isoleucine/leucine, threonine, and valine were changed significantly in all the three domains; asparagine/aspartic acid (FAAs and PAAs), methionine (FAAs and FAASPAAs), serine (FAASPAAs and PAAs), and tyrosine (FAASPAAs and PAAs) were altered in two profiles. The relative intensities of histidine in FAAs to those in PAAs were more affected by colon cancer, with a fold change of 0.85 (cancer/control), than the relative intensities of histidine in FAASPAAs (fold change, 0.98). This indicates that colon cancer not only changes amino acids individually in metabolism, peptides, or proteins, but also affects the amino acid distribution in these domains.

TABLE 2

Amino acids in the three domains with P values <0.05 when comparing colon cancer patients and healthy controls.

| Amino Acid | P Values |
|---|---|
| FAAs (sample 1) | |
| asparagine | 0.031 |
| aspartic acid | 0.018 |
| glutamic acid | 0.032 |
| glutamine/lysine | 0.0045 |
| histidine | 0.00013 |
| isoleucine/leucine | 0.026 |
| methionine | 0.0050 |
| threonine | 0.042 |
| tryptophan | 0.044 |
| valine | 0.0078 |
| FAASPAAs (sample 2) | |
| glutamic acid/glutamine | 0.015 |
| histidine | 0.042 |
| isoleucine/leucine | 0.010 |

TABLE 2-continued

Amino acids in the three domains with P values <0.05 when comparing colon cancer patients and healthy controls.

| Amino Acid | P Values |
| --- | --- |
| lysine | 0.0017 |
| methionine | 0.036 |
| serine | 0.022 |
| threonine | 0.0041 |
| tyrosine | 0.023 |
| valine | 0.0032 |
| PAAs (sample 3) | |
| alanine | 0.00099 |
| arginine | 0.00089 |
| aspartic acid/asparagine | 0.0045 |
| glutamic acid/glutamine | 0.0016 |
| glycine | 0.048 |
| histidine | 0.0022 |
| isoleucine/leucine | 0.0013 |
| lysine | 0.00066 |
| phenylalanine | 0.00037 |
| proline | 0.0071 |
| serine | 0.014 |
| threonine | 0.0057 |
| tyrosine | 0.00042 |
| valine | 0.0094 |

Logistic Regression Analysis

Figures 4A, 4B, 4C, 4D:
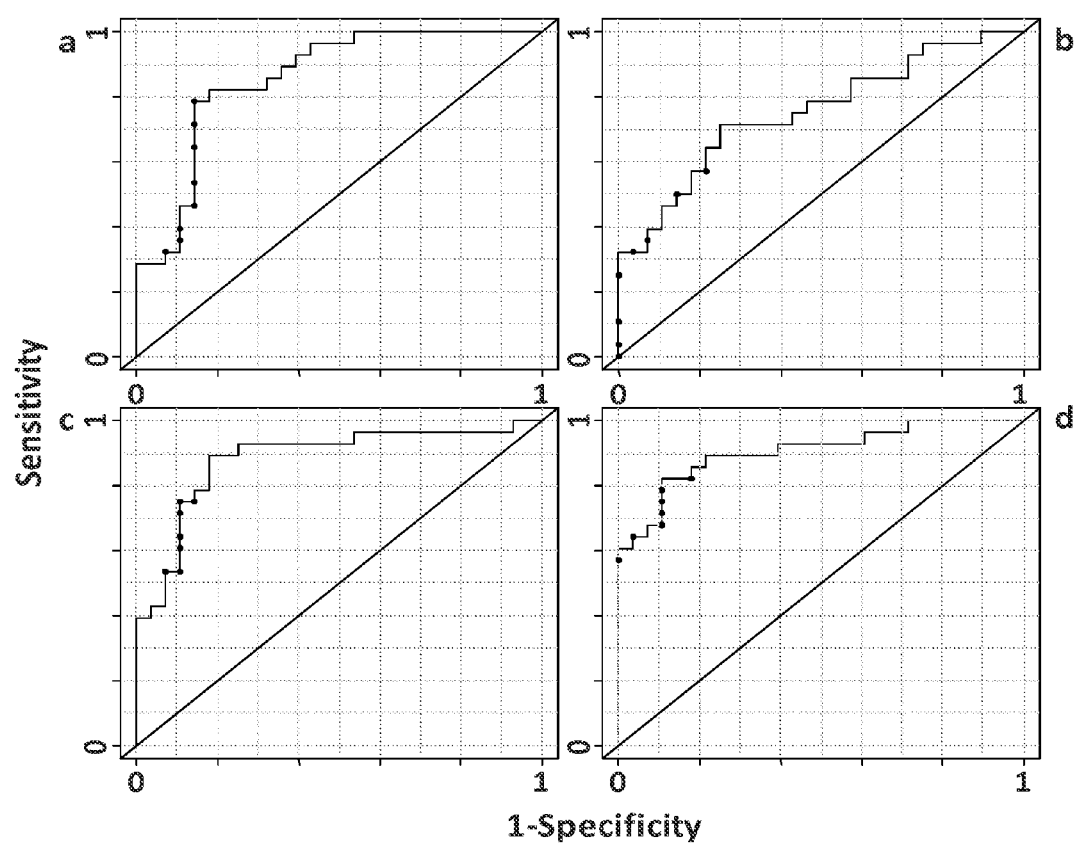
FIGS. 4A-4D. The ROC curves of the penalized logistic regression models based on the amino acids with P values less than 0.05. (4A) FAAs, (4B) FAASPAAs, (4C) PAAs, and (4D) the selected amino acids by penalized logistic regression using all three sample types.

To improve the performance and reliability in the statistical modeling, we further constructed penalized logistic regression models based on the amino acids in Table 2 (P values<0.05). We first individually examined the performance of amino acids in different domains for detecting colon cancer patients. FIG. 4a shows the ROC curve for the logistic regression model using the FAAs (Sample 1). This model had an AUROC of 0.86. The sensitivity was 28% when the specificity was 95%. Penalized logistic regression selected 4 important variables from 10 candidates (FAAs in Table 2), including aspartic acid, glutamic acid, glutamine/lysine, and histidine.

Similarly, FIG. 4b shows the ROC curve for the penalized logistic regression model based on the FAASPAAs (Sample 2) in Table 2. An AUROC of 0.75 was obtained, which was less than that (0.86) in FIG. 4a. The sensitivity was 32% (>28% in FIG. 4a) when the specificity was 95%. The selected amino acids from the 9 FAASPAAs were lysine and valine. FIG. 4c shows the ROC curve for the penalized logistic regression model based on the 14 PAAs (Sample 3) in Table 2, and the AUROC was determined to be 0.88. The significant amino acids included alanine, arginine, aspartic acid/asparagine, glycine, proline, serine, threonine, tyrosine, and valine. This model (FIG. 4c) had a better performance to differentiate colon cancer than that in FIGS. 4a and 4b, especially when the specificity was between 80%-100%. For example, the sensitivity was 43% (compared to 28% and 32% in FIGS. 4a and 4b, respectively) when the specificity was 95%.

Figure 5A:
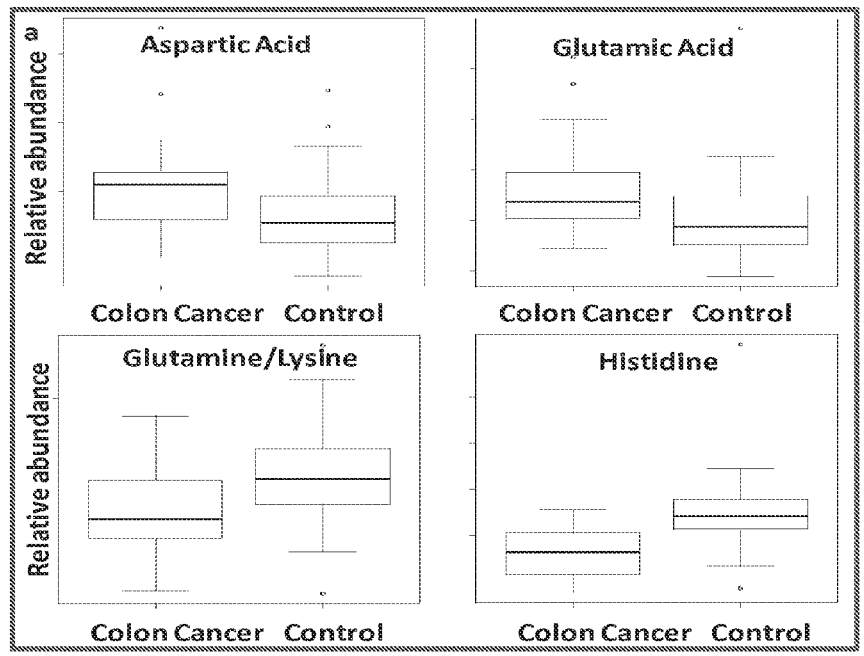
FIGS. 5A-5C. Box-and-whisker plots for the amino acid markers in constructing the model in FIG. 4D. (5A) aspartic acid, glutamic acid, glutamine/lysine, and histidine from FAAs, (5B) lysine from FAASPAAs, and (5C) arginine, serine, and tyrosine from PAAs.
Figure 5B:
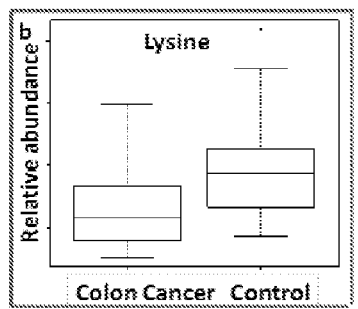
Figure 5C:
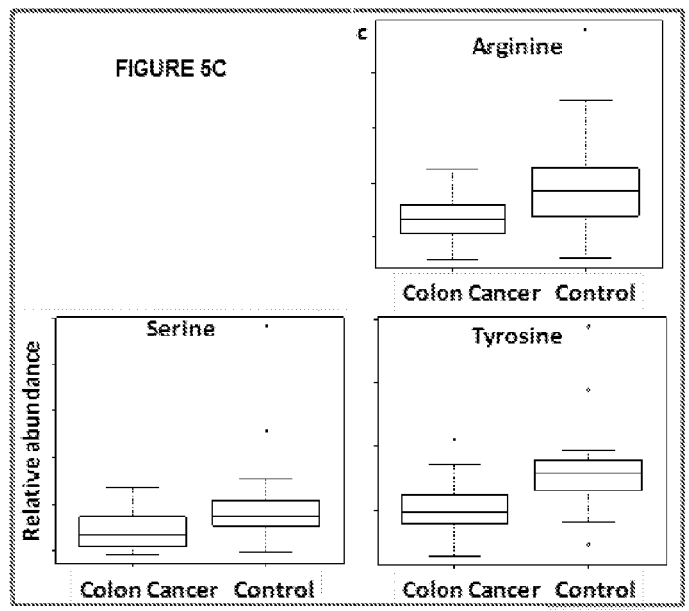

Furthermore, we performed penalized logistic regression on the selected variables from the 3 models above. An AUROC of 0.91 was achieved for the ROC curve in FIG. 4d. In particular, this model had a sensitivity of 65% when the specificity was 95%. The important amino acids selected in FIG. 4d were aspartic acid, glutamic acid, glutamine/lysine, and histidine from FAAs (4 out of 4 variables), lysine from FAASPAAs (1 out of 2 variables), and arginine, serine, and tyrosine from PAAs (3 out of 9 variables). FIG. 5 shows the box-and-whisker plots for the amino acid marker candidates in constructing the model shown in FIG. 4d. Aspartic acid and glutamic acid in FAAs were increased in the colon cancer patients, while the rest of amino acids were decreased. This further confirmed that the distribution of amino acids in the three domains was altered under the biological stress of colon cancer.

Figure 6:
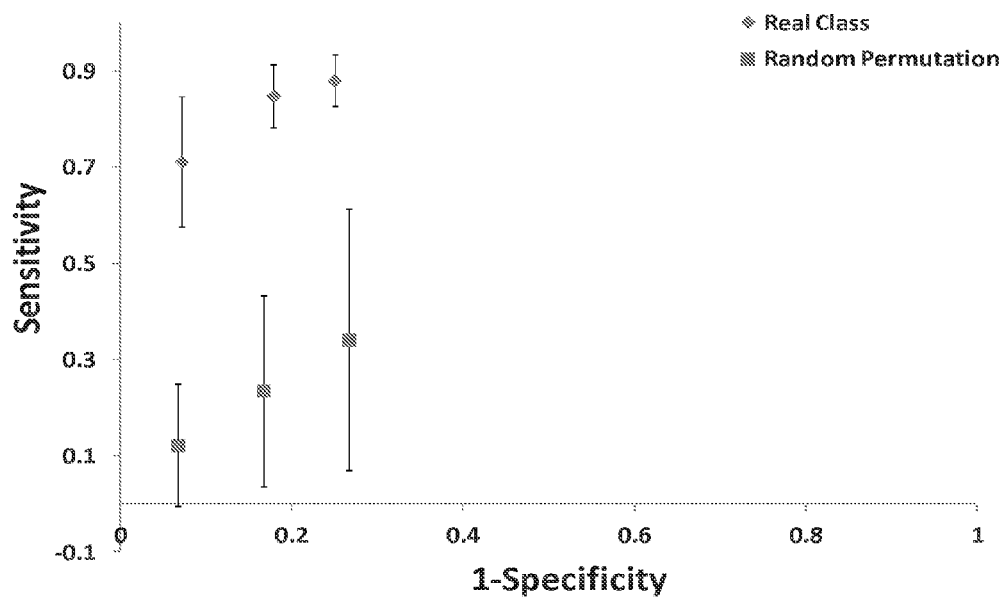
FIG. 6. MCCV of the penalized logistic regression model of FIG. 4D in a ROC space. True class models, blue diamonds; random permutation models, brown squares.

To further evaluate the reliability and consistence of statistical modeling, we used Monte Carlo Cross Validation (MCCV) (Rocha et al. 2011; Wei et al. 2012) to validate the penalized logistic regression model in FIG. 4d. In each iteration (100 total), all the samples were randomly divided into two sets, 70% as the training set and 30% as the test set. Penalized logistic regression was performed on the training set, and then the resulting model was used to predict the classification of the test set samples. The sample membership could be either correctly assigned, referred as true class, or randomly assigned (permutation). FIG. 6 shows the sensitivities at the specificities of 0.95, 0.85, and 0.75, respectively, for the true class models and permutation models in a ROC space. The true class models were clearly separated from the permutation models, with significantly higher sensitivities. For example, the average sensitivity of true class models was 71% (±14%) at the highest selected specificity, while it was 12% (±13%) for the permutation models. This testified to the fact that amino acids from the three domains in the serum samples contain variations related to colon cancer.

It is well known that colon cancer leads to alterations in amino acid metabolism, and amino acids have been recognized in metabolomics as putative markers for diagnosing colon cancer (Tan et al. 2013). Nishiumi et al. found that the gas chromatography-MS (GC-MS) intensities of aspartic acid and glutamic acid were increased in CRC serum samples while the glutamine and lysine intensities were decreased (Nishiumi et al. 2012), which fits well with our results (FIG. 5). Their logistic regression model based on 4 markers including aspartic acid achieved higher diagnosis accuracy (85%) than that by CEA (66%) or CA 19-9 (58%). Aspartic acid is produced from oxaloacetate by transamination, and an increased serum level of aspartic acid may indicate that tumor cells need more nutrient uptake (Heber et al. 1985). Cancer cells require a higher consumption of glutamine for both energy and biosynthetic purposes (DeBerardinis et al. 2007; Wise et al. 2008; Heiden et al. 2009), and the observed complementary changes of glutamic acid (increased) and glutamine (decreased) suggest that glutamine synthetase may be associated with colon cancer. Okamoto et al. also discovered that glutamic acid was significantly increased in colon cancer plasma samples and histidine was decreased, although with less significance (Okamoto et al. 2009). However, some inconsistencies were observed among our study and previous research as well. For example, Nishiumi et al. found an increased level of histidine in CRC sera (Nishiumi et al. 2012), and Tan et al. obtained lower levels of glutamate and aspartate in CRC serum samples using GC-time of flight (TOF)-MS and LC-TOF-MS (Tan et al. 2013). Leichtle et al. found 11 serum amino acids that were significantly different between colon cancer patients and healthy controls, and they built a statistical model based on CEA, glycine, and tyrosine (Leichtle et al. 2012). Therefore, as suggested by Kimura et al. (Kimura et al. 2009), it might be necessary to evaluate the network of amino acids in metabolism, peptides, and proteins (FIG. 1) in order to gain a deeper understanding of these phenomena.

Proteomics is complementary to metabolomics in systems biology, and colon cancer induces altered protein synthesis/degradation (Heber et al. 1985). Carcinogenesis of colorectal cancer is a complex process involving multiple genetic abnormalities such as mutations in both tumor suppressor genes and oncogenic mediators (Fearon and Vogelstein 1990; Markowitz and Bertagnolli 2009; Noffsinger 2009; Nambiar et al. 2010). An important consequence of this complex progression could be the altered uptake and usage of amino acids. SILAC is used to study the incorporation of amino acids and degradation of proteins; however, the analysis of individual amino acids composing proteins/peptides has rarely been combined with those in metabolism. In this semi-quantitative study, it was demonstrated that colon cancer changed the amino acid domains of FAASPAAs and PAAs (Table 2). More importantly, the distribution of amino acids was changed among isolated metabolites, peptides, and proteins. In addition, the combined analysis of amino acids in the three domains helped improve the diagnostic power of logistic regression modeling to detect colon cancer (FIG. 4 and FIG. 6).

While an improved logistic regression model was obtained after incorporating amino acids in peptides and proteins, our approach does not provide the ability to identify specific proteins/peptides related to colon cancer. Many amino acids underwent some degree of loss during hydrolysis; therefore, in this semi-quantitative study we prepared the samples using the same and traditional hydrolysis method (incubation in HCl under 110° C. for 24 hrs). Correction factors can be employed if a precise quantification is desired (Robel and Cranea 1972; Fountoulakis and Lahm 1998). In principle, stable isotope-resolved metabolomics (SIRM) (Fan and Lane 2011; Lane et al. 2011) and SILAC (Ong et al. 2002; Pratt et al. 2002; Mann 2006; Schmidt et al. 2007; Marimuthu et al. 2013) can quantitatively track the distribution of each amino acid in different domains (FIG. 1). We measured 168 samples (FAAs, FAASPAAs, and PAAs) from 56 subjects, which limited our ability to perform analyses related to other important factors such as cancer stage. External cross validation with a separate test set using additional subjects is planned to further validate the statistical models.

Conclusions

This is the first study to perform a combined analysis of amino acids in the three domains of FAAs, FAASPAAs, and PAAs. We used acid hydrolysis to obtain individual amino acids from peptides and proteins, and LC-MS/MS was utilized to measure the serum samples from colon cancer patients and healthy controls. It was shown that colon cancer changed the amino acid profiles and their relative distribution in these three domains. Furthermore, the combined analysis helped improve the sensitivity and specificity of the penalized logistic regression model for detecting colon cancer. The significant amino acids were selected to be aspartic acid, glutamic acid, glutamine/lysine, and histidine from FAAs, lysine from FAASPAAs, and arginine, serine, and tyrosine from PAAs. This study directly connects metabolism and proteome through the measurement of individual amino acids, and it potentially brings new insights to the diagnosis and mechanistic studies of colon cancer.

References Cited in Example 1

Aebersold R, Mann M (2003). Nature 422(6928): 198-207.
Asiago V M, et al (2010). Cancer Res 70(21): 8309-8318.
Bain J R, et al. (2009). Diabetes 58(11): 2429-2443.
Burkard T R, et al (2011). BMC Syst Biol 5.
Bursac Z, et al (2008). Source Code Biol Med 3: 17.
Cai Z, et al (2010). Mol Cell Proteomics 9(12): 2617-2628.
Casado-Vela J, et al (2011). Clin Transl Oncol 13(9): 617-628.
Chan E C Y, et al (2009). J Proteome Res 8(1): 352-361.
Chen M H, Dey D K (2003). J Stat Plan Inference 111(1-2): 37-55.
DeBerardinis R J, et al (2007). Proc Natl Acad Sci USA 104(49): 19345-19350.
Denkert C, et al (2008). Mol Cancer 7.
Fan T W M, Lane A N (2011). N J Biomol NMR 49(3-4): 267-280.
Fearon E R, Vogelstein B (1990). Cell 61(5): 759-767.
Fountoulakis M, Lahm H W (1998). J Chromatogr A 826(2): 109-134.
Goss K H, Groden J (2000). J Clin Oncol 18(9): 1967-1979.
Gowda G A N, Z et al (2008). Expert Rev Mol Diagn 8(5): 617-633.
Gu H, et al (2012). Future Oncol 8(10): 1207-1210.
Heber D, et al (1985). Cancer 55(1): 225-229.
Heiden M G V, et al (2009). Science 324(5930): 1029-1033.
Hockenbery D M (2010). Environ Mol Mutag 51(5): 476-489.
Jain M, et al (2012). Science 336(6084): 1040-1044.
Kiezun A, et al (2009). Bioinformation 3(7): 311-313.
Kim J, Dang C V (2006). Cancer Res 66(18): 8927-8930.
Kimura T, et al (2009). Curr Opin Clin Nutr Metab Care 12(1): 49-53.
Lane A N, et al (2011). OMICS: J Integrative Biol 15(3): 173-182.
Lean C L, et al (1993). Magn Reson Med 30(5): 525-533.
Leichtle A B, et al (2012). Metabolomics 8(4): 643-653.
Ma J, et al (2004). J Natl Cancer Inst 96(7): 546-553.
Mann M (2006). Nat Rev Mol Cell Biol 7(12): 952-958.
Marimuthu A, et al (2013). Proteomics Clin Appl 7(5-6): 355-366.
Markowitz S D, Bertagnolli M M (2009). New Engl J Med 361(25): 2449-2460.
Miyagi Y, et al (2011). Plos One 6(9).
Monleon D, et al (2009). NMR Biomed 22(3): 342-348.
Nambiar P R, et al (2010). Mutat Res-Fundam Mol Mech Mutag 693(1-2): 3-18.
Nicholson J K, et al (2012). Nature 491(7424): 384-392.
Nishiumi S, et al (2012). PLoS ONE 7(7): e40459.
Noffsinger A E (2009). Annu Rev Pathol-Mech 4: 343-364.
O'Dwyer D, et al (2011). Plos One 6(11).
Okamoto N, et al (2009). Int J Med Sci 1(1): 1-8.
Ong S E, et al (2002). Mol Cell Proteomics 1(5): 376-386.
Pandey A, Mann M (2000). Nature 405(6788): 837-846.
Park M Y, Hastie T (2007). J R Stat Soc Ser B Stat Methodol 69: 659-677.
Piotto M, et al (2009). Metabolomics 5(3): 292-301.
Pratt J M, et al (2002). Mol Cell Proteomics 1(8): 579-591.
Qiu Y P, et al (2010). J Proteome Res 9(3): 1627-1634.
Qiu Y P, et al (2009). J Proteome Res 8(10): 4844-4850.
Randhawa H, et al (2013). BMC Cancer 13.
Reaves M L, Rabinowitz J D (2011). Curr Opin Biotechnol 22(1): 17-25.
Ritchie S A, et al (2010). Bmc Medicine 8.
Robel E J, Cranea A B (1972). Anal Biochem 48(1): 233-246.
Rocha CuM, et al (2011). J Proteome Res 10(9): 4314-4324.
Samudio I, et al (2009). Cancer Res 69(6): 2163-2166.
Scalbert A, et al (2009). Metabolomics 5(4): 435-458.
Schmidt F, et al (2007). Rapid Commun Mass Spectrom 21(23): 3919-3926.
Siegel R, et al (2013). CA-Cancer J Clin 63(1): 11-30.
Tan B B, et al (2013). J Proteome Res 12(6): 3000-3009.
Warburg O (1956). Science 123(3191): 309-314.
Wei S, et al (2012). Metabolites 2(4): 701-716.
Weston A D, Hood L (2004). J Proteome Res 3(2): 179-196.

Wise D R, et al (2008). Proc Natl Acad Sci USA 105(48): 18782-18787.

Yanes O, et al (2011). Anal Chem 83(6): 2152-2161.

Example 2: Colorectal Cancer Detection Using Targeted Serum Metabolic Profiling

In this example, a targeted liquid chromatography-tandem mass spectrometry-based metabolic profiling approach was employed for identifying biomarker candidates that could enable highly sensitive and specific CRC detection using human serum samples. 158 metabolites from 25 metabolic pathways of potential significance were monitored. 234 serum samples from three groups of patients (66 CRC patients, 76 polyp patients, and 92 healthy controls) were analyzed. Partial least squares-discriminant analysis (PLS-DA) models were established, which proved to be powerful for distinguishing CRC patients from both healthy controls and polyp patients in this study. Receiver operator characteristic curves generated based on these PLS-DA models showed high sensitivities (0.96 and 0.89, respectively, for differentiating CRC patients from healthy controls or polyp patients), good specificities (0.80 and 0.88), low false discovery rates (0.22 and 0.14), and excellent areas under the curve (0.93 and 0.95) were obtained. Monte Carlo cross validation (MCCV) was also applied, demonstrating the robust diagnostic power of this metabolic profiling approach.

Materials and Methods

Clinical Samples:

Patient recruitment and sample collection protocols were approved by the Purdue University and Indiana University School of Medicine Institutional Review Boards. Informed consent was provided from all subjects in the study according to institutional guidelines. Patients undergoing colonoscopy for CRC screening were evaluated, and blood samples from the patients were obtained after overnight fasting and bowel preparation prior to colonoscopy. In total, 234 subjects were recruited in this study, and they were grouped into CRC patients (n=66), polyp patients (n=76), and healthy controls (n=92) based on the analysis of biopsied tissue. Patients were age and gender matched in each group. All serum samples were from patients without any intervention/treatment. All the CRC patients in this study were newly diagnosed, and the blood samples were drawn before any surgery, chemotherapy, or radiation treatment. Patients' demographical and clinical information is shown in Table 4. Each blood sample was allowed to clot for 45 min and then centrifuged at 2000 rpm for 10 min. All samples were stored in −80° C. freezer until experiments.

TABLE 4

Summary of clinical and demographic characteristics of human subjects

| | | Total n = 234 | CRC n = 66 | Polyps n = 76 | Healthy Control n = 92 |
|---|---|---|---|---|---|
| Age | Median | | 58 | 56 | 57 |
| | Min | | 27 | 37 | 18 |
| | Max | | 88 | 86 | 80 |
| Gender | Male | | 30 | 37 | 45 |
| | Female | | 36 | 39 | 47 |
| Cancer stage | Stage I/II | | 21 | — | — |
| | Stage III | | 17 | — | — |
| | Stage IV | | 28 | — | — |
| Diagnosis | Colon Cancer | | 39 | — | — |
| | Rectal Cancer | | 27 | — | — |

Reagents:

Acetonitrile, ammonium acetate, and acetic acid (LC-MS grade) were all purchased from Fisher Scientific (Pittsburgh, Pa.). Standard compounds corresponding to the measured metabolites (see list in Table S1 available online as Supporting Information for Zhu et al., J. Proteome Res., 2014, 13 (9): 4120-4130) were purchased from Sigma-Aldrich (Saint Louis, Mo.) or Fisher Scientific (Pittsburgh, Pa.). Stable isotope-labeled tyrosine and lactate internal standards (L-tyrosine-$^{13}C_2$ and sodium-L-lactate-$^{13}C_3$) were purchased from Cambridge Isotope Laboratories, Inc. (Tewksbury, Mass.). The purities of non-labeled standards were >95-99% whereas the purities of the two $^{13}C$ labeled compounds were >99%.

Sample Preparation:

Frozen samples were first thawed at room temperature for approximately 45 min, and 50 μL of each serum was placed into a 2 mL Eppendorf vial (Fisher Scientific). The initial step for protein precipitation and metabolite extraction was performed by adding 150 μL of methanol; the mixture was the vortexed for 2 min and stored at −20° C. for 20 min. Next, the sample was centrifuged at 14,000 rpm for 10 min, and the supernatant was collected into a new Eppendorf vial. To the first vial containing the pellet, another 300 μL methanol was added, and the mixture was vortexed for 10 min to allow thorough metabolite extraction. After centrifuging this mixture at 14,000 rpm for 10 min, the supernatant was collected into the same vial that contained the previous supernatant. The resulting supernatants from two rounds of extractions were dried using a Vacufuge Plus evaporator (Eppendorf, Hauppauge, N.Y.). The dried samples were stored at −20° C., and were reconstituted in 500 μL 5 mM ammonium acetate in 40% water/60% acetonitrile+0.2% acetic acid containing 5.13 μM L-tyrosine-$^{13}C_2$ and 22.54 μM sodium-L-lactate-$^{13}C_3$ (Cambridge Isotope Laboratory). The two isotope-labeled internal standards were added to each sample to monitor the system performance. The samples were filtered through 0.45 μm PVDF filters (Phenomenex, Torrance, Calif.) prior to LC-MS analysis. A pooled sample, which was a mixture of serum from CRC patients, polyp patients, and healthy controls, was extracted using the same procedure as above. This sample was used as the quality control (QC) sample and was analyzed once for every ten patient samples.

Liquid Chromatography Conditions:

The LC system was composed of two Agilent 1260 binary pumps, an Agilent 1260 auto-sampler, and Agilent 1290 column compartment containing a column-switching valve (Agilent Technologies, Santa Clara, Calif.). Each sample was injected twice, 10 μL for analysis using negative ionization mode and 2 μL for analysis using positive ionization mode. Both chromatographic separations were performed in hydrophilic interaction chromatography (HILIC) mode on two SeQuant ZIC-cHILIC columns (150×2.1 mm, 3.0 μm particle size, Merck KGaA, Darmstadt, Germany) connected in parallel. Our setup allows one column to perform the separation while the other column is reconditioned and readied for the next injection. The flow rate was 0.300 mL/min, the auto-sampler temperature was kept at 4° C., the column compartment was set at 40° C., and total separation time for both ionization modes was 20 min. The mobile phase was composed of Solvents A (5 mM ammonium acetate in 90% $H_2O$/10% acetonitrile+0.2% acetic acid) and B (5 mM ammonium acetate in 90% acetonitrile/10% $H_2O$+0.2% acetic acid). The gradient conditions for both separations were identical and are shown in Table 7.

TABLE 7

LC Gradient Conditions.

| Time Segment, min. | Solvent A, % | Solvent B, % |
|---|---|---|
| 0-2 | 25 | 75 |
| 2-5 | from 25 to 70 | from 75 to 30 |
| 5-9 | 70 | 30 |
| 9-11 | from 70 to 25 | from 30 to 75 |
| 11-20 | 25 | 75 |

The metabolite identities were confirmed by spiking the pooled serum sample used for method development with mixtures of standard compounds (each mixture contained five standard metabolites). However, some metabolites that could not be well separated and had similar m/z values (<1 Da) were integrated as single peaks (e.g., malonic acid and 3-hydroxybutyric acid were reported as a single peak). All the samples were analyzed over a 12-day period and the retention times (RT) did not undergo any significant shift (each peak was within 6 s throughout 12 days of analysis), which proved the robustness of our HILIC method.

Mass Spectrometry Conditions:

After the chromatographic separation, MS ionization and data acquisition were performed using an AB Sciex QTrap 5500 mass spectrometer (AB Sciex, Toronto, ON, Canada) equipped with an electrospray ionization (ESI) source. The instrument was controlled by Analyst 1.5 software (AB Sciex, Toronto, ON, Canada). Targeted data acquisition was performed in multiple-reaction-monitoring (MRM) mode. We monitored 99 and 59 MRM transitions in negative and positive mode, respectively (158 transitions in total). The source and collision gas was $N_2$ (99.999% purity). The ion source conditions in negative/positive mode were: curtain gas (CUR)=25 psi, collision gas (CAD)=high, ion spray voltage (IS)=−3.8/3.8 KV, temperature (TEM)=500° C., ion source gas 1 (GS1)=50 psi, and ion source gas 2 (GS2)=40 psi. The optimized MS compound conditions are shown in Table 51 available online as Supporting Information for Zhu et al., *J. Proteome Res.*, 2014, 13 (9): 4120-4130. The extracted MRM peaks were integrated using MultiQuant 2.1 software (AB Sciex).

Figure 13:
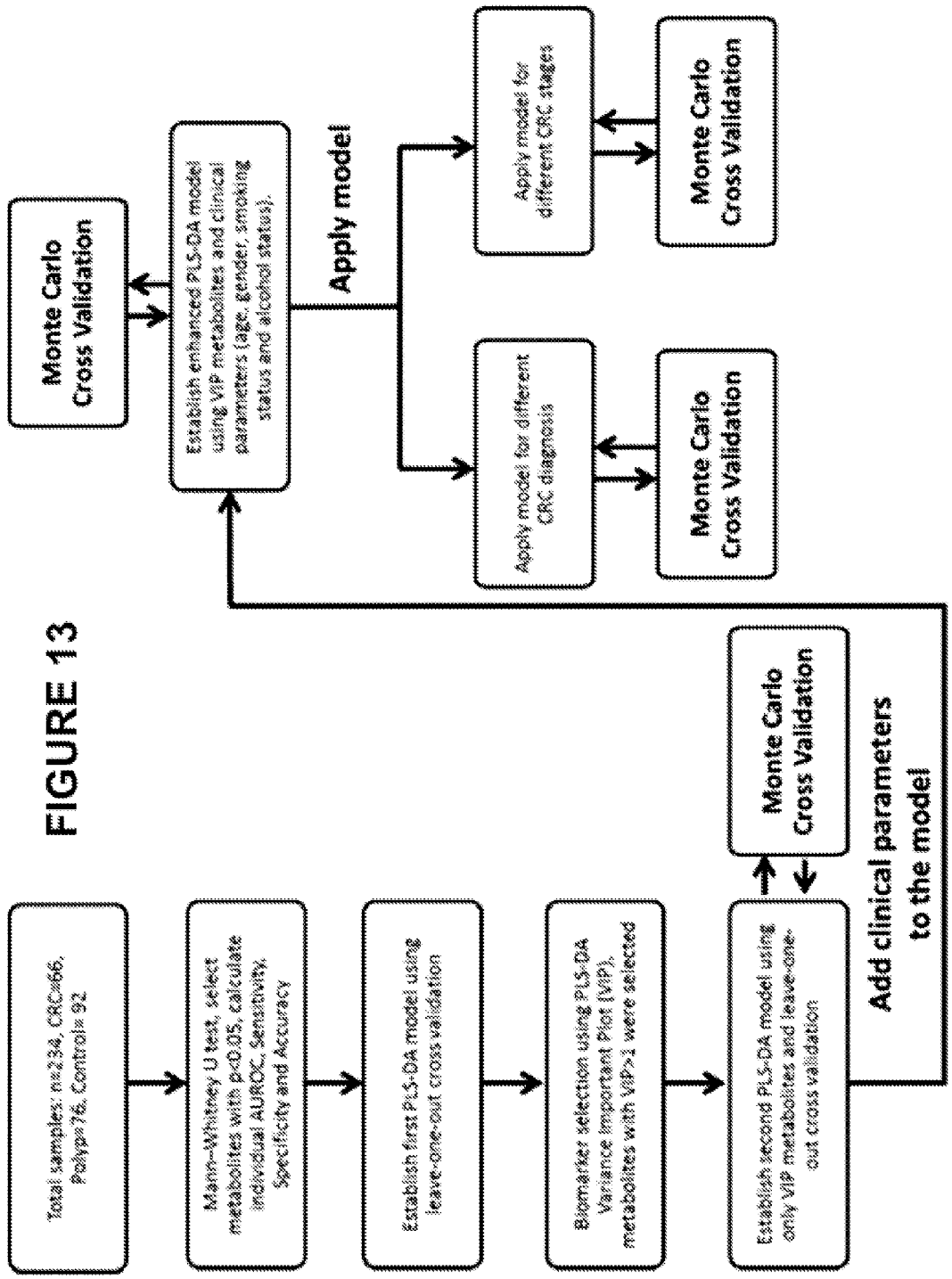
FIG. 13. Flow chart describing biomarker selection, model development, and validation.

Data Analysis, Model Development and Cross Validation:

In order to search for potential CRC diagnostic serum biomarkers, metabolite selection, model building, and cross validation were performed, and the data analysis steps are shown using a simplified flow chart shown in FIG. 13. After exporting from MultiQuant software, spectral data were normalized using average values from the data of QC injections (at least five in each batch, 33 QC samples in total). Mann Whitney U-tests, generation of receiver operator characteristics (ROC) curves, and calculation of sensitivity, specificity, and area under ROC curves (AUROC) were conducted using JMP Pro10 (SAS Institute). Partial least squares-discriminant analysis (PLS-DA) and Monte Carlo Cross Validation (MCCV, developed using in-house scripts) were performed using Matlab software (Mathworks, Natick, Mass.) installed with the PLS toolbox (Eigenvector Research Inc., Wenatchee, Wash.). MCCV was applied using 70% of the data as the training set while the remaining 30% served as the testing set, and employing 100 iterations. For each iteration three specificities of the training set, 0.95, 0.85, and 0.75, were used to determine the thresholds of PLS-DA predicted Y values. The same thresholds were then applied to the test set to determine sensitivities and specificities. The sample classification can be correctly assigned, termed "true class," or the sample class information can be randomly permuted, which is referred to as a "random permutation."

Results

Targeted Metabolic Profiles of CRC Vs. Polyp Patients and Health Controls:

In the current study, we used a targeted LC-MS/MS approach for comprehensive CRC serum metabolic profiling. Using this metabolic profiling system, we achieved targeted screening of 156 multiple reaction monitoring (MRM) transitions, for metabolites of 20 different chemical classes (such as amino acids, carboxylic acids, pyridines, etc.) and that are located in 25 important metabolic pathways (e.g., TCA cycle, amino acid metabolism, glycolysis, purine and pyrimidine metabolism, urea cycle) in both positive and negative ionization modes (see Table S1 available online as Supporting Information for Zhu et al., *J. Proteome Res.*, 2014, 13 (9): 4120-4130)). Two additional stable isotope labeled internal standards (L-tyrosine-$^{13}C_2$ and sodium-L-lactate-$^{13}C_3$) were also monitored to ensure instrument performance. In total, we detected 113 metabolites out of 158 targeted MRM transitions, with an average coefficient of variation (CV) of 11% (~80% metabolites have CV<15%). 42 of these metabolites showed statistical significance between CRC patients and healthy controls, 48 of them showing statistical difference between CRC and polyp patients, and 8 between healthy controls and polyp patients (Table 5) based on the Mann-Whitney U test with a p-value <0.05. Fold changes (FC) are also calculated based on mean ratios for CRC/Healthy, CRC/Polyps or Healthy/Polyps as appropriate. Eleven metabolites had p<0.001 (with FC ranging from 0.75 to 2.73) when comparing the CRC patients to healthy controls, and thirteen metabolites had p<0.001 (with FC ranging from 0.77 to 3.22) when comparing the CRC patients to polyp patients.

TABLE 5

P values and fold changes (FCs) for all potential metabolite biomarkers (with p < 0.05) based on Mann-Whitney U-test, 42 metabolites for comparison of cancer patients and healthy controls, 48 for comparison of cancer patients and polyp patients, and 8 for comparison of healthy controls and polyp patients.

| Metabolites (MRM transitions) | Cancer vs. Healthy | FC* | Cancer vs. Polyps | FC* | Healthy vs. Polyps | FC* |
|---|---|---|---|---|---|---|
| Oxalic Acid (89.0/61.0) | 2.00E−02 | 1.12 | | | 4.08E−02 | 0.92 |
| Glyceraldehyde (89.0/59.0) | 1.52E−05 | 1.34 | 2.19E−07 | 1.41 | | |
| gama-Aminobutyrate (102.1/85.0) | 1.75E−02 | 0.93 | 4.95E−03 | 0.91 | | |
| Malonic Acid/3HBA (103.0/59.0) | 3.47E−03 | 0.78 | | | | |
| Fumarate (115.0/71.0) | 4.34E−02 | 1.09 | 2.72E−02 | 1.07 | | |
| Maleic Acid (115.0/71.0 (2)) | 1.45E−03 | 1.13 | 1.96E−03 | 1.11 | | |
| N-AcetylGlycine (116.0/74.0) | 7.70E−04 | 0.75 | 1.71E−03 | 0.67 | | |
| Glutaric Acid (131.0/87.0) | | | 1.22E−02 | 1.05 | | |

TABLE 5-continued

P values and fold changes (FCs) for all potential metabolite biomarkers (with p < 0.05) based on Mann-Whitney U-test, 42 metabolites for comparison of cancer patients and healthy controls, 48 for comparison of cancer patients and polyp patients, and 8 for comparison of healthy controls and polyp patients.

| Metabolites (MRM transitions) | Cancer vs. Healthy | FC* | Cancer vs. Polyps | FC* | Healthy vs. Polyps | FC* |
|---|---|---|---|---|---|---|
| Oxaloacetate (131.0/87.0 (2)) | | | 4.46E−02 | 1.03 | 1.30E−02 | 1.05 |
| MethylSuccinate (131.0/113.0) | 4.60E−02 | 0.95 | 1.48E−02 | 0.94 | | |
| Aspartic Acid (132.0/88.0) | 1.40E−03 | 1.37 | 1.32E−03 | 1.39 | | |
| D-Leucic Acid (133.1/87.0) | 4.02E−02 | 1.46 | 2.07E−03 | 1.47 | | |
| 2-Oxoglutarate (145.0/101.0) | 5.71E−03 | 0.93 | 3.06E−03 | 0.93 | | |
| Allantoin (157.0/114.0) | 1.02E−03 | 1.24 | 2.58E−02 | 1.11 | | |
| 2-Aminoadipate (160.1/116.0) | 8.81E−03 | 0.86 | | | | |
| PEP (166.9/79.0) | 3.29E−02 | 0.89 | 3.68E−03 | 0.85 | | |
| Urate (167.0/124.0) | 1.40E−02 | 0.93 | 1.49E−02 | 0.93 | | |
| Homogentisate (167.0/123.0) | 1.59E−02 | 0.92 | 2.81E−02 | 0.93 | | |
| Glycerol-3-P (171.0/79.0) | | 0.98 | 2.32E−02 | 0.91 | | |
| Hippuric Acid (178.0/134.0) | 8.46E−05 | 2.73 | 1.40E−05 | 3.22 | | |
| Glucose (179.0/89.0) | 2.63E−02 | 1.08 | | | | |
| OH-Phenylpyruvate (179.0/107.0) | 4.34E−02 | 1.08 | | | | |
| Kynurenate (188.0/144.0) | 6.49E−03 | 1.16 | 1.01E−02 | 1.10 | | |
| Erythrose (199.0/97.0) | 3.53E−02 | 1.08 | | | | |
| Xanthurenate (204.0/160.0) | | | 3.19E−03 | 0.90 | 3.66E−02 | 0.95 |
| Pentothenate (218.1/88.0) | | | 3.11E−02 | 1.09 | | |
| Cystathionine (221.1/134.0) | 4.90E−03 | 1.45 | | | | |
| Biotin (243.1/200.0) | | | 1.01E−03 | 0.89 | 3.30E−03 | 0.91 |
| Margaric Acid (269.1/251.3) | | | 8.44E−03 | 0.91 | | |
| Linoleic Acid (277.1/259.0) | 2.71E−02 | 0.88 | 5.62E−03 | 0.83 | | |
| Linolenic Acid (279.1/261.0) | 3.32E−04 | 0.78 | 2.04E−04 | 0.77 | | |
| G16BP (339.0/79.0 (2)) | | | | | 3.17E−02 | 0.95 |
| Glycochenodeoxycholate (448.3/74.0) | 5.84E−05 | 1.42 | 9.22E−05 | 2.27 | | |
| Adenylosuccinate (462.1/79.0) | 2.35E−03 | 1.21 | 1.02E−02 | 1.19 | | |
| Glycocholate (464.3/74.0) | 4.25E−04 | 1.79 | 1.94E−04 | 3.01 | | |
| Trimethylamine-N-oxide (76.1/58.0) | | | 4.33E−02 | 1.20 | | |
| Alanine (90.0/44.0) | | | 1.91E−02 | 0.89 | | |
| Dimethylglycine (104.1/58.0) | 1.40E−03 | 0.82 | 2.11E−04 | 0.78 | | |
| Creatinine (114.1/44.0) | 9.08E−03 | 0.90 | 2.04E−03 | 0.88 | | |
| Proline (116.1/70.0) | 1.72E−02 | 1.10 | | | | |
| Threonine (120.1/102.0) | | | 1.87E−02 | 0.92 | | |
| Creatine (132.1/90.0) | | | | | 4.82E−02 | 0.90 |
| Hydroxyproline/Aminolevulinate (132.1/86.2) | 1.66E−03 | 1.37 | 9.09E−04 | 1.32 | | |
| Leucine/iso-Leucine (132.1/86.2) | | | 2.53E−02 | 0.92 | | |
| Asparagine (133.1/74.0) | | | 2.13E−02 | 0.95 | | |
| Acetylcholine (146.1/87.0) | | | 4.13E−02 | 0.92 | | |
| Glutamine (147.1/84.0) | 1.12E−03 | 0.92 | 3.91E−04 | 0.92 | | |
| Lysine (147.1/84.0 (2)) | 1.18E−04 | 0.88 | 5.00E−06 | 0.84 | | |
| Glutamic acid (148.1/84.0) | 6.27E−04 | 1.22 | 5.84E−03 | 1.22 | | |
| Methionine (150.1/61.0) | 1.16E−04 | 0.88 | 1.89E−06 | 0.85 | | |
| Histidine (156.1/110.0) | 2.75E−06 | 0.81 | 2.57E−05 | 0.85 | | |
| Arginine (175.1/70.0) | 1.77E−02 | 1.08 | | 1.05 | | |
| Tryptophan (205.1/146.0) | | | 2.06E−02 | 0.91 | | |
| L-Kynurenine (209.1/94.0) | | | 4.77E−02 | 1.16 | | |
| 2'-Deoxyuridine (229.1/113.0) | 8.10E−04 | 0.91 | 3.81E−05 | 0.89 | | |
| Uridine (245.0/113.0) | 4.72E−02 | 0.92 | 2.26E−05 | 0.84 | 2.55E−02 | 0.92 |
| Adenosine (268.1/136.0) | | | 2.47E−03 | 0.33 | 1.93E−03 | 0.61 |
| 1-Methyladenosine (282.1/150.0) | 2.78E−02 | 1.04 | | | | |

*FC: Fold change calculated as mean ratios for CRC/Healthy control, CRC/Polyp patients or Healthy control/Polyp patients Biomarker Selection, Model Setup, and Cross Validation:

Initially, individual metabolites that had $p<0.05$ were selected as potential biomarker candidates. AUROC, sensitivity, and specificity values for each metabolite were calculated while comparing CRC patients with healthy controls, and CRC patients with polyp patients, respectively, and these values are listed in Tables 8 and 9. As evidenced in these two tables, no single metabolite proved to be sufficiently sensitive and specific by itself to distinguish CRC patients from either healthy controls or polyp patients (generally the AU ROC values are below 0.7 for each metabolite). Partial least square-discriminant analysis (PLS-DA) models with leave one out cross validation were then applied to identify groups of biomarkers that could be used for diagnosing CRC patients. All metabolites that had $p<0.05$ between patient groups (42 metabolites between CRC and control, and 48 metabolites between CRC and Polyp, respectively) were used for initial PLS-DA analysis. As shown by the predicted Y values from different groups, the resulting PLS-DA model these proved to be powerful in separating CRC cancer from both healthy controls and polyp patient groups in this study, with and AUROC of 1.

TABLE 8

| Metabolites | AUROC | Std. Error | 95% Confidence Interval | | Sensitivity | Specificity | Accuracy |
|---|---|---|---|---|---|---|---|
| | | | Lower Bound | Upper Bound | | | |
| Histidine | 0.719 | 0.040 | 0.640 | 0.798 | 0.924 | 0.467 | 0.658 |
| Glyceraldehyde | 0.702 | 0.042 | 0.619 | 0.785 | 0.742 | 0.641 | 0.686 |
| Glycochenodeoxycholate | 0.688 | 0.042 | 0.605 | 0.770 | 0.879 | 0.435 | 0.620 |
| Hyppuric Acid | 0.684 | 0.044 | 0.597 | 0.771 | 0.591 | 0.794 | 0.709 |
| Methionine | 0.680 | 0.043 | 0.596 | 0.764 | 0.667 | 0.630 | 0.646 |
| Lysine | 0.680 | 0.043 | 0.595 | 0.764 | 0.530 | 0.794 | 0.684 |
| Linolenic Acid | 0.668 | 0.044 | 0.581 | 0.755 | 0.439 | 0.880 | 0.696 |
| Glycocholate | 0.665 | 0.043 | 0.580 | 0.749 | 0.742 | 0.565 | 0.703 |
| Glutamic acid | 0.660 | 0.044 | 0.574 | 0.746 | 0.606 | 0.707 | 0.665 |
| N-AcetylGlycine | 0.657 | 0.044 | 0.570 | 0.744 | 0.788 | 0.511 | 0.623 |
| 2'-Deoxyuridine | 0.656 | 0.044 | 0.571 | 0.742 | 0.576 | 0.685 | 0.639 |
| Allantoin | 0.653 | 0.043 | 0.568 | 0.739 | 0.606 | 0.663 | 0.639 |
| Glutamine | 0.652 | 0.044 | 0.566 | 0.739 | 0.546 | 0.707 | 0.639 |
| Aspartic Acid | 0.649 | 0.046 | 0.559 | 0.739 | 0.439 | 0.859 | 0.684 |
| Dimethylglycine | 0.649 | 0.044 | 0.562 | 0.736 | 0.606 | 0.663 | 0.639 |
| Maleic Acid | 0.649 | 0.045 | 0.560 | 0.737 | 0.606 | 0.707 | 0.665 |
| Hydroxyproline/ Aminolevulinate | 0.647 | 0.044 | 0.561 | 0.733 | 0.682 | 0.587 | 0.627 |
| Adenylosuccinate | 0.642 | 0.045 | 0.553 | 0.731 | 0.439 | 0.815 | 0.658 |
| Malonic Acid/3HBA | 0.637 | 0.048 | 0.542 | 0.731 | 0.546 | 0.815 | 0.703 |
| Cystathionine | 0.631 | 0.044 | 0.544 | 0.718 | 0.727 | 0.522 | 0.608 |
| Alpha-Ketoglutaric Acid | 0.629 | 0.046 | 0.540 | 0.719 | 0.393 | 0.870 | 0.671 |
| Kynorenate | 0.627 | 0.045 | 0.538 | 0.716 | 0.636 | 0.576 | 0.601 |
| 2-Aminoadipate | 0.622 | 0.046 | 0.533 | 0.712 | 0.758 | 0.478 | 0.595 |
| Creatinine | 0.622 | 0.045 | 0.533 | 0.711 | 0.697 | 0.554 | 0.614 |
| Urate | 0.615 | 0.045 | 0.527 | 0.703 | 0.636 | 0.587 | 0.608 |
| Homogentisate | 0.613 | 0.045 | 0.524 | 0.701 | 0.455 | 0.772 | 0.639 |
| Proline | 0.611 | 0.046 | 0.521 | 0.702 | 0.424 | 0.794 | 0.639 |
| gama-Aminobutyrate | 0.611 | 0.047 | 0.518 | 0.704 | 0.485 | 0.783 | 0.658 |
| Arginine | 0.611 | 0.047 | 0.518 | 0.704 | 0.591 | 0.685 | 0.646 |
| Oxalic Acid | 0.609 | 0.046 | 0.519 | 0.698 | 0.470 | 0.717 | 0.614 |
| Glucose | 0.604 | 0.045 | 0.515 | 0.693 | 0.864 | 0.370 | 0.576 |
| Linoleic Acid | 0.603 | 0.048 | 0.509 | 0.698 | 0.349 | 0.957 | 0.703 |
| 1-Methyladenosine | 0.603 | 0.045 | 0.514 | 0.691 | 0.712 | 0.544 | 0.614 |
| Pyruvate | 0.601 | 0.046 | 0.510 | 0.692 | 0.712 | 0.533 | 0.608 |
| PEP | 0.600 | 0.045 | 0.511 | 0.688 | 0.955 | 0.261 | 0.551 |
| Erythrose | 0.598 | 0.045 | 0.509 | 0.687 | 0.909 | 0.272 | 0.538 |
| lactate | 0.596 | 0.046 | 0.507 | 0.686 | 0.636 | 0.565 | 0.595 |
| Leucic Acid | 0.596 | 0.045 | 0.507 | 0.685 | 0.712 | 0.467 | 0.570 |
| Fumarate | 0.594 | 0.047 | 0.503 | 0.686 | 0.439 | 0.783 | 0.639 |
| OH-Phenylpyruvate | 0.594 | 0.046 | 0.504 | 0.685 | 0.379 | 0.804 | 0.627 |
| MethylSuccinate | 0.593 | 0.047 | 0.502 | 0.684 | 0.727 | 0.446 | 0.563 |
| Uridine | 0.593 | 0.046 | 0.503 | 0.682 | 0.742 | 0.467 | 0.582 |

TABLE 9

| Metabolites | AUROC | Std. Error | 95% Confidence Interval | | Sensitivity | Specificity | Accuracy |
|---|---|---|---|---|---|---|---|
| | | | Lower Bound | Upper Bound | | | |
| Glyceraldehyde | 0.753 | 0.041 | 0.672 | 0.833 | 0.742 | 0.697 | 0.711 |
| Methionine | 0.732 | 0.043 | 0.648 | 0.816 | 0.667 | 0.750 | 0.711 |
| Lysine | 0.722 | 0.042 | 0.640 | 0.805 | 0.576 | 0.763 | 0.676 |
| Hyppuric Acid | 0.712 | 0.044 | 0.625 | 0.798 | 0.591 | 0.790 | 0.697 |
| Uridine | 0.707 | 0.044 | 0.620 | 0.793 | 0.742 | 0.645 | 0.690 |
| Histidine | 0.705 | 0.044 | 0.620 | 0.791 | 0.682 | 0.658 | 0.669 |
| 2'-Deoxyuridine | 0.701 | 0.044 | 0.615 | 0.786 | 0.576 | 0.790 | 0.690 |
| Glycocheno-deoxycholate | 0.691 | 0.044 | 0.605 | 0.777 | 0.636 | 0.658 | 0.648 |
| Glycocholate | 0.682 | 0.045 | 0.594 | 0.769 | 0.561 | 0.776 | 0.676 |
| Linolenic Acid | 0.681 | 0.045 | 0.593 | 0.769 | 0.546 | 0.750 | 0.655 |
| Dimethylglycine | 0.681 | 0.045 | 0.592 | 0.769 | 0.712 | 0.618 | 0.662 |
| Glutamine | 0.673 | 0.045 | 0.585 | 0.761 | 0.409 | 0.868 | 0.655 |
| Hydroxyproline/ Aminolevulinate | 0.662 | 0.046 | 0.572 | 0.752 | 0.667 | 0.658 | 0.662 |
| Biotin | 0.660 | 0.047 | 0.569 | 0.752 | 0.546 | 0.763 | 0.662 |
| Aspartic Acid | 0.656 | 0.047 | 0.564 | 0.749 | 0.439 | 0.882 | 0.676 |
| N-AcetylGlycine | 0.653 | 0.046 | 0.563 | 0.743 | 0.606 | 0.697 | 0.655 |
| Maleic Acid | 0.651 | 0.047 | 0.560 | 0.742 | 0.606 | 0.697 | 0.655 |

TABLE 9-continued

| Metabolites | AUROC | Std. Error | 95% Confidence Interval | | Sensitivity | Specificity | Accuracy |
| --- | --- | --- | --- | --- | --- | --- | --- |
| | | | Lower Bound | Upper Bound | | | |
| Creatinine | 0.650 | 0.047 | 0.558 | 0.743 | 0.682 | 0.605 | 0.641 |
| Leucic Acid | 0.650 | 0.046 | 0.560 | 0.740 | 0.742 | 0.526 | 0.627 |
| Adenosine | 0.648 | 0.047 | 0.555 | 0.740 | 0.394 | 0.908 | 0.669 |
| Alpha-Ketoglutaric Acid | 0.644 | 0.047 | 0.552 | 0.736 | 0.379 | 0.934 | 0.676 |
| Xanthurenate | 0.644 | 0.047 | 0.551 | 0.736 | 0.621 | 0.711 | 0.669 |
| PEP | 0.642 | 0.046 | 0.551 | 0.732 | 0.939 | 0.382 | 0.641 |
| gama-Aminobutyrate | 0.637 | 0.048 | 0.543 | 0.731 | 0.485 | 0.855 | 0.683 |
| Linoleic Acid | 0.635 | 0.047 | 0.542 | 0.728 | 0.364 | 0.921 | 0.662 |
| Glutamic acid | 0.634 | 0.047 | 0.543 | 0.726 | 0.652 | 0.632 | 0.641 |
| Xanthine | 0.633 | 0.047 | 0.540 | 0.725 | 0.645 | 0.591 | 0.662 |
| Margaric Acid | 0.628 | 0.047 | 0.536 | 0.721 | 0.576 | 0.684 | 0.634 |
| Orotate | 0.628 | 0.047 | 0.535 | 0.720 | 0.652 | 0.579 | 0.613 |
| Kynorenate | 0.625 | 0.047 | 0.533 | 0.718 | 0.667 | 0.618 | 0.641 |
| Adenylosuccinate | 0.625 | 0.048 | 0.531 | 0.719 | 0.515 | 0.763 | 0.648 |
| Glutaric Acid | 0.622 | 0.047 | 0.530 | 0.714 | 0.652 | 0.605 | 0.627 |
| MethylSuccinate | 0.619 | 0.048 | 0.525 | 0.713 | 0.636 | 0.605 | 0.620 |
| Urate | 0.619 | 0.047 | 0.526 | 0.711 | 0.682 | 0.553 | 0.613 |
| Threonine | 0.615 | 0.048 | 0.520 | 0.709 | 0.333 | 0.921 | 0.648 |
| Alanine | 0.614 | 0.047 | 0.521 | 0.707 | 0.864 | 0.395 | 0.613 |
| Tryptophan | 0.613 | 0.048 | 0.519 | 0.706 | 0.697 | 0.540 | 0.613 |
| Asparagine | 0.612 | 0.048 | 0.517 | 0.707 | 0.621 | 0.658 | 0.641 |
| Glycerol-3-P | 0.611 | 0.048 | 0.517 | 0.704 | 0.530 | 0.686 | 0.613 |
| Leucine/iso-Leucine | 0.609 | 0.048 | 0.516 | 0.702 | 0.424 | 0.790 | 0.620 |
| Allantoin | 0.609 | 0.047 | 0.516 | 0.701 | 0.849 | 0.408 | 0.613 |
| Fumarate | 0.608 | 0.048 | 0.513 | 0.702 | 0.439 | 0.842 | 0.655 |
| Homogentisate | 0.607 | 0.047 | 0.514 | 0.700 | 0.803 | 0.434 | 0.606 |
| Pentothenate | 0.605 | 0.048 | 0.510 | 0.700 | 0.106 | 0.934 | 0.549 |
| Acetylcholine | 0.599 | 0.048 | 0.505 | 0.694 | 0.439 | 0.763 | 0.613 |
| Trimethylamine-N-oxide | 0.598 | 0.048 | 0.503 | 0.694 | 0.439 | 0.790 | 0.627 |
| Oxaloacetate | 0.598 | 0.047 | 0.505 | 0.691 | 0.818 | 0.382 | 0.585 |
| L-Kynurenine | 0.596 | 0.048 | 0.502 | 0.691 | 0.424 | 0.816 | 0.634 |

Figure 14A:
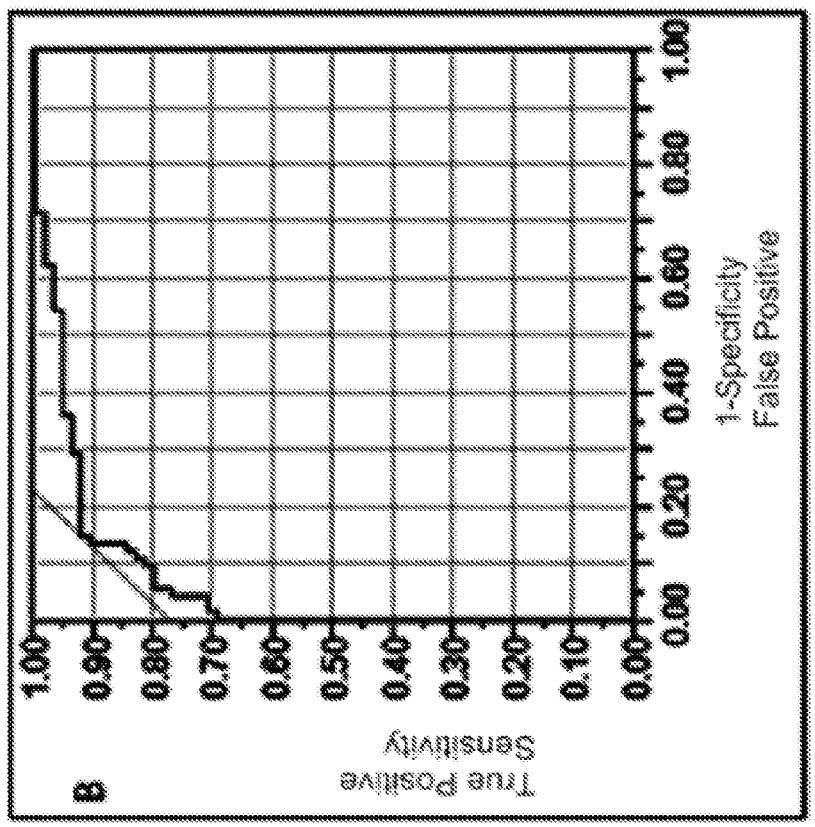
FIGS. 14A-14B. ROC curves of PLS-DA models using all metabolites that have both U-test p-values <0.05 and VIP scores >1. (14A) Cancer patients vs. Healthy Control; AUROC 0.90, Sensitivity: 0.80, Specificity: 0.84; (14B) Cancer patients vs. Polyp patients; AUROC 0.94, Sensitivity: 0.92, Specificity: 0.86.
Figure 14B:
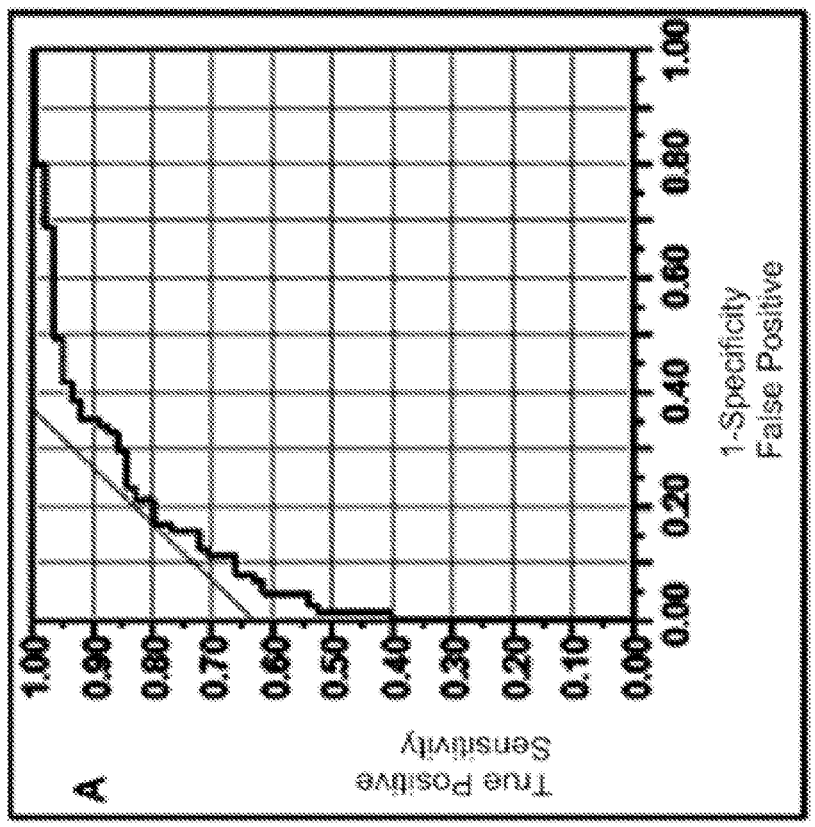
Figure 15A:
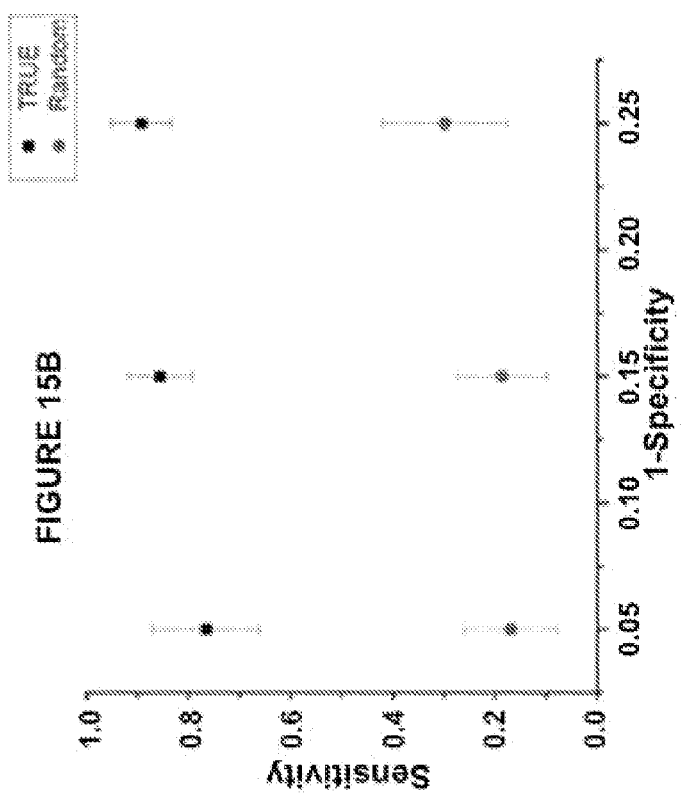
FIGS. 15A-15B. Monte Carlo cross validation (MCCV) results of proposed PLS-DA models using only metabolites that have VIP scores>1. True: true class models; Random: random permutation model. From the left to the right, the respective testing specificities were 0.95, 0.85 and 0.75. (15A) Cancer patients vs. Healthy Controls (15B) Cancer patients vs. Polyp patients.
Figure 15B:
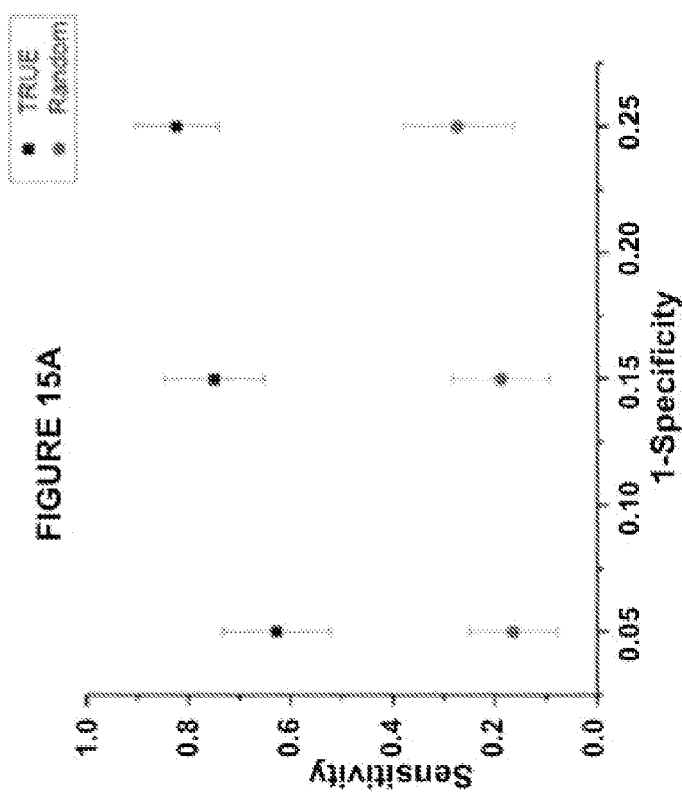

Subsequently, efforts were made to simplify our model in consideration of developing more practical applications suitable for clinical settings. PLS-DA variable importance in projection (VIP) plots (FIG. 7) were generated to evaluate the metabolites that contributed most to the differentiation of CRC patients with the other two groups in this study. When the VIP score threshold was set to 1 according to previous studies,[17] thirteen metabolites (histidine, glycocholate, hippuric acid, malonic acid/3HBA, glycochenodeoxycholate, D-leucic acid, methionine, maleic acid, linolenic acid, hydroxyproline/aminolevulinate, 2-aminoadipate, N-acetylglycine and glyceraldehyde) were selected for the separation between CRC patients and healthy control, and fourteen metabolite biomarkers (adenosine, alanine, PEP, glyceraldehyde, glycocholate, hippuric acid, glycochenodeoxycholate, trimethylamine-N-oxide, N-acetylglycine, hydroxyproline/aminolevulinate, dimethylglycine, linolenic acid, D-leucic acid and pantothenate) were selected for the separation of CRC patients from polyp patients. The detailed pairwise comparison of each VIP metabolite can be seen in FIG. 8. Based on the VIP selection, a second PLS-DA model was built using only the metabolites that had VIP scores greater than 1. To evaluate the diagnostic power of the potential metabolic markers, ROC curves (FIG. 14) were generated. Also in order to exam the robustness of our PLS-DA based CRC diagnostic models, Monte Carlo cross validation (MCCV)[18] was applied to compare the PLS-DA models using the true sample classifications to those with randomly permuted sample class information; superior sensitivity observed in the true sample classifications showed the robust diagnostic power of this metabolic profiling approach (FIG. 15).

Figure 9A:
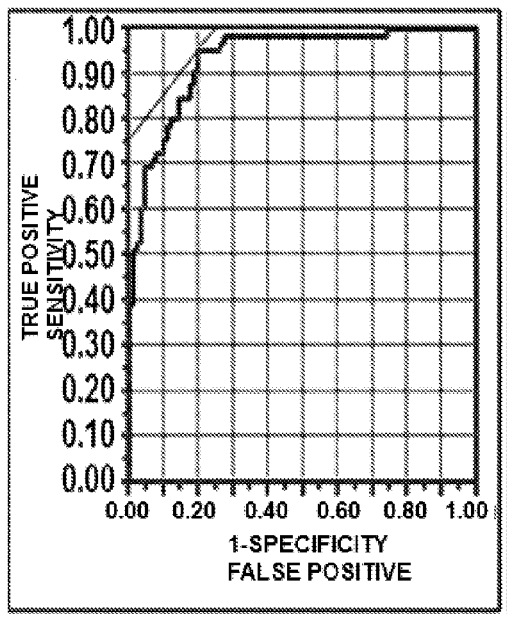
FIGS. 9A-9B. ROC curves for the enhanced PLS-DA model combining metabolites (P<0.05 and VIP score >1) and clinical parameters (age, gender, smoking status, and alcohol status). (9A) Cancer patients vs. Healthy Controls; AUROC 0.93, Sensitivity: 0.96, Specificity: 0.80; (9B) Cancer patients vs. Polyp patients; AUROC 0.95, Sensitivity: 0.89, Specificity: 0.88.
Figure 9B:
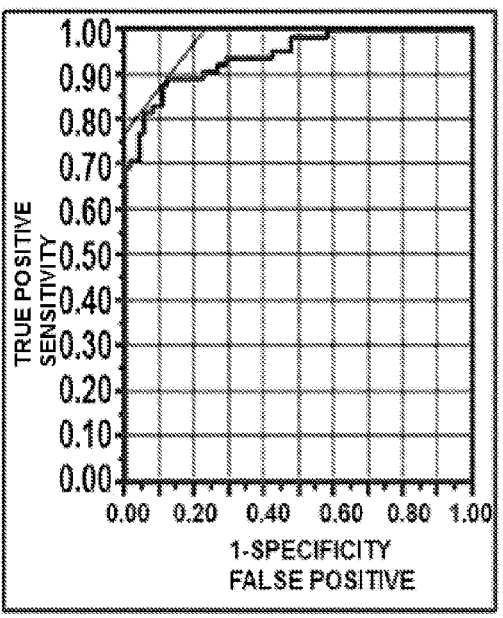

Clinical factors, such as gender, age, medication, and substance status have often been incorporated to build predictive or diagnostic clinical models, and such variables have recently used to enhance metabolite biomarker models.[19] In order to enhance our current VIP metabolite model, four general clinical factors (age, gender, smoking, and alcohol status) were chosen to be candidates for inclusion in the model. The enhanced metabolite model (FIG. 9) showed excellent AUROCs (0.93 and 0.95, respectively, for differentiating CRC patients from healthy controls or polyp patients), high sensitivities (0.96 and 0.89), good specificities (0.80 and 0.88), and low false discovery rates (0.22 and 0.14) were obtained. The model incorporating these four clinical parameters showed better performance than the VIP metabolite model alone (FIG. 14), which suggests that inclusion of clinical factors could improve an already well-performed VIP metabolite model, therefore increasing the diagnostic power of this targeted serum metabolic profiling approach for CRC. MCCV was again applied, and the advanced performance of the true class models over the random permutation model was obtained as anticipated (FIG. 10). Sensitivity and specificity values after MCCV were X±x and Y±y, indicating the strong performance of this combined metabolite and clinical model approach.

After the enhanced metabolite based prediction model was established, subgroups of CRC patients in this study were analyzed using the model to evaluate the diagnostic power for specific CRC disease type and stage. As can be seen in Table 6, using the clinical factor enhanced VIP metabolite model, all AUROCs were equal to or greater than 0.93. The models have slightly better diagnostic power in colon cancer detection compared to rectal cancer, and also have varying performances depending on different stages of CRC, with the highest performance seen for stage IV CRC diagnosis.

TABLE 6

The performance of established prediction models for different CRC diagnostic groups and cancer stages.

|  | Colon Cancer | Rectal Cancer | Stage I/II | Stage III | Stage IV |
|---|---|---|---|---|---|
| Compared to Healthy Controls | | | | | |
| AUROC | 0.96 | 0.93 | 0.93 | 0.93 | 0.99 |
| Sensitivity | 0.95 | 0.93 | 0.95 | 0.76 | 0.94 |
| Specificity | 0.88 | 0.82 | 0.82 | 0.95 | 0.94 |
| Compared to Polyp Patients | | | | | |
| AUROC | 0.96 | 0.95 | 0.97 | 0.94 | 0.99 |
| Sensitivity | 0.92 | 0.89 | 0.95 | 0.94 | 1.00 |
| Specificity | 0.91 | 0.95 | 0.92 | 0.82 | 0.96 |

Discussion

During the past decade, interest has grown in applying mass spectrometry-based metabolic profiling for analyzing and monitoring cancer related metabolic alterations, and in particular to thereby provide sensitive and valuable diagnostic information.[11a, 20] In the current investigation, we explored the combination of targeted metabolic profiling with multivariate statistical analysis for the discovery of sensitive and specific panel of metabolite biomarkers for CRC detection. We have used this particular method to monitor 158 metabolites from 25 metabolic pathways of potential significance by LC-MS/MS using both positive and negative ionization modes and MRM methods. Based on our multiple step biomarker selections, model constructions, and cross validation, we successfully demonstrated the robust diagnostic power of this metabolic profiling approach in this study comprised of 234 patient samples.

Figure 8B:
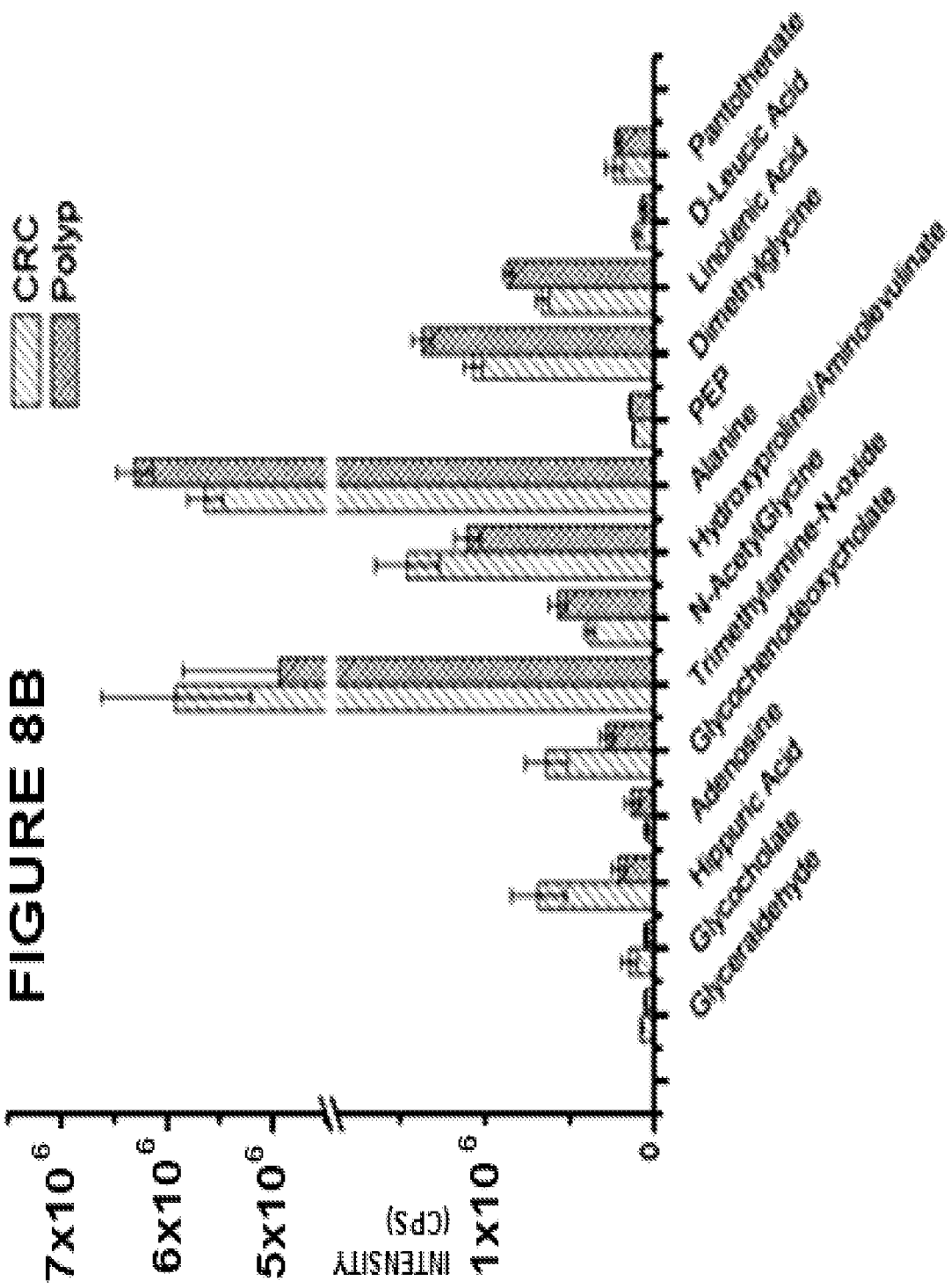

To date, a number of studies have performed mass spectrometry based methods (such as GC-MS and LC-QTOF-MS) for detecting the serum metabolic alterations from CRC patients.[13a, 13c, 21] However, these studies have typically used global metabolic profiling methods to measure as many features that can be captured by the analytical platform, which can make them less reliable and robust. In contrast, the very reproducible targeted LC-MS/MS metabolite profiling approach we applied in this current study has median CV values of ~8%, and has not been reported in any previous CRC metabolic profiling study. Additionally, instead of only applying database searches for compound annotation,[13b, 13c] we tested all the targeted metabolites included in this study with pure standard compounds (although the somewhat low possibility of an unknown compound with a similar m/z and retention time being detected simultaneously still exists). It is also worth noticing that there are only a few studies available so far regarding the comparison of metabolic shifts from healthy controls to polyp patients and then to CRC patients,[22] and none of these studies used serum samples. In our current study, we performed pairwise comparisons of serum metabolites from CRC patients, polyp patients, and healthy controls, and observed significant alterations in a variety of the metabolites detected (e.g., amino acids, carboxylic acid, fatty acids and nucleosides); see Table 10 for detailed metabolite classifications. Furthermore, significantly altered serum metabolites with p<0.05 (Mann-Whitney U test) and VIP>1 in the first PLS-DA model were selected in this study and summarized (FIG. 8). Meanwhile, efforts were also made in this study to look for possible enhancements to the VIP metabolite model using 4 clinical factors, including age, gender, smoking and alcohol status. After adding these clinical factors to the selected VIP metabolites, improved AUROC, sensitivity, and/or selectivity were observed in the cross validated PLS-DA model.

TABLE 10

Percentage of different classes of metabolites that have significant alterations (p < 0.05) in comparing CRC patients to either healthy controls or polyp patients.

| Classification | Percentage |
|---|---|
| Alcohols | 1.72% |
| Alkylamines | 1.72% |
| Amino Acid | 39.66% |
| Carboxylic Acids | 8.62% |
| Cinnamic Acids | 1.72% |
| Fatty Acids | 6.90% |
| Imidazolidines | 1.72% |
| Imidazopyrimidines | 1.72% |
| Keto Acids | 1.72% |
| Lactams | 1.72% |
| Linoleic Acids | 3.45% |
| Monosaccharides | 5.17% |
| Neurotransmitter | 1.72% |
| Organic Oxoanionic | 1.72% |
| Organic Oxoazanium Compounds | 1.72% |
| Oxolanes | 1.72% |
| Phenylacetic Acid | 1.72% |
| Purine Nucleosides | 3.45% |
| Pyrimidine Nucleosides | 3.45% |
| RNA | 1.72% |
| Steroids | 3.45% |
| Thienoimidazolidines | 1.72% |
| Vitamins | 1.72% |

Figure 11:
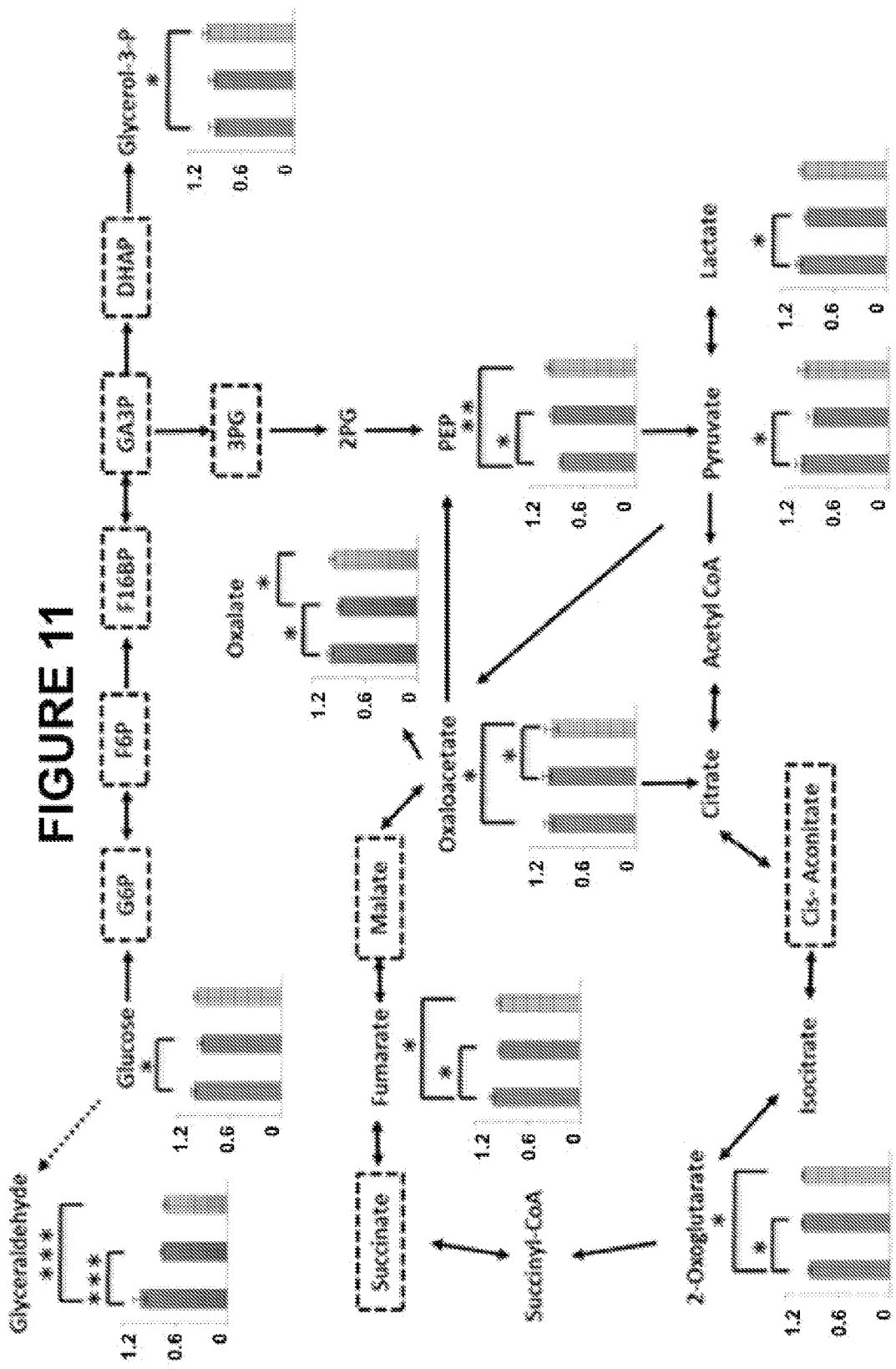
FIG. 11. Metabolic network of significantly changed metabolites in central carbon metabolism (Glycolysis, TCA, and other related pathways). Bar chart left to right: CRC, Healthy controls, and polyp patients; Y axis represents relative abundance of MS signal (normalized to the highest peaks in comparison). Dash lines surrounding compounds means measured but not significant between any of two groups. *, p<0.05; , p<0.01; *, p<0.001.
Figure 12:
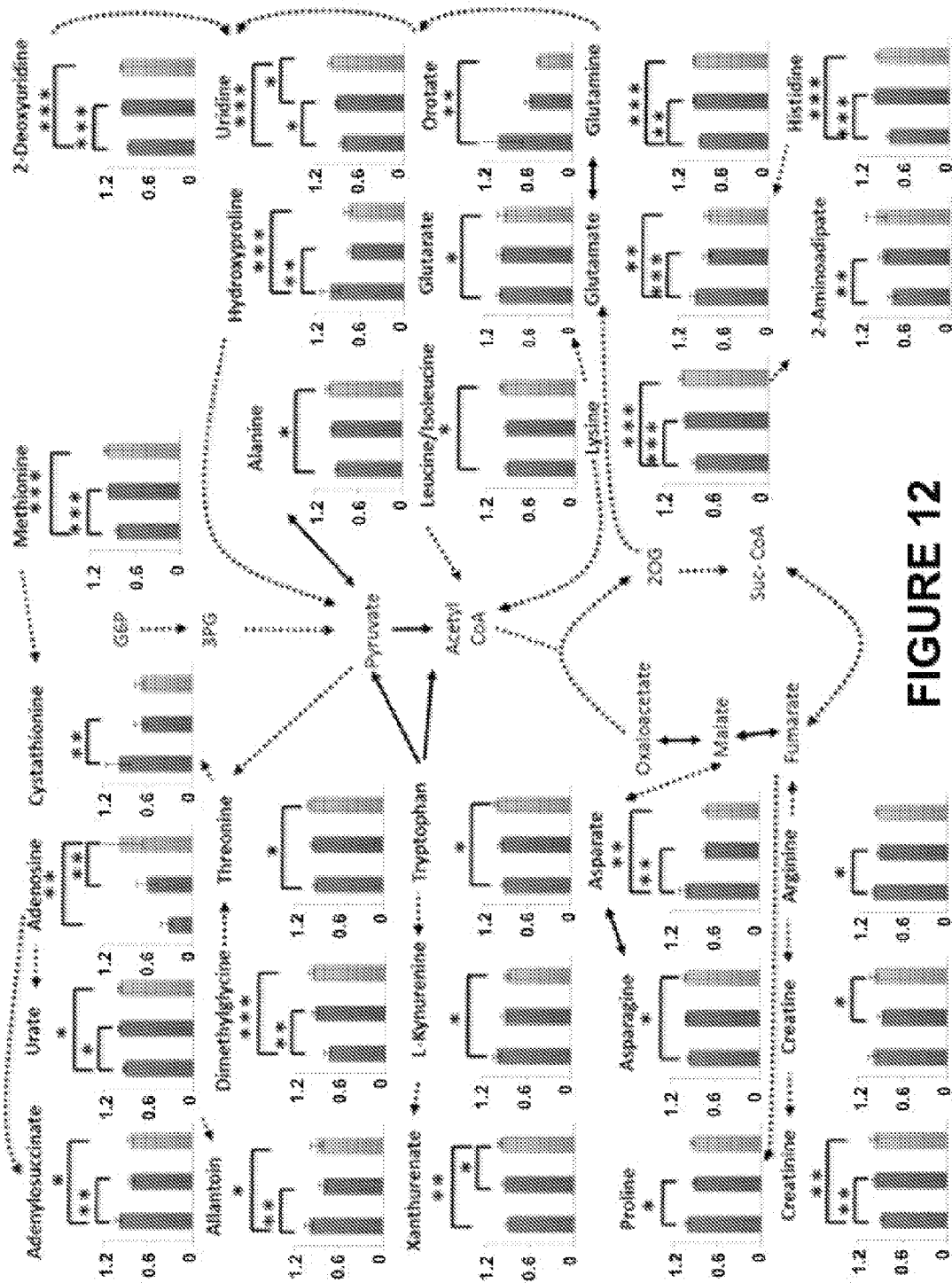
FIG. 12. Metabolic network of the significantly changed metabolites involved in amino acid, purine, and pyrimidine metabolisms. Bar charts left to right: CRC patients, Healthy Controls and Polyp patients, Y axis represents relative abundance of MS signal (normalized to the highest peaks in comparison). Dashed lines surrounding compounds means measured but not significant difference between any of two groups. *, p<0.05; , p<0.01; *, p<0.001.

In order to understand the possible connections among these serum metabolites, metabolic pathway maps were constructed based on information obtained from the Kyoto Encyclopedia of Genes and Genomes website (www.genome.jp/kegg/) and are shown in FIGS. 11 and 12. For example, in examining central carbon metabolism, including glycolysis, the tricarboxylic acid (TCA) cycle, and other related pathways, ten metabolites were altered significantly (FIG. 11). Mean glucose levels from CRC patients are significantly higher than in healthy controls, which has previously been related to a higher risk of CRC,[23] and significantly impaired glucose metabolism has also been reported in CRC cases previously.[24] Meanwhile, significantly increased pyruvate and lactate levels in CRC patients were also detected in our study, which matched previous reports.[13a, 13c] Increased glycolysis is proposed to be associated with many tumors and with cancer cell growth, and forms part of the well-known Warburg effect.[25] Three metabolites were detected as having significant differences in the pairwise comparison of CRC with the other two groups; 2-oxoglutarate was found decreased in CRC patients, indicating that the TCA cycle is impaired leading to reduced mitochondrial respiration. The other two TCA cycle metabolites, fumarate and oxaloacetate, were however found slightly increased in CRC patients compared to either healthy control or polyp patients. Interestingly, significantly increased fumarate levels were also reported by a previous metabolic study[26] and was suggested as part of a typical metabolic fingerprint of hypoxic cells. The authors from that study also proposed that so-called fumarate respiration, which is a known activity of some parasites and bacteria, contributes greatly to the energy generation of cancer cells under conditions of glucose deprivation and severe hypoxia.[27] On the other hand, oxaloacetate has been reported to contribute greatly to aspartic acid production by transamination,[13b] while an increase in aspartic acid levels was reported in various studies and was proposed as one of the nutrients that cancer cells prefer.[13d]

Amino acid, purine and pyrimidine metabolism pathways were also significantly impacted by CRC, as can be seen in FIG. 12. Cancer cells are known to use some amino acids as an energy source;[28] alterations of amino acids therefore can be indicative of cancer cell activities. For example, significant decreases of alanine, glutamine, lysine, creatinine, asparagine, and tryptophan, and significant increase of glutamate, proline, asparate, and hydroxylproline in CRC patient serum samples compared to either healthy controls and/or polyp patients were detected in our study, which were in agreement with previous serum studies.[13b, 13c, 21] It is interesting to note that these observations are somehow different from a previous CRC tissue study, in which most of the free amino acids were higher in CRC due to possible up-regulation of cell amino acid biosynthesis and cell autophagy,[26] suggesting the potential influence from different clinical specimens to metabolites level. However, metabolite level changes in tissue and serum are not always correlated[29]. Altered purine metabolism has been reported in other types of cancer such as liver cancer, and enzyme pattern imbalances and other changes in purine metabolism have been linked to disease progression.[30] Therefore, based on the evidence of significant changes in adenosine, urate, adenylosuccinate, and allantoin between CRC and the other two groups, the impact of CRC to purine metabolism can be observed. Pyrimidine metabolism, which has close connection to glutamine metabolism (FIG. 12), can also be influenced by CRC.[13d, 31] In our study several pyrimidine metabolites, such as uridine and 2-deoxyuridine, were detected as significantly decreased in CRC patients compared to both healthy controls and polyp patients, while orotate was measured to be higher in CRC than polyp patients.

Most of the key serum metabolite biomarker candidates (determined by the criteria of both p<0.05 and VIP score>1) discovered in this study are of biological importance and have been proposed as CRC related compounds. For example, glycocholate and glycochenodeoxycholate, two intermediate metabolites between primary bile synthesis and secondary bile synthesis, have significantly higher concentrations in CRC patients compared to healthy controls or polyp patients (in agreement with a previous report[32]), suggesting significant increases of primary and secondary bile acids in CRC patients. Down regulation of histidine was observed in our study and by others,[13b, 13c, 33] and this down regulation may be due to the acceleration of decarboxylation from histidine to histamine in CRC patients, which is caused by the increased activity of histidine decarboxylase.[34] Increased concentrations of hydroxylproline were also observed in CRC patients, and a previous study suggested that the excessive degradation of collagen in these patients may be the cause.[26] Furthermore, we discovered some new potential CRC serum biomarkers, including glyceraldehyde, glycocholate, linolenic acid, and D-leucic acid that have not been previously reported.

Figure 16:
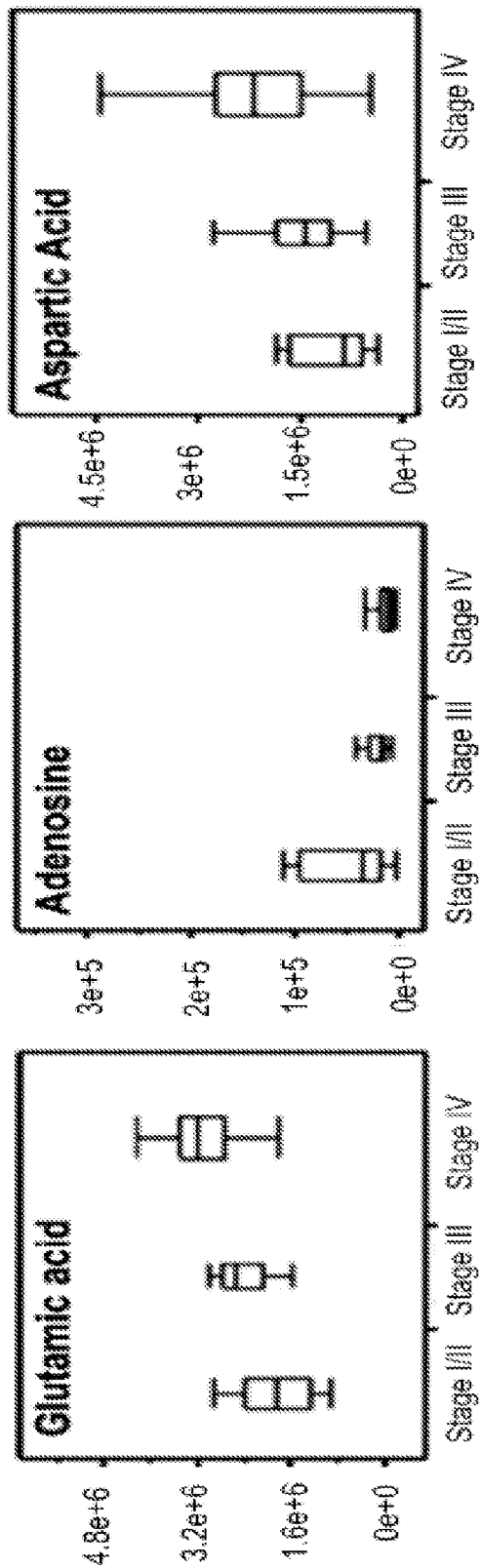
FIG. 16. Box plots of metabolites that significantly changed (p<0.05) over different CRC stages.
Figure 18C:
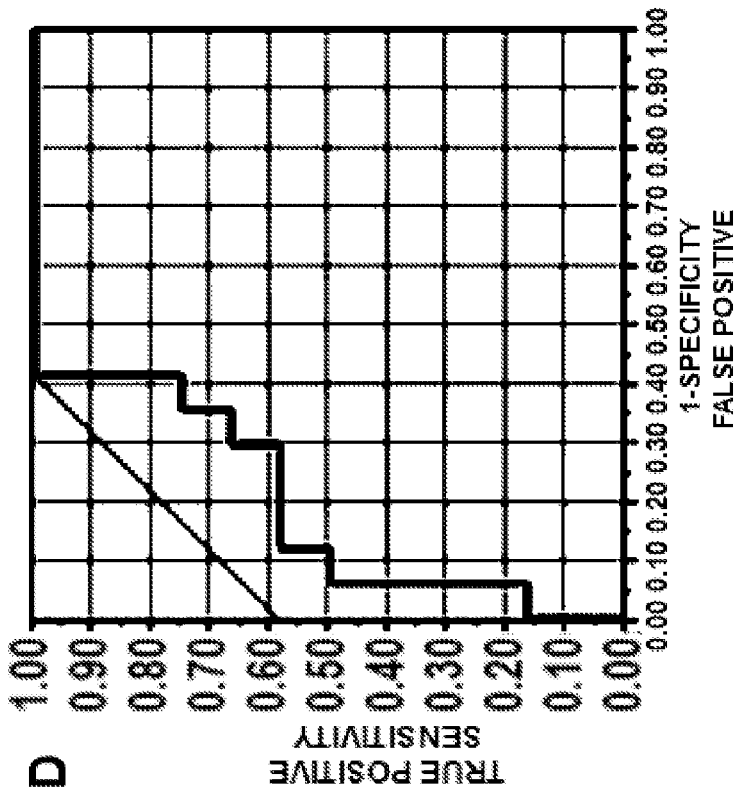
Figure 18D:
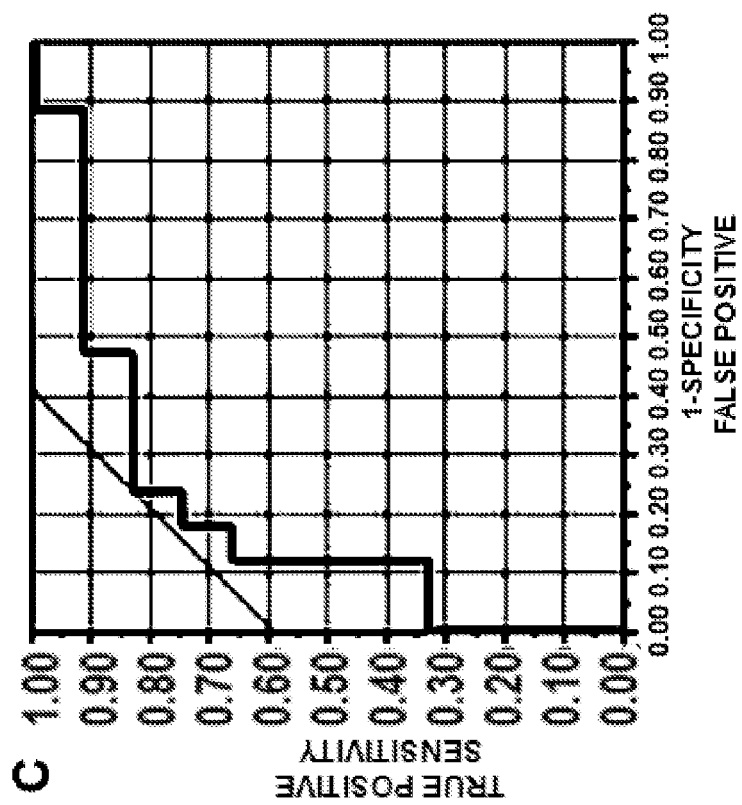
Figure 18E:
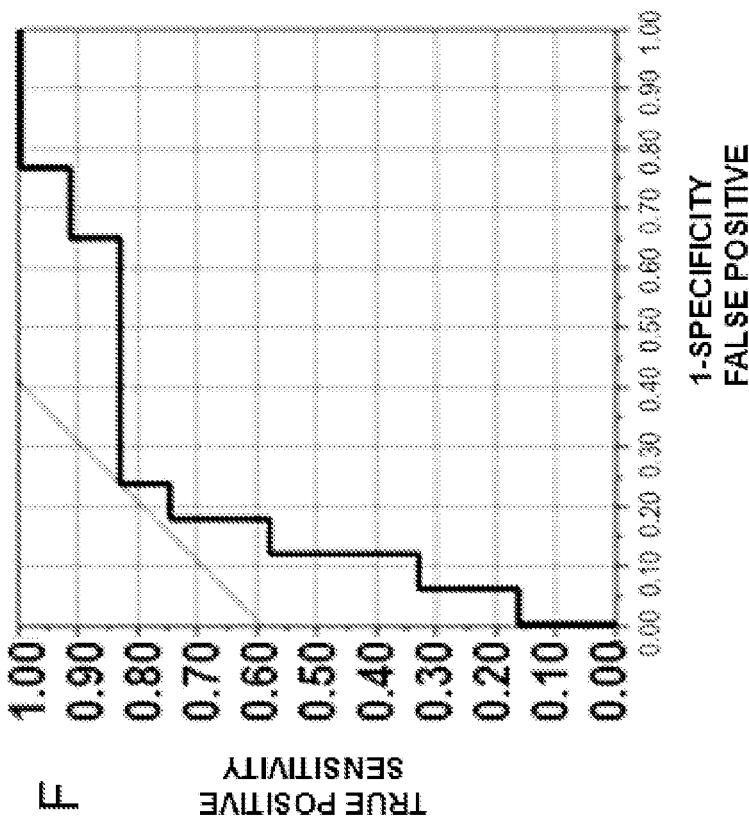
Figure 18F:
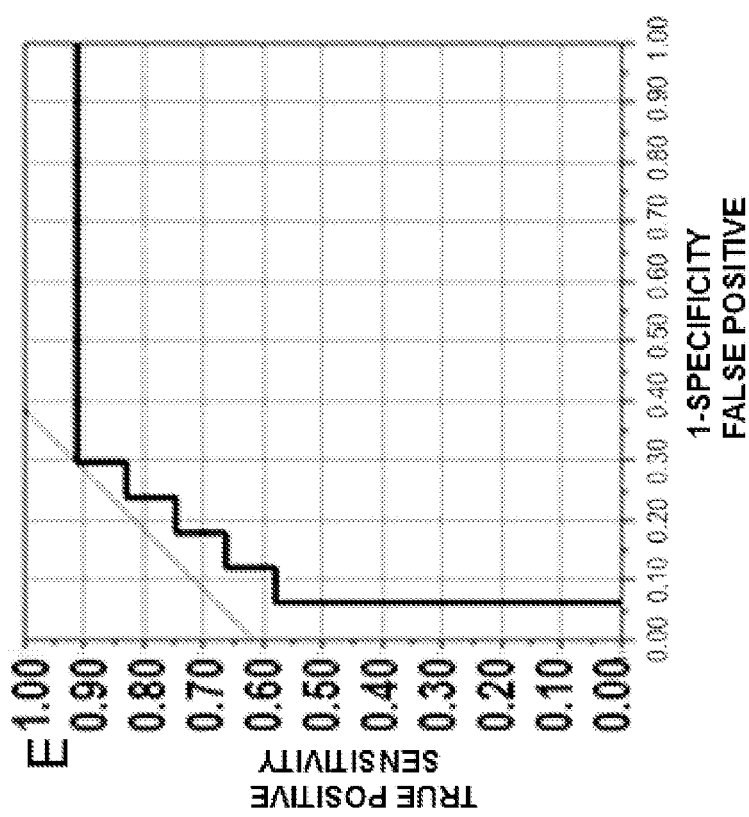

Besides the diagnostic power of metabolite biomarkers for comparing CRC patients with healthy controls and polyp patients, we also carefully examined the metabolite changes in CRC patients with different disease stages, and observed that three significantly altered serum metabolites, namely glutamic acid, adenosine, and aspartic acid, that consistently changed over the different cancer stages (see FIG. 16). These metabolites could be further explored in the future for the potential differentiation between early stage and late stage CRC.

This is the first time that an LC-MS/MS targeted serum metabolic profiling approach has been applied for the comparison of CRC patients to both healthy controls and polyp patients, and our results demonstrate that a panel of 13 serum metabolites for the differentiation of CRC patients and healthy controls, and 14 for the differentiation of CRC and polyp patients, when enhanced by four clinical factors (age, gender, smoking and alcohol status), can potentially serve as a novel disease biomarker panel for CRC diagnosis.

References Cited in Example 2

1. Weitz, J.; et al., *The Lancet* 2005, 365 (9454), 153-165.
2. Siegel, R.; et al., *CA. Cancer J. Clin.* 2014, 64 (1), 9-29.
3. Rex, D. K.; et al., *Am J Gastroenterol* 2009, 104 (3), 739-750.
4. Bond, J. H., *Endoscopy* 2003, 35 (01), 27-35.
5. Taylor, D. P.; et al., *Genet Med* 2011, 13 (8), 737-743.
6. *Cancer Facts & Figures* 2013; American cancer society: Atlanta, Ga., 2013.
7. Ahlquist, D. A.; et al., *Gastroenterology* 2012, 142 (2), 248-256.
8. (a) Link, A.; et al., *Cancer Epidemiol Biomark Prev* 2010, 19 (7), 1766-1774; (b) Luo, X. et al., *Cancer Epidemiology Biomarkers & Prevention* 2011, 20 (7), 1272-1286.
9. Marshall, K. W. et al., *International Journal of Cancer* 2010, 126 (5), 1177-1186.
10. (a) Ritchie, S. et al., *BMC Med.* 2010, 8 (1), 13; (b) Ritchie, S. A. et al., *Int. J. Cancer* 2013, 132 (2), 355-362.
11. (a) Patti, G. J. et al., *Nat Rev Mol Cell Biol* 2012, 13 (4), 263-269; (b) Gu, H. et al., *Future Oncol.* 2012, 8 (10), 1207-1210; (c) Gowda, G. A. N. et al., *Expert Rev. Mol. Diagn.* 2008, 8 (5), 617-633; (d) Scalbert, A. et al., *Metabolomics* 2009, 5 (4), 435-458; (e) Nicholson, J. K. et al., *Nature* 2012, 491 (7424), 384-392; (f) Fan, T.-M.; Lane, A., *J. Biomol. NMR* 2011, 49 (3-4), 267-280; (g) Reaves, M. L.; Rabinowitz, J. D., *Curr. Opin. Biotechnol.* 2011, 22 (1), 17-25; (h) Bain, J. R. et al., *Diabetes* 2009, 58 (11), 2429-2443; (i) Yanes, O. et al., *Anal. Chem.* 2011, 83 (6), 2152-2161.
12. Spratlin, J. L. et al., *Clinical Cancer Research* 2009, 15 (2), 431-440.
13. (a) Qiu, Y. et al., *Journal of Proteome Research* 2009, 8 (10), 4844-4850; (b) Nishiumi, S. et al., *PLoS ONE* 2012, 7 (7), e40459; (c) Tan, B. et al., *Journal of Proteome Research* 2013, 12 (6), 3000-3009; (d) Denkert, C. et al., *Molecular Cancer* 2008, 7 (1), 72.
14. Chan, E. C. Y. et al., *Journal of Proteome Research* 2008, 8 (1), 352-361.
15. Ma, Y.-L. et al., *Dig Dis Sci* 2009, 54 (12), 2655-2662.
16. Li, F. et al., *Rapid Commun. Mass Spectrom.* 2013, 27 (1), 24-34.
17. Chong, I.-G. et al. *Chemom. Intell. Lab. Syst.* 2005, 78 (1-2), 103-112.
18. (a) Rocha, C. u. M. et al., *J. Proteome Res.* 2011, 10 (9), 4314-4324; (b) Wei, S. et al., *Metabolites* 2012, 2 (4), 701-716.

19. Rhee, Eugene P. et al., *Cell Metab.* 2013, 18 (1), 130-143.
20. Benjamin, Daniel I. et al., *Cell Metabolism* 2012, 16 (5), 565-577.
21. Leichtle, A. et al., *Metabolomics* 2012, 8 (4), 643-653.
22. (a) Ong, E. S. et al., *Molecular & Cellular Proteomics* 2010; (b) Eisner, R. et al., *BioMed Research International* 2013, 2013, 11.
23. Schoen, R. E. et al., *J. Natl. Cancer Inst.* 1999, 91 (13), 1147-1154.
24. Ehrmann-Jósko, A.; et al., *Scand. J. Gastroenterol.* 2006, 41 (9), 1079-1086.
25. (a) Warburg, O., *Science* 1956, 123 (3191), 309-314; (b) Vander Heiden, M. G. et al., *Science* 2009, 324 (5930), 1029-1033.
26. Hirayama, A. et al., *Cancer Research* 2009, 69 (11), 4918-4925.
27. Chen, Z. et al., *J Bioenerg Biomembr* 2007, 39 (3), 267-274.
28. Argilés, J.; Azcón-Bieto, J., *Mol. Cell. Biochem.* 1988, 81 (1), 3-17.
29. Huang, Q. et al., *Cancer Research* 2013, 73 (16), 4992-5002.
30. Weber, G., *Clin. Biochem.* 1983, 16(1), 57-63.
31. Israel, M.; Schwartz, L., *Mol. Cancer* 2011, 10 (1), 70.
32. Tocchi, A. et al., *Surg. Today* 1996, 26 (2), 101-104.
33. Qiu, Y. et al., *Journal of Proteome Research* 2010, 9 (3), 1627-1634.
34. Garcia-Caballero, M. et al., *Agents Actions* 1988, 23 (3-4), 357-360.

Example 3: Targeted Serum Metabolite Profiling for Colorectal Cancer Progression Monitoring In this example, a targeted LC-MS/MS metabolic profiling approach was applied using serial serum samples to monitor CRC patient disease progression. A PLS-DA model using a panel of 5 metabolites (succinate, N2, N2-dimethylguanosine, adenine, citraconic acid, and 1-methylguanosine) with or without CEA was established, and excellent model performance (sensitivity=0.83, specificity=0.94, AUROC=0.91) was obtained, superior to CEA alone (sensitivity=0.75, specificity=0.76 AUROC=0.80). Monte Carlo cross validation was applied, and the robustness of the model was clearly observed by the separation of true classification models from the random permutation models. This is the first study using an LC-MS/MS targeted serum metabolic profiling approach for CRC disease progression monitoring. The results support the usefulness of metabolic profiling for CRC patient therapy monitoring.

The most widely used CRC monitoring test is carcinoembryonic antigen (CEA); CEA is a glycoprotein involved in cell adhesion that is normally produced during fetal development. Production of this protein ceases prior to birth and is, therefore, not typically present in the blood of healthy adults (14). Elevated levels of CEA (>2.5 ng/mL) are most commonly used as a biomarker for monitoring of CRC following tumor resection and for monitoring the response of metastatic CRC to systemic therapy. Ratio methods that compare sequential CEA measurements are also used, often with improved performance (15). While CEA is FDA approved for these applications, elevated CEA levels are also associated with other types of carcinomas, such as gastric, pancreatic, lung, and breast, making it an unreliable biomarker solely for CRC cancer diagnosis or early cancer detection (16). CEA levels can respond to recurrent CRC with a sensitivity of ~80% (range, 17-89%) and specificity of ~70% (range, 34-91%) (14, 17), which is less than optimal.

In this study we utilized a targeted liquid chromatography tandem mass spectrometry (LC-MS/MS) serum metabolic profiling approach to identify metabolites that correlate with CRC patient disease status. Using 49 serial serum samples from 20 CRC patients, a number of metabolites showed a significant difference (p-values<0.05) in their sequential ratios between CRC patients with progressing disease and CRC patients with other disease status. The individual performance of several of these metabolites was higher than CEA alone. Partial least squares-discriminant analysis (PLS-DA) was performed using sequential patient sample ratios of these metabolite biomarkers, and high sensitivity and specificity were obtained for the differentiation of CRC patients with disease progression status compared to patients with stable disease or complete remission.

Materials and Methods

Chemicals and Reagents:

LC-MS grade acetonitrile, ammonium acetate, and acetic acid were purchased from Fisher Scientific (Pittsburgh, Pa.). Standard compounds corresponding to the measured metabolites were purchased from Sigma-Aldrich (Saint Louis, Mo.) or Fisher Scientific (Pittsburgh, Pa.), and a list of these compounds can be found in the Supplementary Table 15. Stable isotope-labeled tyrosine and lactate (L-tyrosine-$^{13}C_2$ and sodium-L-lactate-$^{13}C_3$) were purchased from Cambridge Isotope Laboratories, Inc. (Tewksbury, Mass.). The purities of non-labeled standards were >95-99%, whereas the purities of the two $^{13}C$ labeled compounds were >99%.

TABLE 15

List of targeted metabolites in this study (verified by chemical standards).

| | | |
|---|---|---|
| Glycine | Normetanephrin | Ribose-5-P |
| Trimethylamine-N-oxide | Histamine | Adenylosuccinate |
| Alanine | Pyruvate | D-Leucic Acid |
| Aminoisobutyrate | lactate | GDP |
| Choline | Acetoacetate | GTP |
| Dimethylglycine | Fumaric | DCDP |
| Serine | Succinate | Pyridoxal-5-P |
| Creatinine | Nicotinate | Gibberellin |
| Proline | Glutaric Acid | Adipic Acid |
| Valine | Malate | Maleic Acid |
| Betaine | Hypoxanthine | Methylmalonate |
| Threonine | Alpha-Ketoglutaric Acid | DHAP |
| Taurine | Xanthine | Chenodeoxycholate |
| Creatine | PPA | G16BP |
| Hydroxyproline | Urate | F6P/F1P |
| Leucine/iso-Leucine | Homogentisate | Oxalic Acid |
| Ornithine | PEP | Glyceraldehyde |
| Homocysteine | D-GA3P | Glycerate |
| Acetylcholine | Glycerol-3-P | N-AcetylGlycine |
| Glutamine | Hyppuric Acid | Guanidinoacetate |
| Glutamic acid | Glucose | Mevalonate |
| Methionine | 4-Pyridoxic acid | Allantoin |
| Cystamine | 2/3-Phosphoglyceric Acid | Inositol |
| Histidine | Erythrose | Homovanilate |
| Carnitine | Cystathionine | Xanthurenate |
| Phenylalanine | G1P/G6P | Pentothenate |
| Arginine | Reduced glutatione | Biotin |
| Glucosamine | F16BP/F26BP | DCMP |
| Tyrosine | Sucrose | DUMP |
| Sorbitol | 5-Formyl THF | Geranyl Pyrophosphate |
| Epinephrine | Oxidized glutathione | DTMP |
| Tryptophan | gama-Aminobutyrate | CMP |
| 5-Hydroxytryptophan | Malonic Acid/3HBA | Lactose |

TABLE 15-continued

List of targeted metabolites in this study
(verified by chemical standards).

| | | |
|---|---|---|
| Uridine | Citraconic Acid | cGMP |
| Phosphotyrosine | Adenine | AMP |
| Adenosine | Shikimic Acid | IMP |
| Inosine | Aconitate | PGE |
| Guanosine | Citrulline | OMP |
| XMP | Citric Acid | UDP |
| L-Kinurenine | Cystine | ADP |
| Lysine | Xanthosine | Folic Acid |
| Cytosine | Uracil | DUTP |
| Homoserine | OH-Phenylpyruvate | ATP |
| Niacinamide | Glycochenodeoxycholate | Taurocholate |
| 1-Methylhistamine | Glycocholate | Fructose |
| Asparagine | Dopamine | Aspartic Acid |
| Salicylurate | Melatonin | MethylSuccinate |
| 2'-Deoxyuridine | Orotate | Myristic Acid |
| 3-Hydroxykynurenine | Anthranilate | Margaric Acid |
| Cytidine | Glucoronate | Linoleic Acid |
| Pyroglutamic Acid | Oxaloacetate | Linolenic Acid |
| 1-Methyladenosine | Propionate | Galactose |
| 1-Methylguanosine | 2-Aminoadipate | |
| N2,N2-Dimethylguanosine | Kynorenate | |
| Aminolevulinic Acid | 3-Nitro-tyrosine | |

Clinical Samples:

Patient recruitment and sample collection protocols were approved by Institutional Review Boards at Purdue University and the Indiana University School of Medicine. Informed consent was provided from all subjects in the study according to institutional guidelines. Longitudinal serum samples (49) were obtained from 20 CRC patients and included in this study. Patient summary demographic and clinical information are shown in Table 11. The four major CRC disease statuses are defined as the following: At diagnosis (AD)—the patient has just been diagnosed with cancer and has not yet received any form of treatment for it; Disease progression (DP)—a patient has growing tumor (determined either clinically or by imaging), and the patient is usually on treatment but can also be off treatment; Stable disease (SD)—the patient has a tumor, may or may not be on treatment, and imaging studies/clinical exam suggest that his/her tumor is the same size as determined in previous visits; and Complete remission (CR)—the patient has a tumor, may or may not be on treatment, and imaging studies/clinical exam suggest that he/she has no visible tumor anymore. All samples were evaluated for serum CEA values at the time of collection, and this information was also utilized for comparison in this study. Each blood sample was allowed to clot for 45 min and then centrifuged at 2000 rpm for 10 min. All samples were stored at −80° C. until experiments were performed.

TABLE 11

Summary of patient and sample information

| | |
|---|---|
| Age (SD) | 54.9 (15.6) |
| BMI (SD)* | 25.8 (3.7) |
| Gender | |
| Male | 9 |
| Female | 11 |
| Stage at diagnostics | |
| Stage I/II | 2 |
| Stage III | 4 |
| Stage IV | 14 |

TABLE 11-continued

Summary of patient and sample information

| Serum samples (# of ratios) | |
|---|---|
| Disease progression | 22 (12) |
| Other status | 27 (17) |

*BMI Information for 5 patients was not recorded

Sample Preparation:

Frozen samples were first thawed at room temperature for approximately 45 min, and 50 µL of each sample was protein precipitated using two rounds of cold methanol extraction (150 µL and 300 µL, respectively) at −20° C. The resulting supernatant containing desired metabolites were collected into a new Eppendorf vial, dried using a Vacufuge Plus evaporator (Eppendorf, Hauppauge, N.Y.), and then reconstituted in 500 µL of 5 mM ammonium acetate in 40% water/60% acetonitrile+0.2% acetic acid containing 5.13 µM L-tyrosine-$^{13}C_2$ and 22.5 µM sodium-L-lactate-$^{13}C_3$. The two isotope-labeled internal standards were added to each sample to monitor system performance. The samples were filtered through 0.45 µm PVDF filters (Phenomenex, Torrance, Calif.) prior to LC-MS analysis. A pooled human serum sample was extracted using the same procedure as above. This sample was used as the quality control (QC) sample and was analyzed once every ten serum samples.

Liquid Chromatography Mass Spectrometry Conditions:

Two Agilent 1260 binary pumps, an Agilent 1260 auto-sampler, and an Agilent 1290 column compartment containing a column-switching valve (Agilent Technologies, Santa Clara, Calif.) were used in this study. Two separate injections (10 µL for analysis using negative ionization mode and 2 µL for analysis using positive ionization mode) were made for each sample. Chromatographic separations were performed using hydrophilic interaction chromatography (HILIC) on two SeQuant ZIC-cHILIC columns (150×2.1 mm, 3.0 µm particle size, Merck KGaA, Darmstadt, Germany) connected in parallel. This setup facilitates high-throughput analysis as it allows one column to perform the separation while the other column is being reconditioned for the next sample injection. The reconstituted serum samples were gradient-eluted at 0.300 mL/min using solvents A (5 mM ammonium acetate in 90% $H_2O$/10% acetonitrile+0.2% acetic acid) and B (5 mM ammonium acetate in 90% acetonitrile/10% $H_2O$+0.2% acetic acid). The auto-sampler temperature was kept at 4° C., the column compartment was set at 40° C., and the total separation time for both ionization modes was 20 min. The gradient conditions for both separations were identical and are briefly summarized as follows: 75% B isocratic for 2 min, 75% B to 30% B in three min, 30% B isocratic for 4 min, and then back to 75% B in two min.

The metabolite identities were confirmed by spiking the pooled serum sample used for method development with mixtures of standard compounds (each mixture contained five standard metabolites). The few metabolites that could not be well separated and had similar m/z values (<1 Da) were integrated as single peaks (e.g., malonic acid and 3-hydroxybutyric acid).

The mass spectrometer setting was optimized and described as follows. Briefly, after the chromatographic separation, MS ionization and data acquisition were performed using an AB Sciex QTrap 5500 mass spectrometer (AB Sciex, Toronto, ON, Canada) equipped with an electrospray ionization (ESI) source. The instrument was controlled by Analyst 1.5 software (AB Sciex). Targeted data acquisition was performed in multiple-reaction-monitoring (MRM) mode. We monitored 105 and 57 MRM transitions in negative and positive mode, respectively (162 transitions in total). The source and collision gas was $N_2$ (99.999% purity). The ion source conditions in negative/positive mode were as follows: curtain gas (CUR)=25 psi, collision gas (CAD)=high, ion spray voltage (IS)=−3.8/3.8 KV, temperature (TEM)=500° C., ion source gas 1 (GS1)=50 psi, and ion source gas 2 (GS2)=40 psi. The optimized MS compound conditions were optimized with chemical standards.

Data Analysis, Model Development, and Cross Validation:

The extracted MRM peaks were integrated, and the spectral data were exported using MultiQuant 2.1 software (AB Sciex). Sequential metabolite ratios (for example, the ratio of the same metabolite from the second blood draw to that from the first blood draw of the same patient) were used for the analyses. The calculated ratio values were linked to the disease status at the time of the most recent blood draw, and there were only three groups of disease status (CR, DP and SD) left after the ratio transformation.

Both univariate and multivariate statistical analyses were applied for metabolite biomarker discovery and model development on a selected set of biomarker candidates. Mann-Whitney U-tests, generation of receiver operator characteristics (ROC) curves, and calculation of sensitivity, specificity, and area under ROC curves (AUROCs) were calculated for each metabolite using JMP Pro10 (SAS Institute). Partial least squares-discriminant analysis (PLS-DA) and Monte Carlo Cross Validation (MCCV, developed using in-house scripts) were performed using Matlab software (Mathworks, Natick, Mass.) installed with the PLS toolbox (Eigenvector Research Inc., Wenatchee, Wash.). MCCV was applied with 100 iterations, using 70% of the data (randomly selected) as the training set while the remaining 30% served as the testing set for each iteration. Three specificities, 0.95, 0.85, and 0.75, for the training sets were used to determine the thresholds of PLS-DA predicted Y values. The same thresholds were then applied to the test set to determine sensitivities and specificities. The sample classification can be correctly assigned, termed "true class," or the sample class information can be randomly permuted, which is referred to as "random permutation."

Results

In the present study, a targeted LC-MS/MS metabolic profiling approach was developed to monitor CRC patient disease status using serial serum samples. The targeted platform allows the detection of 162 metabolites, representing more than 20 different classes (such as amino acids, carboxylic acids, pyridines, etc.) from 25 important metabolic pathways (e.g., TCA cycle, amino acid metabolism, purine and pyrimidine metabolism, glycolysis, etc.). In this study, 131 metabolites were reproducibly detected in the 49 samples, with an average coefficient of variation (CV) of 7.1%.

CEA values were available for all 49 samples and the resulting ROC curve is shown in FIG. 17A. The sensitivity and specificity were 0.86 and 0.44, respectively, for the typical cutoff values of 2.5 ng/mL (18). At 5 ng/mL (19), the sensitivity and specificity were 0.86 and 0.67, respectively. The AUROC was 0.77. Often, DP is better identified in CRC patients using CEA ratios calculated from sequential samples (15, 20), and therefore we also evaluated the CEA performance for CRC DP monitoring based on its ratio of serial blood draws from the same patient, although with 29 ratios for the 20 patients, we did not have sufficient samples to calculate exponentially fitted slopes (20). Using a ratio cutoff value of 1.2, the sensitivity and specificity are 0.75 and 0.76, respectively (lower cutoff values can be used, which would increase the detection sensitivity but also decrease the specificity). The area under ROC curve (AUROC) was 0.80 for the differentiation of DP from both CR and SD groups.

Metabolite data was then analyzed after calculating the sequential metabolite ratios for serial patient samples. Both univariate and multivariate statistical methods were used for metabolite biomarker selection. After applying the univariate Mann-Whitney U-test, 19 metabolites from different classes, such as monosaccharides, amino acids, carboxylic acids, and nucleosides, showed a significant statistical difference (p<0.05) between CRC DP and other CRC disease status (CR+SD). The p-values and fold changes for these metabolites are listed in Table 12. Furthermore, highly significant changes (defined as p<0.01) were found for six metabolites in comparison between disease progression and other disease status (CR+SD), namely succinate, N2, N2-dimethylguanosine, adenine, citraconic acid methylmalonate, and 1-methylguanosine. We established the individual ROCs for each of these six metabolites for monitoring the CRC disease progression (FIG. 18). Some of these metabolites had good AUROCs, such as 0.83 for succinate and 0.82 for N2, N2 dimethylguanosine, which have better performance than CEA (or its sequential sample ratio) alone.

TABLE 12

Summary of metabolites with low p-values (p < 0.05) using sequential metabolite ratio in comparing DP vs. CR + SD.

| Metabolite | p-value | FC* |
|---|---|---|
| Succinate | 2.80E−03 | 1.33 |
| N2,N2-Dimethylguanosine | 3.73E−03 | 1.34 |
| Adenine | 4.93E−03 | 1.11 |
| Citraconic Acid | 4.93E−03 | 1.58 |
| Methylmalonate | 4.93E−03 | 1.31 |
| 1-Methylguanosine | 8.42E−03 | 1.25 |
| 3-Nitro-tyrosine | 1.24E−02 | 0.84 |
| Aconitate | 1.40E−02 | 1.45 |
| Cystathionine | 1.58E−02 | 0.65 |
| Urate | 1.78E−02 | 1.15 |
| Ornithine | 2.53E−02 | 0.91 |
| Homogentisate | 2.84E−02 | 1.19 |
| G16BP | 3.17E−02 | 1.05 |
| Galactose | 3.17E−02 | 0.36 |
| MethylSuccinate | 3.17E−02 | 0.80 |
| Oxaloacetate | 4.39E−02 | 1.30 |
| Pyruvate | 4.39E−02 | 0.64 |
| 2-Aminoadipate | 4.88E−02 | 1.38 |
| F16BP/F26BP | 4.88E−02 | 1.03 |

*Fold change represents the average metabolite ratio for disease progression samples compared to the average metabolite ratio of samples from other groups.

Furthermore, PLS-DA was utilized to identify the performance of multiple metabolite biomarkers in combination for monitoring CRC DP. Variable importance in projection (VIP) scores from the PLS-DA of all metabolites were calculated to evaluate those metabolites that contributed most to the differentiation of CRC DP from CR and SD (see Table 16 for metabolites with low p-value (p<0.05) in comparison of DP vs. CR+SD; and Table 17 for metabolites with VIP>1.5). A series of PLS-DA models were then established based on the different VIP thresholds (from 1.5 to 2), and the model performances were evaluated and are listed in Table 13. Interestingly, when the VIP threshold was set to 2, five out of the six metabolites (succinate, N2, N2-dimethylguanosine, adenine, citraconic acid and 1-methylguanosine) that had p<0.01 were again selected as important biomarkers for CRC DP monitoring.

TABLE 13

Summary of PLS-DA model performance using different numbers of sequential metabolite ratios for the differentiation of DP vs. CR + SD.

| PLS-DA Models | Metabolites selection Threshold | # of Metabolites used in the model* | AUROC | Sensitivity | Specificity |
|---|---|---|---|---|---|
| DP vs. CR + SD (Metabolites only models) | VIP > 1.5 | 20 | 0.92 | 0.92 | 0.88 |
| | VIP > 1.8 | 7 | 0.90 | 0.83 | 0.94 |
| | VIP > 2 | 5 | 0.91 | 0.83 | 0.94 |
| DP vs. CR + SD (Metabolites + CEA models) | VIP > 1.5 | 20 | 0.92 | 0.92 | 0.88 |
| | VIP > 1.8 | 7 | 0.89 | 0.83 | 0.94 |
| | VIP > 2 | 5 | 0.91 | 0.83 | 0.94 |

*See Table 17 for metabolites and their corresponding VIP scores.

TABLE 16

Summary of MS parameters for the metabolites with low p-value (p < 0.05) in comparison of DP vs. CR + SD.

| Metabolite | Pos/Neg mode | Ret. Time (Min) | Q1/Q3 Mass (Da) | Declustering Potential (Volts) | Collision Energy (Volts) |
|---|---|---|---|---|---|
| Succinate | Neg | 2.28 | 117/73 | −50 | −18 |
| N2,N2-Dimethylguanosine | Pos | 1.77 | 312/180 | 200 | 47 |
| Adenine | Neg | 3.06 | 134/107 | −250 | −25 |
| Citraconic Acid | Neg | 2.56 | 129/85 | −50 | −15 |
| Methylmalonate | Neg | 2.28 | 117/73 | −50 | −18 |
| 1-Methylguanosine | Pos | 2.08 | 298/166 | 65 | 33 |
| 3-Nitro-tyrosine | Neg | 3.62 | 225/179 | −50 | −16 |
| Aconitate | Neg | 2.55 | 173/129 | −65 | −20 |
| Cystathionine | Neg | 7.96 | 221/134 | −75 | −20 |
| Urate | Neg | 2.94 | 167/124 | −85 | −22 |
| Ornithine | Pos | 2.27 | 133/70 | 75 | 25 |
| Homogentisate | Neg | 2.94 | 167/123 | −75 | −20 |
| G16BP | Neg | 9.07 | 339/79 | −120 | −60 |
| Galactose | Neg | 2.61 | 179/89 | −50 | −15 |
| MethylSuccinate | Neg | 4.45 | 131/113 | −80 | −20 |
| Oxaloacetate | Neg | 1.84 | 131/87 | −70 | −12 |
| Pyruvate | Neg | 2.22 | 87/43 | −75 | −12 |
| 2-Aminoadipate | Neg | 2.64 | 160/116 | −60 | −20 |
| F16BP/F26BP | Neg | 9.07 | 339/79 | −120 | −60 |

TABLE 17

Summary of metabolites with high VIP scores (VIP > 1.5) using sequential metabolite ratios in comparing DP vs. CR + SD.

| Metabolite | VIP | FC* |
|---|---|---|
| N2,N2-Dimethylguanosine | 2.15 | 1.34 |
| Citraconic Acid | 2.04 | 1.58 |
| 1-Methylguanosine | 2.04 | 1.25 |
| Succinate | 2.01 | 1.33 |
| Adenine | 2.01 | 1.11 |
| Methylmalonate | 1.84 | 1.31 |
| 3-Nitro-tyrosine | 1.83 | 0.84 |
| Malonic Acid/3HBA | 1.77 | 5.99 |
| G16BP | 1.76 | 1.05 |
| Urate | 1.76 | 1.15 |
| Aconitate | 1.73 | 1.45 |
| Homogentisate | 1.66 | 1.19 |
| MethylSuccinate | 1.61 | 0.80 |
| 1-Methyladenosine | 1.61 | 1.15 |
| Cystathionine | 1.60 | 0.65 |
| Linolenic Acid | 1.58 | 1.77 |
| Cytidine | 1.57 | 1.39 |
| Pyruvate | 1.57 | 0.64 |
| Alanine | 1.55 | 0.80 |
| gama-Aminobutyrate | 1.53 | 0.82 |

*Fold change represents the average metabolite ratio for disease progression samples compared to the average metabolite ratio of samples from other groups.

A PLS-DA model using only these five core metabolite biomarkers was then applied to evaluate the performance of this approach for CRC DP monitoring, and the ROC curve generated for this metabolite model is shown in FIG. 19A. The AUROC for this five metabolite model demonstrated excellent performance with an AUROC of 0.91, a sensitivity of 0.83 and a specificity of 0.94. To further test the robustness of this model, MCCV was applied with three different specificities. The true classification models clearly outperformed the random permutation models (FIG. 19B), suggesting that the five core metabolite biomarker model is reliable for the CRC DP monitoring.

Figure 20B:
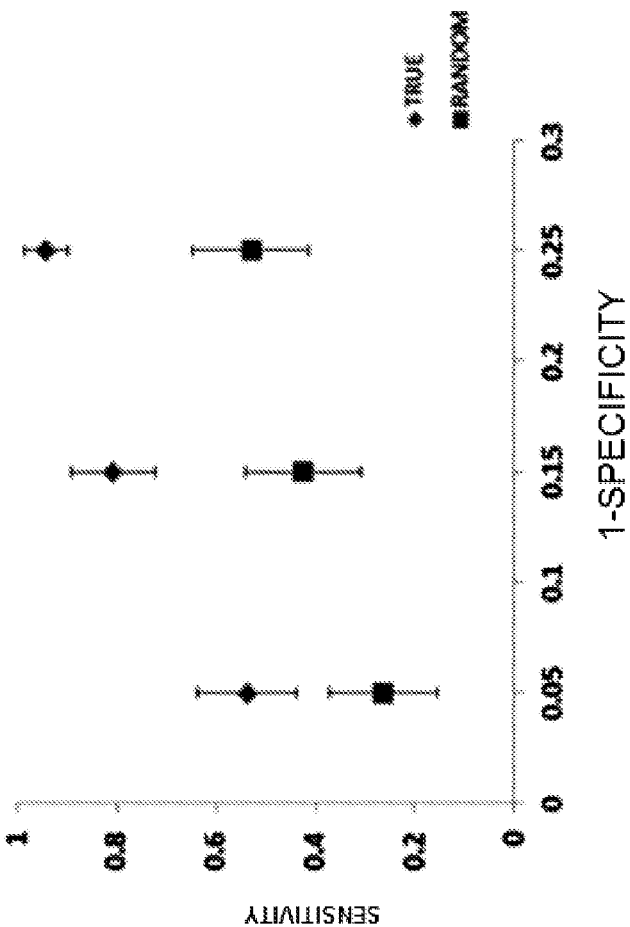
FIGS. 20A-20B. Sensitivity and specificity when using five metabolites plus CEA. (20A) ROC of PLS-DA model using five metabolites (with VIP>2) and CEA ratios for DP vs. CR+SD: AUROC=0.912 (increased from 0.907, see FIG. 19); sensitivity=0.83; specificity=0.94. (20B) Monte Carlo cross validation (MCCV) PLS-DA results using the same metabolites: True, true class models; Random, random permutation model. The testing specificities were 0.95, 0.85, and 0.75.
Figure 20A:
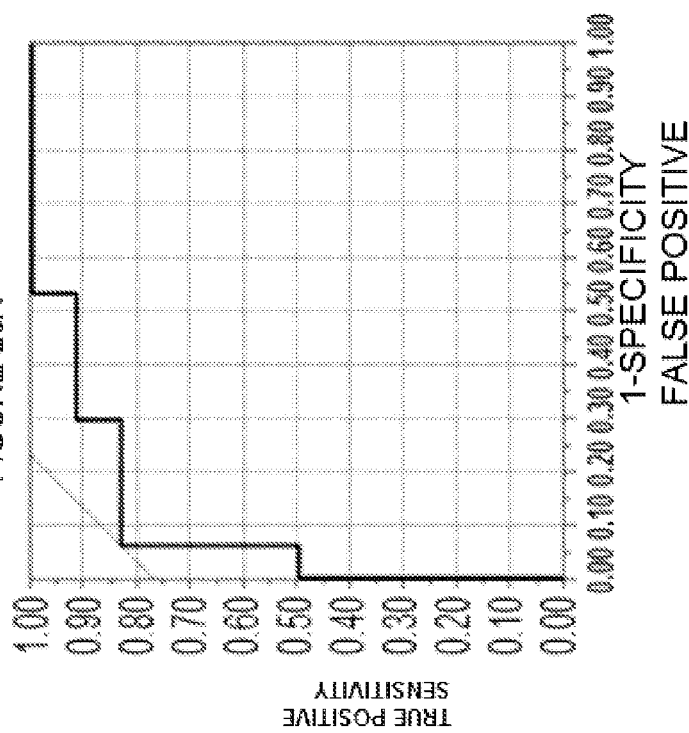

The model was further enhanced by adding the CEA ratio to the five metabolite model. Slightly improved performance (AUROC increased from 0.907 to 0.912) was obtained by adding the CEA ratio to the 5 metabolite ratio model (FIG. 20), suggesting that the combination of both metabolite biomarkers and CEA may provide the most utility for the close monitoring of patients for CRC DP.

To improve the potential for metabolite applications for more specific disease status differentiation, PLS-DA models were also evaluated in this study for DP vs. SD and DP vs. CR, and the model performance can be seen in Table 14. It is interesting to note that when only comparing the CRC DP to either SD or CR, two important CRC disease statuses in CRC monitoring, excellent model performances was obtained (with AUROC=0.95 for DP vs. SD using 7 metabolites, and AUROC=0.91 for DP vs. CR using 6 metabolites, FIG. 21).

TABLE 14

Summary of PLS-DA model performance using sequential metabolite ratios for the differentiation of DP vs. CR and DP vs. SD.

| PLS-DA Models | Metabolites selection Threshold | # of Metabolites used in the model | AUROC | Sensitivity | Specificity |
|---|---|---|---|---|---|
| DP vs. CR (Metabolites only models) | VIP > 1.5 | 17 | 0.94 | 0.89 | 0.92 |
| | VIP > 1.7 | 8 | 0.96 | 0.83 | 1.00 |
| | VIP > 1.9 | 4 | 0.92 | 0.75 | 1.00 |
| DP vs. CR (Metabolites + CEA models) | VIP > 1.5 | 17 | 0.94 | 0.92 | 0.89 |
| | VIP > 1.8 | 6 | 0.91 | 0.83 | 1.00 |
| | VIP > 1.9 | 4 | 0.91 | 0.75 | 1.00 |
| | VIP > 2 | 1 | 0.84 | 0.75 | 1.00 |
| DP vs. SD (Metabolites only models) | VIP > 1.5 | 17 | 0.94 | 0.92 | 1.00 |
| | VIP > 1.7 | 10 | 0.95 | 0.92 | 1.00 |
| | VIP > 1.9 | 4 | 0.92 | 0.92 | 0.88 |
| | VIP > 2 | 2 | 0.95 | 0.93 | 1.00 |
| DP vs. SD (Metabolites + CEA models) | VIP > 1.5 | 17 | 0.94 | 0.92 | 1.00 |
| | VIP > 1.8 | 7 | 0.95 | 0.92 | 1.00 |
| | VIP > 1.9 | 4 | 0.94 | 0.92 | 0.88 |

Discussion

During the past several decades, the search for new and better biomarkers has become an important part of cancer research. Sensitive, specific, and reliable metabolite biomarkers can serve multiple clinical purposes, such as cancer diagnostics, recurrence monitoring, and prognosis management, as well as understanding disease mechanisms (21, 22). In the case of CRC, efforts have been made to discover and evaluate potential metabolite biomarkers for diagnostics procedures (7, 8, 10, 23), and good performance for using these combinations of metabolite biomarkers can be observed (AUROC range from 0.88 to 0.97). However, there are also healthcare needs for closely monitoring CRC patients after surgeries/treatments, to ensure that patients remain disease free or are treated promptly in case of relapse. Metabolomics research focusing on this area is largely lacking.

Currently, one of the most frequently used clinical biomarkers for CRC disease status monitoring is CEA, and high preoperative concentrations of CEA would normally correlate with adverse prognosis. Based on the available reports, it appears that monitoring all CRC patients with serial CEA assays has only a modest effect on patient outcome, and serial CEA measurements can detect recurrent colorectal cancer with a sensitivity of ~80%, a specificity of ~70% (17), which is consistent with our evaluation in this study. In order to provide an alternative CRC monitoring tool with better performance, we propose an LC-MS/MS targeted serum metabolite profiling approach. Sequential metabolite ratios, combined with a multivariate statistical analysis were used to evaluate the usefulness of metabolite biomarkers for CRC disease progression monitoring. Excellent model performance (AUROC=0.91) was obtained for the differentiation of CRC disease progression status from CR and SD, using five core metabolite markers in our PLS-DA model. Using 20 metabolites, based on VIP score >1.5, an even better performance was achieved (AUROC=0.92). After robustness testing using MCCV, a clear distinction between the true classification models and random permutation models was observed. Furthermore, enhanced performance was also obtained by adding the five core metabolite model to the CEA ratio (AUROC=0.91). This result again suggests the potential usefulness of this targeted metabolite profiling approach for CRC DP monitoring. The five core metabolite model outperformed the CEA data alone, suggesting that better sensitivity and specificity for CRC disease status monitoring can be obtained by applying the metabolite biomarker models separately, or together with CEA.

Significantly changed metabolites discovered in this study are involved in multiple important metabolic pathways, such as the tricarboxylic acid (TCA) cycle, glycolysis, amino acid metabolism, purine metabolism, the urea cycle and their related pathways. Therefore, an effort was made to understand the possible connections among these serum metabolites. A metabolic pathway map was constructed using reference information obtained from the Kyoto Encyclopedia of Genes and Genomes website (www.genome.jp/kegg/) and is shown in FIG. 22. Six significantly altered metabolites in this study, namely galactose, pyruvate, cystathionine, 3 nitro-tyrosine, ornithine, and methyl succinate, showed decreased levels in CRC DP serum samples in comparison with CR and SD. On the other hand, thirteen significantly altered metabolites, including glucose 1, 6-bisphosphate (G16BP), fructose 1, 6-bisphosphate (F16BP), 1-methylguanosine, 2-aminoadipate, citraconic acid, N2, N2-dimethylguanosine, oxaloacetate, cis-aconitate, succinate, homogentisate, methylmalonate, adenine, and urate increased in the CRC DP group. Several of the biological discoveries in this study are consistent with previously published results. For example, G16BP and F16BP showed a significant increase in progressing patients. A recent gastric cancer study suggested that fructose-1, 6-bisphosphatase-2 (FBP2), the enzyme that catalyzes the hydrolysis of F16BP to fructose-6-phosphate and inorganic phosphate in glucose metabolism, was down regulated in gastric cancer patient tissue (24), which could lead to the accumulation of upstream F16BP. Pyruvate, the major downstream product of glycolysis, was significantly lower in CRC DP patients compared to CR and SD in this study, which matches the observation from several other studies (25, 26). The proposed mechanisms behind this observation are that CRC cancer cells try to maintain low levels of pyruvate to avoid cell death caused by histone deacetylases (HDAC) (26), and also overexpress pyruvate dehydrogenase kinase to increase drug resistance and early recurrence (25). Increased levels of modified nucleosides, such as N2, N2-dimethylguanine, have been observed in urine from patients suffering from CRC (27, 28), which is also in agreement with the current study. Increased levels of three TCA cycle metabolites (succinate, oxaloacetate and cis-aconitate) were observed in this study, which may suggest a typical metabolic fingerprint of mitochondrial dysfunction in hypoxic cells (29); however, it is uncertain what causes the accumulation of these metabolites in CRC DP samples.

This is the first study in which an LC-MS/MS targeted serum metabolic profiling approach has been applied to distinguish CRC DP patients from CRC patients with other disease status (SD and CR). Our results demonstrate that a panel of five core serum metabolites (succinate, N2, N2-dimethylguanosine, adenine, citraconic acid methylmalonate, and 1-methylguanosine) can be used for sensitive and specific CRC disease status monitoring. Furthermore, with the enhancement of adding CEA to the model, this metabolic profiling approach can potentially serve as a novel tool for CRC disease status monitoring and provide useful information for many CRC related healthcare decisions. While these findings with a small samples size are promising, further studies with larger patient cohorts will be needed to substantiate the results, verify the important biological roles of these key metabolites, and determine any association of the derived metabolite markers with pathologically different CRC disease status. Considering their strong performance as biomarkers in the present study, these five core metabolites as well as larger profiles might be of particular interest for further validation studies.

References Cited in Example 3

1. Siegel R, et al. CA Cancer J Clin. 2014; 64:9-29.
2. Plaks V, et al. Science. 2013; 341:1186-8.
3. Pesta M, et al. Anticancer Res. 2013; 33:2239-43.
4. Link A, et al. Cancer Epidemiol Biomark Prev. 2010; 19:1766-74.
5. Ahlquist D A et al. Gastroenterology. 2012; 142:248-56.
6. Bi X, et al. Mol Cell Proteomics. 2006; 5:1119-30.
7. Leichtle A, et al. Metabolomics. 2012; 8:643-53.
8. Nishiumi S, et al. PLoS ONE. 2012; 7:e40459.
9. Li F, et al. Rapid Commun Mass Spectrom. 2013; 27:24-34.
10. Tan B, et al. J Proteome Res. 2013; 12:3000-9.
11. Mook O R F, et al. Biochimica et Biophysica Acta (BBA)—Reviews on Cancer. 2004; 1705:69-89.
12. Pantel K, Brakenhoff R H. Nat Rev Cancer. 2004; 4:448-56.
13. Taylor I. Br J Surg. 1996; 83:456-60.
14. Fletcher R H. Ann Intern Med. 1986; 104:66-73.

15. Staab H J, et al. The American Journal of Surgery. 1978; 136:322-7.
16. Ludwig J A, Weinstein J N. Nat Rev Cancer. 2005; 5:845-56.
17. Duffy M J. Clin Chem. 2001; 47:624-30.
18. Larson F C, et al. J Clin Oncol. 1984; 2:457-61.
19. Locker G Y, et al. J Clin Oncol. 2006; 24:5313-27.
20. Iwanicki-Caron I, et al. J Clin Oncol. 2008; 26:3681-6.
21. Nagrath D, et al. Biochimica et Biophysica Acta (BBA)—Bioenergetics. 2011; 1807:650-63.
22. Spratlin J L, et al. Clin Cancer Res. 2009; 15:431-40.
23. Mal M, et al. Anal Bioanal Chem. 2012; 403:483-93.
24. Li H, Wang J, et al. Mol Cancer. 2013; 12:110.
25. Lu C-W, et al. The American Journal of Pathology. 2011; 179:1405-14.
26. Thangaraju M, et al. Biochem J. 2009; 417:379-89.
27. Hsu W-Y, et al. Clin Chim Acta. 2009; 402:31-7.
28. Gehrke C W, et al. Cancer Res. 1979; 39:1150-3.
29. Hirayama A, et al. Cancer Res. 2009; 69:4918-25.

Example 4: Use of a Subset of 8 Metabolites for Detecting Colon Cancer

Figure 23D:
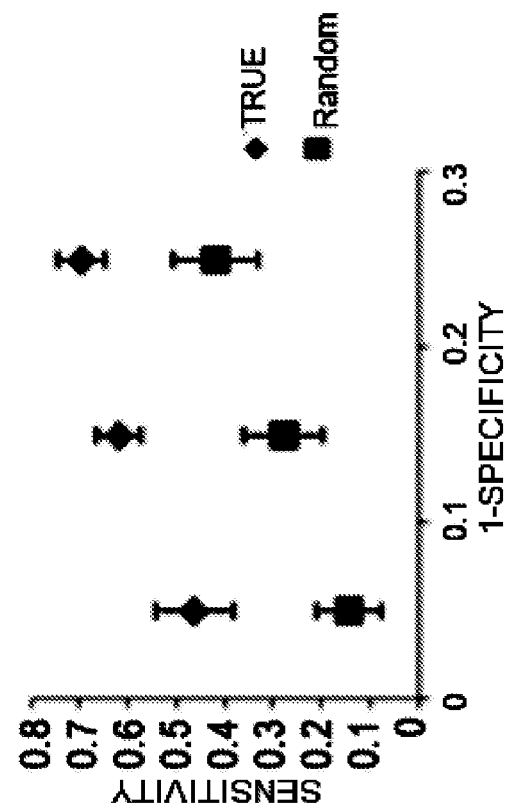
Figure 23C:
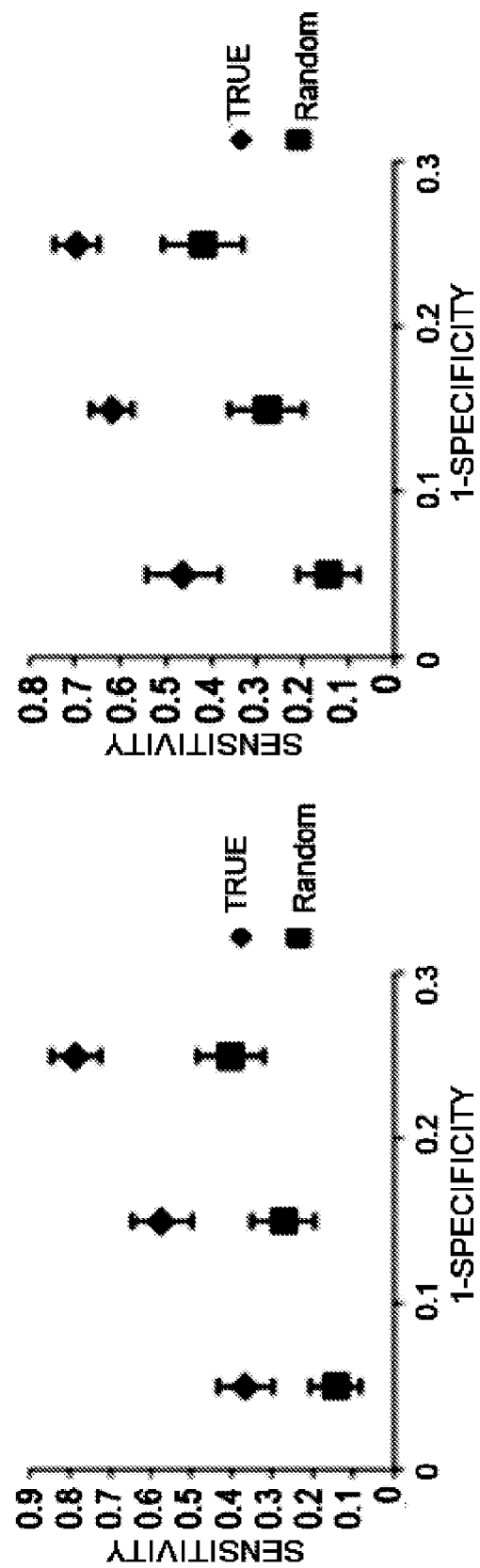

Eight core metabolites that have VIP scores >1 and have shown up in both CRC vs. Healthy control comparison and CRC vs. Polyp patients comparison are: Glyceraldehyde, Hippuric Acid, Glycochenodeoxycholate, Glycocholate, Linolenic Acid, Hydroxyproline/Aminolevulinate, N-AcetylGlycine, and Leucic Acid. Modified PLS-DA models were built, using only these eight metabolite values in both comparison. Results of the models can be seen in FIGS. 23A and 23B, Monte Carlo Cross Validation (MCCV) was also applied on these models, and clear separation between true class and random permutation can be observed as well (FIGS. 23C and 23D).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating colorectal cancer (CRC) progression in a subject, the method comprising:
   (a) measuring the concentrations of at least five components of a panel of a plurality of serum metabolites in a serum sample from the subject, wherein the components of the panel are selected from the group consisting of:
   succinate, N2,N2-dimethylguanosine, adenine, citraconic acid, methylmalonate, 1-methylguanosine, and 3-nitrotyrosine;
   (b) determining a ratio of the concentration of each of the components measured in step (a) to a control serum concentration of each of the components;
   (c) determining CRC progression in the subject when the ratio determined in (b) is less than 0.85 or greater than 1.15 for at least five of the components; and
   (d) treating the subject for CRC progression.

2. The method of claim 1, wherein the ratio determined in step (b) is less than 0.9 or greater than 1.1.

3. The method of claim 1, wherein the ratio of component 3-Nitro-tyrosine is less than 0.9, and the ratio of components succinate, N2,N2-dimethyl-guanosine, adenine, citraconic acid, methylmalonate, and 1-methylguanosine is greater than 1.1.

4. The method of claim 1, wherein the at least five components comprise succinate, N2,N2-dimethylguanosine, adenine, citraconic acid, and 1-methylguanosine.

5. The method of claim 1, wherein the control serum is obtained from a normal, healthy subject or obtained from the subject at an earlier time.

6. The method of claim 1, further comprising measuring the concentrations of at least one additional serum metabolite selected from the group consisting of:
   malonic acid/3HBA, G16BP, urate, aconitate, homogentisate, methylsuccinate, 1-methyladenosine, cystathionine, linolenic acid, cytidine, pyruvate, alanine, and gama-aminobutyrate.

7. The method of claim 1, further comprising measuring carcinoembryonic antigen (CEA) in a serum sample from the subject, wherein a statistically significant increase in CEA relative to a control sample is indicative of progression of CRC.

8. The method of claim 1, wherein the measuring comprises liquid chromatography, mass spectrometry, enzymatic assay, and/or immunoassay.

9. The method of claim 1, wherein the concentration of each of the components is measured.

10. The method of claim 6, wherein the concentration of 20 metabolites is measured.

11. The method of claim 7, wherein the CEA in the serum sample is greater than or equal to 2.5 ng/ml.

12. The method of claim 1, wherein the ratio determined in step (b) is less than 0.95 or greater than 1.2.

13. The method of claim 1, wherein the subject is or has been on treatment, and wherein treating the subject for CRC progression comprises an adjustment to therapy.

14. The method of claim 1, wherein treating the subject for CRC progression comprises surgery, chemotherapy, or radiation treatment.

15. The method of claim 14, wherein the treating comprises chemotherapy.

* * * * *